United States Patent
Youngblood et al.

(10) Patent No.: US 12,251,521 B2
(45) Date of Patent: *Mar. 18, 2025

(54) STRESS REDUCTION AND SLEEP PROMOTION SYSTEM

(71) Applicant: Sleep Solutions Inc., Wilmington, DE (US)

(72) Inventors: Tara Youngblood, Mooresville, NC (US); Todd Youngblood, Mooresville, NC (US)

(73) Assignee: Sleep Solutions Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,084

(22) Filed: Jan. 23, 2024

(65) Prior Publication Data

US 2024/0157085 A1     May 16, 2024

Related U.S. Application Data

(63) Continuation of application No. 17/679,821, filed on Feb. 24, 2022, now Pat. No. 11,883,606, which is a
(Continued)

(51) Int. Cl.
*A61M 21/00* (2006.01)
*G06F 3/01* (2006.01)
*G16H 20/70* (2018.01)

(52) U.S. Cl.
CPC ............ *A61M 21/00* (2013.01); *G06F 3/011* (2013.01); *G16H 20/70* (2018.01); *A61M 2021/0066* (2013.01); *A61M 2205/3327* (2013.01); *A61M 2205/3553* (2013.01); *A61M 2205/3561* (2013.01); *A61M 2205/502* (2013.01);
(Continued)

(58) Field of Classification Search
CPC ............ A61M 21/00; A61M 2021/006; A61M 2021/0066; A61M 2205/3553; A61M 2205/3561; A61M 2205/502; A61M 2230/04; A61M 2230/10; A61M 2230/14;
(Continued)

(56) References Cited

U.S. PATENT DOCUMENTS 2,753,435 A   7/1956   Ivar
3,230,556 A   1/1966   Wiusor
(Continued)

FOREIGN PATENT DOCUMENTS

| KR | 20060019762 A | 3/2006 |
|---|---|---|
| KR | 20110102637 A | 9/2011 |
| WO | 2014145436 A1 | 9/2014 |

OTHER PUBLICATIONS

Buysse, D.J., Reynolds, C.F., Monk, T.H., Berman, S.R., & Kupfer, D.J. (1989). The Pittsburgh Sleep Quality Index (PSQI): A new instrument for psychiatric research and practice. Psychiatry Research, 28(2), 193-213.
(Continued)

*Primary Examiner* — Nael N Babaa
(74) *Attorney, Agent, or Firm* — POLSINELLI PC

(57) ABSTRACT

The present invention provides systems, methods, and articles for stress reduction and sleep promotion. A stress reduction and sleep promotion system includes at least one remote device, at least one body sensor, and at least one remote server. In other embodiments, the stress reduction and sleep promotion system includes machine learning.

20 Claims, 60 Drawing Sheets

Related U.S. Application Data continuation-in-part of application No. 17/570,035, filed on Jan. 6, 2022, now abandoned, which is a continuation of application No. 17/553,470, filed on Dec. 16, 2021, now abandoned, which is a continuation-in-part of application No. 16/686,394, filed on Nov. 18, 2019, now Pat. No. 11,813,076, which is a continuation-in-part of application No. 15/848,816, filed on Dec. 20, 2017, now Pat. No. 11,013,883, which is a continuation-in-part of application No. 15/705,829, filed on Sep. 15, 2017, now Pat. No. 10,986,933, which is a continuation-in-part of application No. 14/777,050, filed as application No. PCT/US2014/030202 on Mar. 17, 2014, now Pat. No. 10,278,511.

(60) Provisional application No. 62/769,183, filed on Nov. 19, 2018, provisional application No. 62/398,257, filed on Sep. 22, 2016, provisional application No. 61/800,768, filed on Mar. 15, 2013.

(52) U.S. Cl.
CPC ..... *A61M 2230/04* (2013.01); *A61M 2230/10* (2013.01); *A61M 2230/14* (2013.01); *A61M 2230/205* (2013.01); *A61M 2230/50* (2013.01); *A61M 2230/63* (2013.01)

(58) Field of Classification Search
CPC ........ A61M 2230/205; A61M 2230/50; A61M 2230/63; G16H 20/70; G06F 3/011
See application file for complete search history.

(56) References Cited

U.S. PATENT DOCUMENTS

| | | |
|---|---|---|
| 4,132,262 A | 1/1979 | Wibell |
| 4,459,468 A | 7/1984 | Bailey |
| 4,777,802 A | 10/1988 | Feher |
| 4,858,609 A | 8/1989 | Cole |
| 5,033,136 A | 7/1991 | Elkins |
| 5,304,112 A | 4/1994 | Mrklas et al. |
| 5,329,096 A | 7/1994 | Suematsu |
| 5,448,788 A | 9/1995 | Wu |
| 5,894,615 A | 4/1999 | Alexander |
| 5,948,303 A | 9/1999 | Larson |
| 6,163,907 A | 12/2000 | Larson |
| 6,273,810 B1 | 8/2001 | Rhodes, Jr. et al. |
| 6,371,976 B1 | 4/2002 | Vrzalik et al. |
| 6,463,743 B1 | 10/2002 | Laliberté |
| 6,484,062 B1 | 11/2002 | Kim |
| 6,581,224 B2 | 6/2003 | Yoon |
| 6,826,792 B2 | 12/2004 | Lin |
| 7,041,049 B1 | 5/2006 | Raniere |
| 7,238,289 B2 | 7/2007 | Suddath |
| 7,248,915 B2 | 7/2007 | Rönnholm |
| 7,306,567 B2 | 12/2007 | Loree |
| 7,382,047 B2 | 6/2008 | Chen et al. |
| 7,460,899 B2 | 12/2008 | Almen |
| 7,524,279 B2 | 4/2009 | Auphan |
| 7,546,653 B2 | 6/2009 | Ye |
| 7,608,041 B2 | 10/2009 | Sutton |
| 7,699,785 B2 | 4/2010 | Nemoto |
| 7,868,757 B2 | 1/2011 | Radivojevic et al. |
| 7,908,687 B2 | 3/2011 | Ward et al. |
| 8,096,960 B2 | 1/2012 | Loree et al. |
| 8,179,270 B2 | 5/2012 | Rai et al. |
| 8,191,187 B2 | 6/2012 | Brykalski et al. |
| 8,290,596 B2 | 10/2012 | Wei et al. |
| 8,348,840 B2 | 1/2013 | Heit et al. |
| 8,418,285 B2 | 4/2013 | Frias |
| 8,529,457 B2 | 9/2013 | Devot et al. |
| 8,617,044 B2 | 12/2013 | Pelgrim et al. |
| 8,768,520 B2 | 7/2014 | Oexman et al. |
| 8,979,730 B2 | 3/2015 | Naujokat et al. |
| 9,044,101 B2 | 6/2015 | Garcia et al. |
| 9,186,479 B1 | 11/2015 | Franceschetti et al. |
| 9,196,479 B1 | 11/2015 | Cheng et al. |
| 9,402,763 B2 | 8/2016 | Bledsoe |
| 9,459,597 B2 | 10/2016 | Kahn et al. |
| 9,750,415 B2 | 9/2017 | Breslow et al. |
| 9,981,107 B2 | 5/2018 | Franceschetti et al. |
| 9,993,195 B2 | 6/2018 | Van Vugt et al. |
| 9,999,744 B2 | 6/2018 | Proud |
| 10,154,932 B2 | 12/2018 | Franceschetti et al. |
| 10,179,064 B2 | 1/2019 | Connor |
| 10,188,222 B2 | 1/2019 | Veron |
| 10,216,485 B2 | 2/2019 | Misra et al. |
| 10,350,108 B1 | 7/2019 | Rittman, III et al. |
| 10,391,009 B2 | 8/2019 | Bhai |
| 10,398,357 B2 | 9/2019 | Chen et al. |
| 10,401,807 B2 | 9/2019 | Jo et al. |
| 10,675,434 B2 | 6/2020 | Van Driel et al. |
| 10,686,626 B2 | 6/2020 | Sarwar et al. |
| 10,709,335 B2 | 7/2020 | Matsuoka et al. |
| 10,764,079 B2 | 9/2020 | Mahar et al. |
| 10,764,374 B1 | 9/2020 | Marquardt et al. |
| 10,824,634 B2 | 11/2020 | Siebel et al. |
| 10,833,888 B2 | 11/2020 | Kim et al. |
| 10,923,226 B2 | 2/2021 | Macary et al. |
| 10,959,667 B2 | 3/2021 | Xin et al. |
| 10,971,261 B2 | 4/2021 | Kahn et al. |
| 11,040,169 B2 | 6/2021 | Jung et al. |
| 11,097,079 B2 | 8/2021 | Shanmugam et al. |
| 11,134,888 B2 | 10/2021 | Wright et al. |
| 11,185,281 B2 | 11/2021 | Molina et al. |
| 2002/0014951 A1 | 2/2002 | Kramer et al. |
| 2002/0080035 A1 | 6/2002 | Youdenko |
| 2002/0124574 A1 | 9/2002 | Guttman et al. |
| 2004/0049132 A1 | 3/2004 | Barron et al. |
| 2005/0143617 A1 | 6/2005 | Auphan |
| 2005/0154330 A1 | 7/2005 | Loree |
| 2006/0137099 A1 | 6/2006 | Feher |
| 2006/0293602 A1 | 12/2006 | Clark |
| 2006/0293608 A1 | 12/2006 | Rothman et al. |
| 2007/0234741 A1 | 10/2007 | Lee et al. |
| 2008/0016881 A1 | 1/2008 | Steffensen et al. |
| 2008/0234785 A1 | 9/2008 | Nakayama et al. |
| 2009/0112069 A1 | 4/2009 | Kanamori et al. |
| 2009/0121826 A1 | 5/2009 | Song et al. |
| 2009/0288800 A1 | 11/2009 | Kang et al. |
| 2010/0011502 A1 | 1/2010 | Brykalski et al. |
| 2010/0100004 A1 | 4/2010 | van Someren |
| 2010/0174198 A1 | 7/2010 | Young et al. |
| 2010/0197996 A1 | 8/2010 | Cornel |
| 2010/0199687 A1 | 8/2010 | Woods et al. |
| 2010/0293715 A1 | 11/2010 | Sakamoto et al. |
| 2010/0324611 A1 | 12/2010 | Deming et al. |
| 2011/0015327 A1 | 1/2011 | Bichler et al. |
| 2011/0015495 A1 | 1/2011 | Dothie et al. |
| 2011/0073292 A1 | 3/2011 | Datta et al. |
| 2011/0107514 A1 | 5/2011 | Brykalski et al. |
| 2011/0153274 A1 | 6/2011 | Ho et al. |
| 2011/0181597 A1 | 7/2011 | Cardno et al. |
| 2011/0230790 A1 | 9/2011 | Kozlov |
| 2011/0247139 A1 | 10/2011 | Tallent et al. |
| 2011/0252461 A1 | 10/2011 | Wetzer et al. |
| 2011/0267196 A1 | 11/2011 | Hu et al. |
| 2012/0054754 A1 | 3/2012 | Teichmann et al. |
| 2012/0136666 A1 | 5/2012 | Corpier et al. |
| 2012/0159968 A1 | 6/2012 | Doucet et al. |
| 2012/0296402 A1 | 11/2012 | Kotter |
| 2013/0019611 A1 | 1/2013 | Sims et al. |
| 2013/0060306 A1 | 3/2013 | Colbauch |
| 2013/0208576 A1 | 8/2013 | Loree, IV et al. |
| 2013/0234823 A1 | 9/2013 | Kahn et al. |
| 2013/0304768 A1 | 11/2013 | Basnight et al. |
| 2014/0006001 A1 | 1/2014 | Kamhi et al. |
| 2014/0208508 A1 | 7/2014 | Mikesell |
| 2014/0277308 A1 | 9/2014 | Cronise et al. |
| 2014/0316495 A1 | 10/2014 | Augustine et al. |
| 2015/0093101 A1 | 4/2015 | Lee |

(56) References Cited

U.S. PATENT DOCUMENTS

| | | |
|---|---|---|
| 2015/0203068 A1 | 7/2015 | Foo et al. |
| 2015/0257697 A1 | 9/2015 | Sepah |
| 2015/0289666 A1 | 10/2015 | Chandler et al. |
| 2015/0351982 A1 | 12/2015 | Krenik |
| 2015/0366703 A1 | 12/2015 | Du |
| 2016/0015184 A1 | 1/2016 | Nunn et al. |
| 2016/0015315 A1 | 1/2016 | Auphan et al. |
| 2016/0029808 A1 | 2/2016 | Youngblood et al. |
| 2016/0136385 A1 | 5/2016 | Scorcioni |
| 2016/0151603 A1 | 6/2016 | Shouldice et al. |
| 2016/0235610 A1 | 8/2016 | Drake |
| 2016/0239624 A1 | 8/2016 | Short et al. |
| 2016/0249842 A1 | 9/2016 | Lubelchick |
| 2016/0310697 A1 | 10/2016 | Franceschetti et al. |
| 2017/0003666 A1 | 1/2017 | Nunn et al. |
| 2017/0017759 A1 | 1/2017 | MacNeice et al. |
| 2017/0053068 A1 | 2/2017 | Pillai et al. |
| 2017/0095196 A1 | 4/2017 | Oakhill |
| 2017/0138663 A1 | 5/2017 | Wells |
| 2017/0189641 A1 | 7/2017 | Moturu et al. |
| 2017/0231812 A1 | 8/2017 | Boyden et al. |
| 2018/0000255 A1 | 1/2018 | Youngblood et al. |
| 2018/0082550 A1 | 3/2018 | Read et al. |
| 2018/0110960 A1 | 4/2018 | Youngblood et al. |
| 2018/0203744 A1 | 7/2018 | Wiesmaier et al. |
| 2018/0226155 A1 | 8/2018 | Mahoney et al. |
| 2018/0260387 A1 | 9/2018 | Ben-Kiki et al. |
| 2018/0285528 A1 | 10/2018 | Healey et al. |
| 2018/0325450 A1 | 11/2018 | Huang |
| 2018/0344517 A1 | 12/2018 | Nofzinger |
| 2019/0099009 A1 | 4/2019 | Connor |
| 2019/0203983 A1 | 7/2019 | Jeon et al. |
| 2019/0209405 A1 | 7/2019 | Sayadi et al. |
| 2019/0231081 A1 | 8/2019 | Youngblood et al. |
| 2019/0265971 A1 | 8/2019 | Behzadi et al. |
| 2019/0349254 A1 | 11/2019 | Nolan et al. |
| 2020/0027552 A1 | 1/2020 | Lee |
| 2020/0046134 A1 | 2/2020 | Youngblood et al. |
| 2020/0077942 A1 | 3/2020 | Youngblood et al. |
| 2020/0100682 A1 | 4/2020 | Abreu et al. |
| 2020/0113344 A1 | 4/2020 | Youngblood et al. |
| 2020/0171268 A1 | 6/2020 | Zhang |
| 2020/0178887 A1 | 6/2020 | Ramírez et al. |
| 2020/0205727 A1 | 7/2020 | Shen et al. |
| 2020/0215295 A1 | 7/2020 | LaPorte et al. |
| 2020/0229967 A1 | 7/2020 | Drew |
| 2020/0236907 A1 | 7/2020 | Nilsson et al. |
| 2020/0281521 A1 | 9/2020 | Cail |
| 2020/0289052 A1 | 9/2020 | Gross |
| 2020/0315368 A1 | 10/2020 | Tsern et al. |
| 2020/0337470 A1 | 10/2020 | Sayadi et al. |
| 2020/0397379 A1 | 12/2020 | Franceschetti et al. |
| 2021/0031000 A1 | 2/2021 | Lee et al. |
| 2021/0146091 A1 | 5/2021 | Kansagra |
| 2021/0178113 A1 | 6/2021 | Bresch et al. |
| 2021/0267379 A1 | 9/2021 | Youngblood et al. |
| 2021/0267380 A1 | 9/2021 | Stusynski |
| 2021/0314405 A1 | 10/2021 | Demirli et al. |
| 2022/0134050 A1 | 5/2022 | Moriyasu |
| 2022/0176065 A1 | 6/2022 | Youngblood et al. |
| 2022/0339398 A1 | 10/2022 | Youngblood et al. |

OTHER PUBLICATIONS

Quan, S. F. et. al; "Healthy Sleep The Characteristics of Sleep" (Sep. 21, 2016) pp. 1-4, retrieved from http://healthysleep.med.harvard.edu/healthy/science/what/characteristics.

Tobaldini, E. et. al; "Heart rate variability in normal and pathological sleep", Frontiers in Physiology, (Oct. 16, 2013), p. 1-11, vol. 4, Article 294, doi: 10.3389/fphys.2013.00294.

U.S. Appl. No. 61/800,768 Youngblood, Thermo electric heating and cooling device, filed Mar. 15, 2013, Drawings and Specification.

U.S. Appl. No. 62/398,257, Youngblood, Bed Pad With Custom Modulated Temperature Adjustment, filed Sep. 22, 2016, Drawings and Specification.

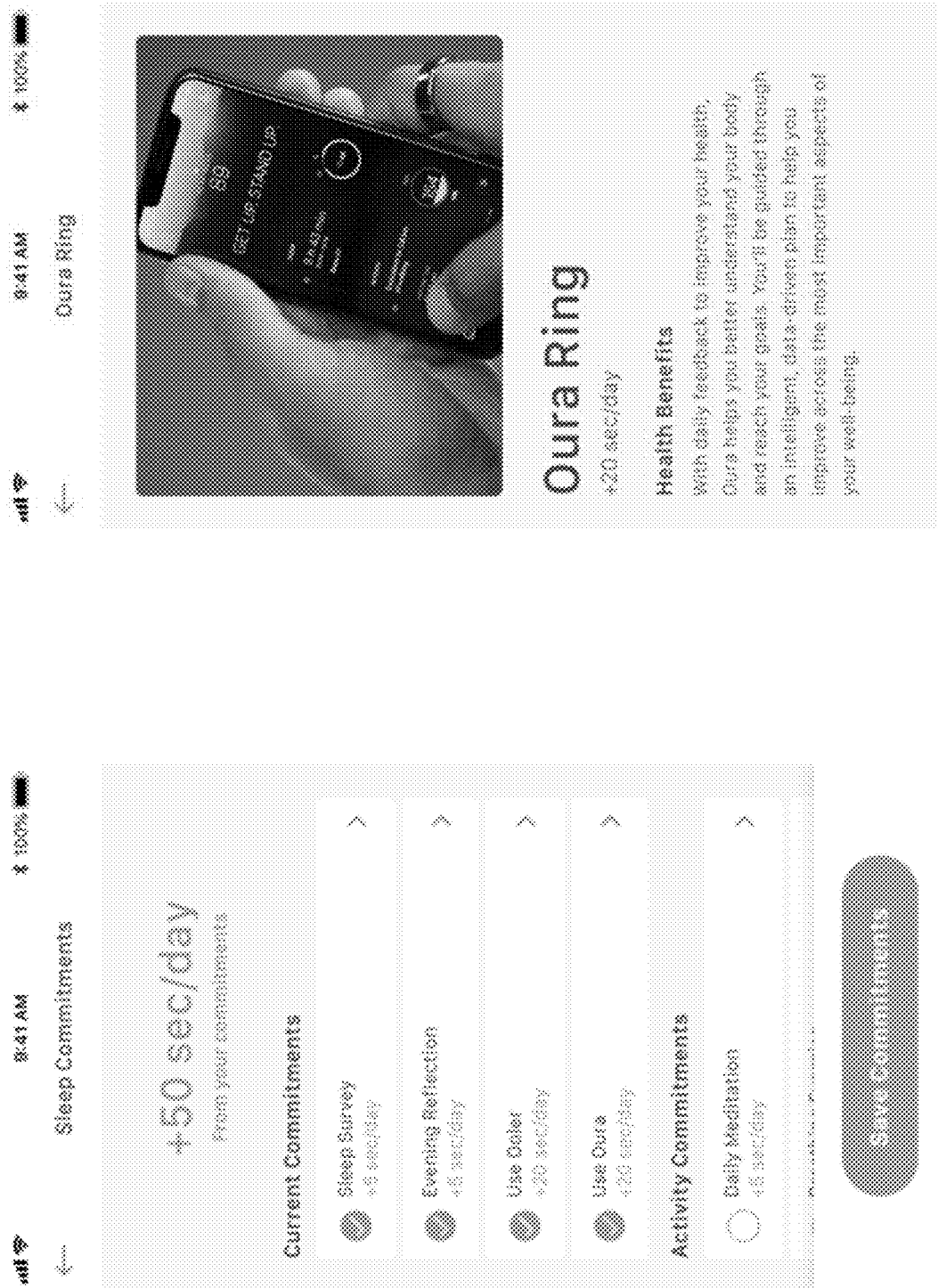

Chronotype Quiz

1. You have to do two hours of physically hard work. If you were entirely free to plan your day, in which of the following periods would you choose to do the work?
    a. 8:00 a.m. – 10:00 a.m. (4 points)
    b. 11:00 a.m. – 1:00 p.m. (3 points)
    c. 3:00 p.m. – 5:00 p.m. (2 points)
    d. 7:00 p.m. – 9:00 p.m. (1 point)
2. You have to take a two-hour test. You know it will be mentally exhausting. If you were entirely free to choose, when would you choose to take the test?
    a. 8:00 a.m. – 10:00 a.m. (4 points)
    b. 11:00 a.m. – 1:00 p.m. (3 points)
    c. 3:00 p.m. – 5:00 p.m. (2 points)
    d. 7:00 p.m. – 9:00 p.m. (1 point)
3. A friend has asked you to join him twice per week for a workout. The best time for him is between 10 p.m. and 11 p.m. With nothing else in mind other than how you normally feel in the evening, how do you think you would perform?
    a. Very poorly (4 points)
    b. Poorly (3 points)
    c. Well enough (2 points)
    d. Very well (1 point)
4. We hear about "morning" and "evening" types of people. Which of these types do you consider yourself?
    a. Definitely morning type (6 points)
    b. More a morning than an evening type (4 points)
    c. More an evening than a morning type (2 points)
    d. Definitely an evening type (0 points)

Add your scores together to get your total and compare your score with the table below to identify your chronotype.

| Points | Type |
|---|---|
| 14-16 | Morning person |
| 11-13 | Less morning person |
| 9-10 | Neither morning person nor night owl |
| 4-8 | Less night owl |
| 0-3 | Night owl |

FIG. 66

| User | Chronotype | Diet | Fitness | Intervention | Influencer | Coach |
|---|---|---|---|---|---|---|
| User 1 | Morning Person | WHOLE30 | Yoga, Swimming | Meditation, Journaling | Influencer 1, Influencer 2 | N/A |
| User 2 | Night Owl | Keto | Weights, Running | Journaling | Influencer 3 | N/A |
| User 3 | Neither Morning or Night Owl | Paleo | Cycling | Breathing Exercises | N/A | Coach 1 |
| User 4 | Less Night Owl | Fasting | Running | Tiny Habits | Influencer 4, Influencer 5 | Coach 2 |
| User 5 | Less Morning Person | Keto | Kickboxing | Meditation | Influencer 1, Influencer 4 | Coach 3 |
| User 6 | Morning Person | Vegan | Yoga | Meditation, Breathing Exercises | Influencer 2, Influencer 5 | Coach 2 |

FIG. 69

| Weekdays | 10 PM | 06 AM |
| Mon, Tue, Wed, Thu, Fri | Sleep time | Wake up time |
| Weekends | 10 PM | 06 AM |
| Sat, Sun | Sleep time | Wake up time |
Add Sleep Profile →
FIG. 79

FIG. 82

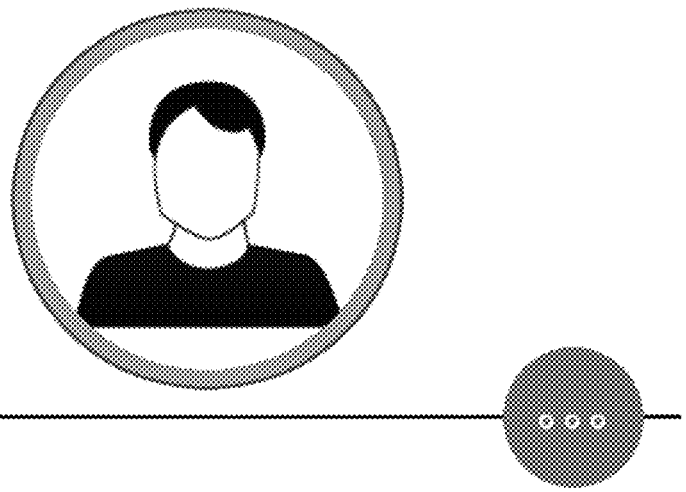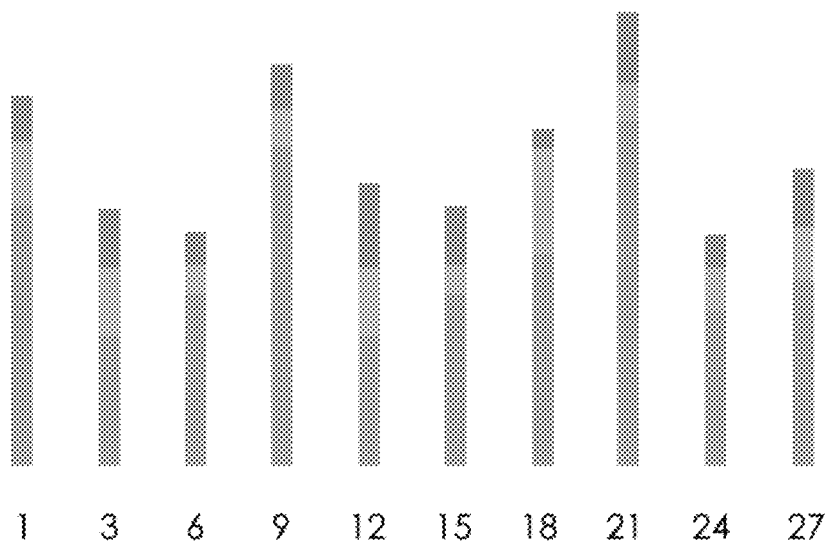
FIG. 84

STRESS REDUCTION AND SLEEP PROMOTION SYSTEM

CROSS REFERENCE TO RELATED APPLICATIONS

This application relates to and claims priority from the following applications. This application is a continuation of U.S. patent application Ser. No. 17/679,821, filed Feb. 24, 2022, which is a continuation-in-part of U.S. patent application Ser. No. 17/570,035, filed Jan. 6, 2022, which is a continuation of U.S. patent application Ser. No. 17/553,470, filed Dec. 16, 2021, which is a continuation-in-part of U.S. patent application Ser. No. 16/686,394, filed Nov. 18, 2019 and issued as U.S. Pat. No. 11,813,076, which claims the benefit of U.S. Provisional Patent Application No. 62/769,183, filed Nov. 19, 2018, and is a continuation-in-part of U.S. patent application Ser. No. 15/848,816, filed Dec. 20, 2017 and issued as U.S. Pat. No. 11,013,883. U.S. patent application Ser. No. 15/848,816 is a continuation-in-part of U.S. patent application Ser. No. 15/705,829, filed Sep. 15, 2017 and issued as U.S. Pat. No. 10,986,933, which is a continuation-in-part of U.S. patent application Ser. No. 14/777,050, filed Sep. 15, 2015 and issued as U.S. Pat. No. 10,278,511, which is the National Stage of International Application No. PCT/US2014/030202, filed Mar. 17, 2014, which claims the benefit of U.S. Provisional Patent Application No. 61/800,768, filed Mar. 15, 2013. U.S. patent application Ser. No. 15/705,829 also claims the benefit of U.S. Provisional Application No. 62/398,257, filed Sep. 22, 2016. Each of the above applications is incorporated herein by reference in its entirety.

BACKGROUND OF THE INVENTION

1. Field of the Invention

This invention relates broadly and generally to articles, methods, and systems for stress reduction and sleep promotion.

2. Description of the Prior Art

Several studies show that stress often negatively impacts health by causing diseases or exacerbating existing conditions. Stress impacts the individual on a physiological and psychological level. Further, stress often leads individuals to adopt health damaging behaviors (e.g., smoking, drinking, poor nutrition, lack of physical activity). These physiological changes and health damaging behaviors often cause illnesses, such as sleep disturbances, impaired wound healing, increased infections, heart disease, diabetes, ulcers, pain, depression, and obesity or weight gain.

Therefore, it is important to manage and treat stress to maintain health. However, many individuals are under increased pressure due to a modern lifestyle, which leaves less time for relaxation and sleep. This lack of stress relief and sleep results in an increase in both mental and physical stress.

Various methods of stress relief are known, including exercise, biofeedback, and meditation. These systems often include a physical device that stimulates the body and/or senses. These systems often shield the user from outside interferences.

Prior art patent documents include the following:

U.S. Pat. No. 10,154,932 for Adjustable bedframe and operating methods for health monitoring by inventors Franceschetti et al., filed Nov. 16, 2015 and issued Dec. 18, 2018, discloses methods and systems for an adjustable bed frame. The adjustable bed frame comprises a plurality of adjustable sections, where each section can be adjusted independently. The adjustable bed frame is coupled to a processor configured to: gather biological signals associated with multiple users, such as heart rate, breathing rate, or temperature; analyze the gathered human biological signals; and adjust the adjustable bed frame, based on the analysis.

U.S. Pat. No. 9,186,479 for Methods and systems for gathering human biological signals and controlling a bed device by inventors Franceschetti et al., filed Jun. 5, 2015 and issued Nov. 17, 2015, discloses methods and systems for an adjustable bed device configured to: gather biological signals associated with multiple users, such as heart rate, breathing rate, or temperature; analyze the gathered human biological signals; and heat or cool a bed based on the analysis.

U.S. Pat. No. 9,981,107 for Methods and systems for gathering and analyzing human biological signals by inventors Franceschetti et al., filed Jun. 5, 2015 and issued May 29, 2018, discloses methods and systems for: gathering human biological signals, such as heart rate, breathing rate, or temperature; analyzing the gathered human biological signals; and controlling home appliances based on the analysis.

U.S. Pat. No. 10,188,222 for Bed with embedded smart sensors by inventor Veron, filed Apr. 24, 2017 and issued Jan. 29, 2019, discloses a smart crib that includes a horizontal support platform and one or more vertical surfaces connected thereto that enclose a space above the horizontal support platform and/or define a space above the horizontal support platform. The horizontal support platform and/or the vertical surfaces may include one or more sensors that can be used to learn behavior of the crib occupant and/or determine conditions of the occupant and/or environment of the crib and/or the crib's surrounding area. The crib may receive responses from a client device and/or automatically act upon a detected condition in the crib or with the occupant.

U.S. Patent Publication No. 2020/0289052 for System for determining a sleep quality, sensor arrangement for such a system, and sleep or rest furniture comprising such a system by inventor Gross, filed May 15, 2018 and published Sep. 17, 2020, discloses a system for determining a value representing a sleep quality, wherein the system has an evaluation device for connecting to at least one sensor, which can be coupled to a piece of sleep or rest furniture for detecting vibrations, movement and/or sound in order to extract physiological data of at least one person using the piece of sleep or rest furniture. The system is characterized in that at least one additional sensor is provided on the sleep or rest furniture or in an environment of the sleep or rest furniture, which sensor is designed for detecting environmental parameters.

U.S. Patent Publication No. 2020/0178887 for Sleep monitoring system with optional alarm functionality by inventors Ramirez et al., filed Apr. 28, 2017 and published Jun. 11, 2020, discloses sleep tracking systems and techniques for monitoring two or more co-sleepers in a single bed. Such systems and techniques may incorporate sleeper identification, as well as various non-user-specific aspects. Some implementations may incorporate user-specific or user-tailored alarm functionality.

U.S. Pat. No. 10,764,079 for System and methods for correlating sleep data to security and/or automation system operations by inventors Mahar et al., filed Feb. 9, 2015 and issued Sep. 1, 2020, discloses a method for security and/or automation systems. In one embodiment, the method may include receiving input regarding at least one home automation system operation profile. The method may further include receiving monitored sleep data of at least one user of a home automation system associated with the at least one home automation system operation profile. The method may further include comparing the received monitored sleep data with the received input regarding the at least one home automation system operation profile, and may include implementing the at least one home automation system operation profile based, at least in part, on the comparing.

U.S. Pat. No. 11,134,888 for Systems and methods for smart home control by inventors Wright et al., filed Oct. 22, 2019 and issued Oct. 5, 2021, discloses a method for controlling one or more appliances in a user environment, the one or more appliances in operation capable of causing environmental stimuli disruptive to a user's sleep. The method comprises receiving from one or more sensors data indicative of a sleep state of the user; analysing the received data to determine one or more control actions for controlling the one or more appliances to reduce sleep disruption due to the environmental stimuli caused by the appliances; and controlling the one or more appliances in dependence on the determined control actions. The method may involve determining, based on sleep state data for a first sleep period, an appliance control schedule for a second, later, time period.

U.S. Patent Publication No. 2021/0314405 for Home automation having user privacy protections by inventors Demirli et al., filed Mar. 19, 2021 and published Oct. 7, 2021, discloses an acoustic sensor positioned in an environment and configured to generate a data stream responsive to acoustic energy in the environment. A controller is configured to receive the data stream. The controller is further configured to analyze the data stream to determine ambient acoustic signals. The controller is further configured to generate an ambient acoustic template based on the determined ambient acoustic signals. The controller is further configured to apply the ambient acoustic template to the data stream so that the ambient acoustic signals are suppressed in the data stream. The controller is further configured to analyze the data stream after the ambient acoustic signals are suppressed in order to determine if the acoustic energy in the environment includes acoustic energy of human snoring. The controller is further configured to issue a control signal to a second controller in order to engage a home automation device.

U.S. Patent Publication No. 2018/0082550 for Intelligent wake-up system by inventors Read et al., filed Sep. 16, 2016 and published Mar. 22, 2018, discloses a dynamic wake-up alarm, including a clock, a contactless biometric sensor, a processor, memory, and a speaker. The processor may be configured to receive a wake-up rule based on at least two wake-up criteria including a time from the clock and data from the biometric sensor, and evaluate whether the criteria are met to activate an alarm.

U.S. Patent Publication No. 2020/0100682 for System and Method for Determining a Sleep Onset, Sleep Arousal, and Sleep Awakening by inventors Abreu et al., filed Sep. 27, 2019 and published Apr. 2, 2020, discloses a sleep enhancement system for assisting, monitoring, informing, and improving sleep habits of a user. A utilized monitoring device gathers user's vital signs for transmission to a smart device while an environment sensor gathers information from the surroundings which is then sent to an environment transmitter. Signals from the smart device and environment transmitter are transmitted to a processor by wireless transmission such as by electromagnetic waves, radio waves, infrared, sound or by being reported by audio or visual transmission. Signals are stored for current or future commands to control the environment, smart devices, and appliances for a user. In addition to being able to control these, an input to the ABTT terminus, such as heat or cold, can be applied to encourage entry into sleep or wake from sleep, as well as release of supplements or drugs through a patch placed on the ABTT terminus or another bodily region.

U.S. Pat. No. 10,709,335 for Infant monitoring system with observation-based system control and feedback loops by inventors Matsuoka et al., filed Dec. 31, 2017 and issued Jul. 14, 2020, discloses a method of optimizing sleep of a subject using smart-home devices including operating a smart-home system that is configured to operate in a normal mode and a sleep mode. The method may also include determining that the smart-home system should transition into the sleep mode. The smart-home devices may use a set of default parameters when operating in the sleep mode. The method may additionally include monitoring, while in the sleep mode, a sleep cycle of the subject using the smart-home devices. The method may further include detecting behavior of the subject that indicates that the sleep cycle of the subject is being interrupted or about to be interrupted, determining an environmental control that corresponds with the behavior of the subject, and adjusting the environmental control using the smart-home devices to prevent or stop the sleep cycle of the subject from being interrupted.

U.S. Pat. No. 10,398,357 for Smart bed systems and methods of operation thereof by inventors Chen et al., filed Sep. 11, 2017 and issued Sep. 3, 2019, discloses smart bed systems and the operating methods of the smart bed systems. The smart bed systems detect physiological data and sleeping quality with optical fibers which with strong resistance to electromagnetic interference. The smart bed systems do not require the users to wear any wearable devices. The smart bed systems also provide several functions, such as automatic night light, vibration-based alarm, anti-snoring assistance, and scenario-based appliance controls.

U.S. Patent Publication No. 2020/0281521 for Apparatus, system, and method for monitoring sleep patterns by inventor Cail, filed Mar. 7, 2019 and published Sep. 10, 2020, discloses an assembly having a sleep pattern module, comprising computer-executable code stored in non-volatile memory, a processor, a sensor array, and a device array. The sleep pattern module, the processor, the sensor array, and the device array are configured to sense data of a sleep subject using the sensor array, process the sensed data, issue an alert to a guardian of the sleep subject based on the processed data, control the device array based on the processed data, and provide sleep pattern modification recommendations to the guardian of the sleep subject based on the processed data.

U.S. Pat. No. 10,179,064 for WhipFlash™: wearable environmental control system for predicting and cooling hot flashes by inventor Connor, filed May 5, 2015 and issued Jan. 15, 2019, discloses a sleep environment control system which uses wearable technology with physiological sensors to predict when a person will have a hot flash and to proactively provide localized cooling or accelerated airflow for that person for a limited time to alleviate the adverse effects of that hot flash. In an example, a physiological sensor can be a body temperature sensor, skin conductance sensor, or EEG sensor. This system can reduce interruptions of a person's sleep due to hot flashes and improve their quality of life.

U.S. Pat. No. 9,459,597 for Method and apparatus to provide an improved sleep experience by selecting an optimal next sleep state for a user by inventors Kahn et al., filed Feb. 28, 2013 and issued Oct. 4, 2016, discloses a sleep sensing system comprising a sensor to obtain real-time information about a user, a sleep state logic to determine the user's current sleep state based on the real-time information. The system further comprising a sleep stage selector to select an optimal next sleep state for the user, and a sound output system to output sounds to guide the user from the current sleep state to the optimal next sleep state.

U.S. Pat. No. 10,971,261 for Optimal sleep phase selection system by inventors Kahn et al., filed Oct. 3, 2016 and issued Apr. 6, 2021, discloses a sleep sensing system comprising a sensor to obtain real-time information about a user, a sleep state logic to determine the user's current sleep state based on the real-time information. The system further comprising a sleep stage selector to select an optimal next sleep state for the user, and a sound output system to output sounds to guide the user from the current sleep state to the optimal next sleep state.

U.S. Pat. No. 10,401,807 for Method for controlling nearby electronic device based on user status and electronic device thereof by inventors Jo et al., filed Nov. 25, 2015 and issued Sep. 3, 2019, discloses a method and an apparatus for operating an electronic device. A status of a user wearing the electronic device is determined using a sensor disposed in the electronic device. An operational status of a nearby electronic device is wirelessly controlled according to the status.

U.S. Patent Publication No. 2021/0267380 for Bed Having User Context Sensing Features by inventor Stusynski, filed Mar. 2, 2021 and published Sep. 2, 2021, discloses a system including a bed having a mattress. The system further includes a sensor configured to generate pressure data of the mattress. The system further includes a processor device configured to receive the pressure data; and determine a user state from at least the pressure data. The system further includes a user-interface device comprising user-interface hardware that is capable of providing user interfaces, the user-interface device configured to select, from a plurality of available user interfaces, a selected user interface; and providing the selected user interface to a user. Other systems, methods, devices, products, and software may be used.

U.S. Pat. No. 5,304,112 for stress reduction system and method by inventors Mrklas et al., filed Oct. 16, 1991 and issued Apr. 19, 1994, discloses an integrated stress reduction system that detects the stress level of a subject and displays a light pattern reflecting the relationship between the subject's stress level and a target level. At the same time, the system provides relaxing visual, sound, tactile, environmental, and other effects to aid the subject in reducing his or her stress level to the target level. In one preferred embodiment, the intensity, type, and duration of the relaxing effects are controlled by a computer program in response to the measured stress level. The light pattern stress level display uses a laser which is deflected on one axis by a measured stress level signal and on a second axis perpendicular to the first by a target signal representing the target stress level. The pattern produced is more complex when the two signals do not coincide, and becomes a less complex geometric figure as the subject's stress level approaches the target.

U.S. Pat. No. 6,484,062 for computer system for stress relaxation and operating method of the same by inventor Kim, filed Nov. 30, 1999 and issued Nov. 19, 2002, discloses a computer system provided to relax stresses such as fatigue, VDT syndrome, occupational diseases or psychogenic possibly gained from long hours of computer usage. This new computer system is able to divert the negative effects of conventional computer to affirmative effects by introducing the aroma therapy. The new computer system provides not only the data programs of establishing, playing execution and controlling, but also the stress relief program comprising acoustic therapy, color therapy, fragrance therapy and tactual therapy and a stress perception program. The stress relief program is operated by an emission device through a converter. The equipment of the stress relief is installed on a peripheral device of computer such as a speaker, keyboard or monitor. The new concept of computer system for stress relaxation originates a combination of the computer system and the natural therapies applied the human senses like sight, hearing, feeling and smelling senses. With this new computer system, the computer user has a merit of stress relief during the computer operating.

U.S. Patent Publication No. 2004/0049132 for device for body activity detection and processing by inventors Barron et al., filed Dec. 9, 2002 and published Mar. 11, 2004, discloses a method and device for monitoring a body activity. The device has an actimetry sensor for measuring the activity and storage means for receiving data from the actimetry sensor. The data are analysed according to a method using summation algorithm, where a plurality of parameters relating to the activity are summed to provide advisory information relating to that activity. The analysis may include pre-programmed biasing constants or user supplied biasing constants.

U.S. Pat. No. 7,460,899 for apparatus and method for monitoring heart rate variability by inventor Almen, filed Feb. 25, 2005 and issued Dec. 2, 2008, discloses a wrist-worn or arm band worn heart rate variability monitor. Heart rate variability ("HRV") refers to the variability of the time interval between heartbeats and is a reflection of an individual's current health status. Over time, an individual may use the results of HRV tests to monitor either improvement or deterioration of specific health issues. Thus, one use of the HRV test is as a medical motivator. When an individual has a poor HRV result, it is an indicator that they should consult their physician and make appropriate changes where applicable to improve their health. If an individual's HRV results deviate significantly from their normal HRV, they may be motivated to consult their physician. In addition, the inventive monitor is capable of monitoring the stages of sleep by changes in the heart rate variability and can record the sleep (or rest) sessions with the resulting data accessible by the user or other interested parties. Alternate embodiments of the invention allow assistance in the diagnosis and monitoring of various cardiovascular and sleep breathing disorders and/or conditions. Other embodiments allow communication with internal devices such as defibrillators or drug delivery mechanisms. Still other embodiments analyze HRV data to assist the user in avoiding sleep.

U.S. Pat. No. 7,524,279 for sleep and environment control method and system by inventor Auphan, filed Dec. 29, 2004 and issued Apr. 28, 2009, discloses a sleep system that includes sensors capable of gathering sleep data from a person and environmental data during a sleep by the person. A processor executes instructions that analyze this data and control the sleep of the person and the environment surrounding the person. Typically, the instructions are loaded in a memory where they execute to generate an objective measure of sleep quality from the sleep data from the person and gather environmental data during the sleep by the person. Upon execution, the instructions receive a subjective measure of sleep quality from the person after the sleep, create a sleep quality index from the objective measure of sleep quality and subjective measure of sleep quality, correlate the sleep quality index and a current sleep system settings with a historical sleep quality index and corresponding historical sleep system settings. The instructions then may modify the current set of sleep system settings depending on the correlation between the sleep quality index and the historic sleep quality index. These sleep system settings control and potentially change one or more different elements of an environment associated with the sleep system.

U.S. Pat. No. 7,699,785 for method for determining sleep stages by inventor Nemoto, filed Feb. 23, 2005 and issued Apr. 20, 2010, discloses a method for determining sleep stages of an examinee, including detecting signals of the examinee with a biosignal detector, calculating a signal strength deviation value that indicates deviation of a signal strength of the detected signals, and determining a sleep stage by using the signal strength deviation value or a value of a plurality of values based on the signal strength deviation value as an indicator value.

U.S. Patent Publication No. 2010/0100004 for skin temperature measurement in monitoring and control of sleep and alertness by inventor van Someren, filed Dec. 15, 2008 and published Apr. 22, 2010, discloses a method of an arrangement for monitoring sleep in a subject by measuring within a prescribed interval skin temperature of a predetermined region of the subject's body and a motion sensor for sensing motion of the subject, comparing the measured skin temperature of the predetermined region with a predetermined temperature threshold, and classifying the subject as being asleep or awake based on whether the skin temperature of the predetermined region is above or below the temperature threshold and on the motion data. In alternative aspects the invention relates to methods of and arrangements for manipulating sleep, as well as monitoring or manipulating alertness.

U.S. Pat. No. 7,868,757 for method for the monitoring of sleep using an electronic device by inventors Radivojevic et al., filed Dec. 29, 2006 and issued Jan. 11, 2011, discloses a method where sleep sensor signals are obtained to a mobile communication device from sensor devices. The mobile communication device checks the sleep sensor signals for a sleep state transition, determines the type of the sleep state transition, forms control signals based on the type of the sleep state transition and sends the control signals to at least one electronic device.

U.S. Patent Publication No. 2011/0015495 for method and system for managing a user's sleep by inventors Dothie et al., filed Jul. 16, 2010 and published Jan. 20, 2011, discloses a sleep management method and system for improving the quality of sleep of a user which monitors one or more objective parameters relevant to sleep quality of the user when in bed and receives from the user in waking hours via a portable device such as a mobile phone feedback from objective test data on cognitive and/or psychomotor performance.

U.S. Patent Publication No. 2011/0267196 for system and method for providing sleep quality feedback by inventors Hu et al., filed May 3, 2011 and published Nov. 3, 2011, discloses a system and method for providing sleep quality feedback that includes receiving alarm input on a base device from a user; the base device communicating an alarm setting based on the alarm input to an individual sleep device; the individual sleep device collecting sleep data based on activity input of a user; the individual sleep device communicating sleep data to the base device; the base device calculating sleep quality feedback from the sleep data; communicating sleep quality feedback to a user; and the individual sleep device activating an alarm, wherein activating the alarm includes generating tactile feedback to the user according to the alarm setting.

U.S. Pat. No. 8,290,596 for therapy program selection based on patient state by inventors Wei et al., filed Sep. 25, 2008 and issued Oct. 16, 2012, discloses selecting a therapy program based on a patient state, where the patient state comprises at least one of a movement state, sleep state or speech state. In this way, therapy delivery is tailored to the patient state, which may include specific patient symptoms. The therapy program is selected from a plurality of stored therapy programs that comprise therapy programs associated with a respective one at least two of the movement, sleep, and speech states. Techniques for determining a patient state include receiving volitional patient input or detecting biosignals generated within the patient's brain. The biosignals are nonsymptomatic and may be incidental to the movement, sleep, and speech states or generated in response to volitional patient input.

U.S. Pat. No. 8,348,840 for device and method to monitor, assess and improve quality of sleep by inventors Heit et al., filed Feb. 4, 2010 and issued Jan. 8, 2013, discloses a medical sleep disorder arrangement that integrates into current diagnosis and treatment procedures to enable a health care professional to diagnose and treat a plurality of subjects suffering from insomnia. The arrangement may include both environmental sensors and body-worn sensors that measure the environmental conditions and the condition of the individual patient. The data may be collected and processed to measure clinically relevant attributes of sleep quality automatically. These automatically determined measures, along with the original sensor data, may be aggregated and shared remotely with the health care professional. A communication apparatus enables the healthcare professional to remotely communicate with and further assess the patient and subsequently administer the treatment. Thus, a more accurate diagnosis and more effective treatment is provided while reducing the required clinician time per patient for treatment delivery.

U.S. Pat. No. 8,529,457 for system and kit for stress and relaxation management by inventors Devot et al., filed Feb. 16, 2009 and issued Sep. 10, 2013, discloses a system and a kit for stress and relaxation management. A cardiac activity sensor is used for measuring the heart rate variability (HRV) signal of the user and a respiration sensor for measuring the respiratory signal of the user. The system contains a user interaction device having an input unit for receiving user specific data and an output unit for providing information output to the user. A processor is used to assess the stress level of the user by determining a user related stress index. The processor is also used to monitor the user during a relaxation exercise by means of determining a relaxation index based on the measured HRV and respiratory signals, the relaxation index being continuously adapted to the incoming measured signals and based thereon the processor instructs the output unit to provide the user with biofeedback and support messages. Finally, the processor uses the user specific data as an input in generating a first set of rules defining an improvement plan for self-management of stress and relaxation. The first set of rules is adapted to trigger commands instructing the output unit to provide the user with motivation related messages. Also, at least a portion of said user specific data is further used to define a second set of rules indicating the user's personal goals.

U.S. Pat. No. 8,617,044 for stress reduction by inventors Pelgrim et al., filed Dec. 5, 2007 and issued Dec. 31, 2013, discloses a method and system for reducing stress in a working environment. In a conditioning phase a positive association of a sensory stimulus, such as a scent, image and/or sound with a relaxed feeling is created. Following the creation of this positive association the "relaxing" stimulus will be used as a de-stressor in the usage phase. That is, when it is detected that the user is stressed, the "relaxing" stimulus is released to reduce stress.

U.S. Pat. No. 8,979,730 for method and system for providing behavioural therapy for insomnia by inventors Naujokat et al., filed Jun. 1, 2010 and issued Mar. 17, 2015, discloses a system and method to provide for the automatic assessment of the presence/severity of the sleep problem and its exact nature. The assessment is based on qualitative information about sleep patterns, insomnia-related factors and daytime consequences, as well as quantitative information about sleep patterns measured by a sensor. By combining the different sources of information (subjective as well as objective data), the diagnosis gives more insight into the nature of the sleep problem and is therefore more accurate. Furthermore, the disclosed system may be used to select specific components of the system that are medically relevant to the individual and therefore create a personalized program. The system teaches a selection of self-management skills that could help the individual to better cope with sleep disturbances and target those factors that maintain the problem or make it worse by a particular individual.

U.S. Patent Publication No. 2015/0257697 for method and system for mobile, social, behavioral treatment of sleep by inventor Sepah, filed Mar. 17, 2014 and published Sep. 17, 2015, discloses a method and system for mobile behavioral treatment of sleep issues such as insomnia comprising of: placing, participants into an online software platform that includes an online coach and group/community to reinforce compliance and provide social support; providing, a curriculum, compromising of modules of evidence-based behavioral treatments (e.g. cognitive-behavioral therapy (CBT), intensive sleep retraining (ISR)); providing, a wireless wearable body metric measurement device configured to communicate remotely with a mobile computing device and network; receiving a set of body metric measurement data via a mobile computing device; transmitting and storing the body metric measurement data on a server; determining trends and changes in the body metric measurement of the participant; providing, visual feedback regarding sleep quantity and quality to the participant via an online software platform that is accessible through mobile devices; calculating individualized recommendations based on body metric measurements and CBT protocols; providing, behavioral alerts to the participant via a wireless body metric device to alter sleep behaviors.

U.S. Patent Publication No. 2016/0151603 for methods and systems for sleep management by inventors Shouldice et al., filed Jul. 8, 2014 and published Jun. 2, 2016, discloses a processing system including methods to promote sleep. The system may include a monitor such as a non-contact motion sensor from which sleep information may be determined. User sleep information, such as sleep stages, hypnograms, sleep scores, mind recharge scores and body scores, may be recorded, evaluated and/or displayed for a user. The system may further monitor ambient and/or environmental conditions corresponding to sleep sessions. Sleep advice may be generated based on the sleep information, user queries and/or environmental conditions from one or more sleep sessions. Communicated sleep advice may include content to promote good sleep habits and/or detect risky sleep conditions. In some versions of the system, any one or more of a bedside unit sensor module, a smart processing device, such as a smart phone or smart device, and network servers may be implemented to perform the methodologies of the system.

U.S. Patent Publication No. 2017/0017759 for cognitive behavioral therapy (CBT) method, system and application by inventors MacNeice et al., filed Jul. 18, 2016 and published Jan. 19, 2017, discloses a cognitive behavioral therapy (CBT) method, system and application for treating disorders/conditions such as e.g., insomnia, smoking cessation, alcohol addiction, depression, and nightmares, among others.

U.S. Patent Publication No. 2017/0053068 for methods for enhancing wellness associated with habitable environments by inventors Pillai et al., filed Aug. 26, 2016 and published Feb. 23, 2017, discloses controlling environmental characteristics of habitable environments (e.g., hotel or motel rooms, spas, resorts, cruise boat cabins, offices, hospitals and/or homes, apartments or residences) to eliminate, reduce or ameliorate adverse or harmful aspects and introduce, increase or enhance beneficial aspects in order to improve a "wellness" or sense of "wellbeing" provided via the environments. Control of intensity and wavelength distribution of passive and active illumination addresses various issues, symptoms or syndromes, for instance to maintain a circadian rhythm or cycle, adjust for "jet lag" or season affective disorder, etc. Air quality and attributes are controlled. Scent(s) may be dispersed. Noise is reduced and sounds (e.g., masking, music, natural) may be provided. Environmental and biometric feedback is provided. Experimentation and machine learning are used to improve health outcomes and wellness standards.

U.S. Patent Publication No. 2017/0189641 for method and system for characterizing and/or treating poor sleep behavior by inventors Moturu et al., filed Mar. 21, 2017 and published Jul. 6, 2017, discloses a method and system for improving sleep characterization and/or a sleeping-related disorder for a user associated with a sleep session that can include receiving a log of use dataset corresponding to user digital communication behavior at a mobile device, the log of use dataset associated with the sleep session; receiving a supplementary dataset characterizing activity of the user and/or mobile device, the supplementary dataset associated with the sleep session; characterizing a sleep-related parameter for the user based on at least one of the log of use dataset and the supplementary dataset; determining a sleep care plan for the user based on the sleep-related parameter, the sleep care plan including a therapeutic intervention; and promoting a therapeutic intervention to the user according to the sleep care plan.

U.S. Pat. No. 9,999,744 for monitoring device and cognitive behavior therapy by inventor Proud, filed Jun. 28, 2016 and issued Jun. 19, 2018, discloses a user monitoring device system including a user monitoring device with a microphone and sensors to determine air quality, sound level/quality, light quality and ambient temperature near the user. A movement detection device detects a user's movement information. The movement detection device and the monitoring system assist to determine user sleep information and sleep behavior information. The microphone records user movement sounds detected by the movement detection device. The movement detection device is configured to cause the microphone to stop recording user movement sounds when the movement sounds are not directed to a sleep related parameter. In response to determining user sleep information or sleep behavior information the system is used for treatment of sleep or psychiatric disorders.

U.S. Patent Publication No. 2018/0226155 for methods and systems for cognitive behavioral therapy by inventors Mahoney et al., filed Feb. 2, 2018 and published Aug. 9, 2018, discloses methods and systems for cognitive behavioral therapy. A first set of data and a second set of data related to a health attribute are received, over a first time period. The first and second sets of data are displayed in a first and a second graphical item. A graphical button is displayed on the first graphical item and configured to move it on a display. Using the graphical button, the first graphical item is, at least partially, overlaid upon the second graphical item. In response to the overlaying a third set of data is generated and displayed in a third graphical item. The third set of data is at least partially based on associating the first set of data with the second set of data using one or more sets of rules that establish the relationship between the first set of data and the second set of data.

U.S. Patent Publication No. 2018/0260387 for systems and methods for dynamic user interaction for improving happiness by inventors Ben-Kiki et al., filed May 9, 2018 and published Sep. 13, 2018, discloses a computing system for interacting with a user comprises a processor and a memory storing executable software which, when executed by the processor, causes the processor to commence an interactive session with a user, receive input data from the user during the interactive session, analyze the received input data and output a response to the user to continue the interactive session with the user. The processor, prior to outputting the response, identifies one or more topics from the received input data, ascertains a tone of the received input data, generates a mirroring prompt based on the ascertained tone of the received input data, and output to the user the generated mirroring prompt. The processor outputs the mirroring prompt to the user during the interactive session to cause an increase in a level of engagement of the user with the interactive session.

U.S. Patent Publication No. 2018/0285528 for sensor assisted mental health therapy by inventors Healey et al., filed Mar. 30, 2017 and published Oct. 4, 2018, discloses computer systems to allow users to record sensor readings of their environment and correlate these sensor readings with mental health events for later analysis to improve mental health diagnoses and treatments. A monitoring system comprising a computing device and a sensor set (comprising one or more sensors integral to or communicatively coupled to the computing device) may collect and store data collected about the user. This data may be stored in the computing device, or may be stored in a cloud based data-storage service. This data may be annotated or correlated (either manually, or automatically) with mental health events of the user and used for later analysis.

SUMMARY OF THE INVENTION

The present invention relates to articles, methods, and systems for stress reduction and sleep promotion.

In one embodiment, the present invention provides a system to reduce stress and promote sleep including at least one remote device in communication with at least one body sensor, wherein the at least one body sensor includes at least one article temperature sensor, at least one environmental temperature sensor and at least one pressure sensor, wherein the at least one remote device collects body sensor data from the at least one body sensor, wherein the at least one remote device is operable to analyze the body sensor data, thereby creating analyzed body sensor data, wherein the analyzed body sensor data includes at least a heart rate, a respiration rate, and a bed status for a user, wherein the at least one remote device classifies the user into at least one group based on a user profile, the body sensor data, and/or user provided information, and wherein the at least one remote device provides at least one sleep report, including a sleep score for the user.

In another embodiment, the present invention provides a system to reduce stress and promote sleep including at least one remote device in communication with at least one body sensor, wherein the at least one body sensor includes at least one article temperature sensor, at least one environmental temperature sensor and at least one pressure sensor, wherein the at least one remote device collects body sensor data from the at least one body sensor, wherein the at least one remote device is operable to analyze the body sensor data, thereby creating analyzed body sensor data, wherein the at least one remote device is operable to aggregate a plurality of the at least one body sensor into one or more collections based on preferences in a user profile, and wherein the body sensor data from each of the one or more collections is analyzed separately, wherein the at least one remote device classifies a user into at least one group based on the user profile, the body sensor data, and/or user provided information, and wherein the at least one remote device provides at least one sleep report, including a sleep score for the user.

In yet another embodiment, the present invention provides a system to reduce stress and promote sleep including at least one remote device in communication with at least one body sensor, and a mattress pad, a blanket, and/or a mattress with adjustable surface temperature, wherein the at least one body sensor includes at least one article temperature sensor, at least one environmental temperature sensor and at least one pressure sensor, wherein one or more of the at least one body sensor is embedded in the mattress pad, the blanket, and/or the mattress with adjustable surface temperature, wherein the at least one remote device collects body sensor data from the at least one body sensor, wherein the at least one remote device is operable to analyze the body sensor data, thereby creating analyzed body sensor data, wherein the at least one remote device classifies a user into at least one group based on a user profile, the body sensor data, and/or user provided information, and wherein the at least one remote device provides at least one sleep report, including a sleep score for the user.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 37 illustrates an example of a sleep commitment screen where an additional 50 seconds are added per day based on the user's commitments.

FIG. 38 illustrates an example of a sleep commitment screen describing the benefits of using the sleep tracker.

FIG. 66 illustrates an example of a chronotype self-assessment quiz.

FIG. 69 shows a table with an example of connections for users.

FIG. 79 illustrates yet another profile screen for one embodiment of a GUI for a mobile application.

FIG. 82 illustrates a profile screen for one embodiment of a GUI for a mobile application allowing for segmented sleep.

FIG. 84 illustrates a treatment summary screen for one embodiment of a GUI for a mobile application.

DETAILED DESCRIPTION

Figure 1:
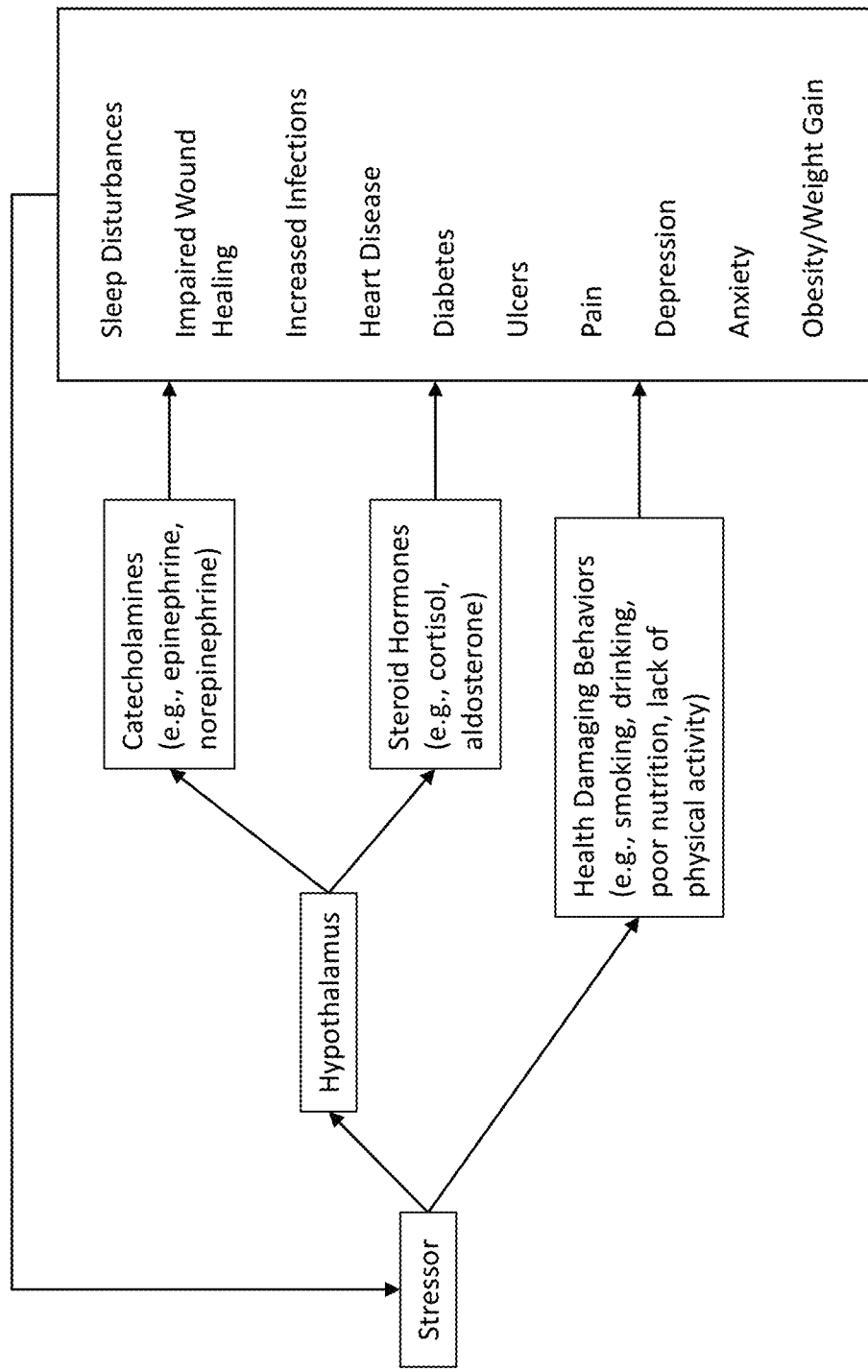
FIG. 1 illustrates the effects of a stressor on the body.

The present invention is generally directed to articles, methods, and systems for stress reduction and sleep promotion.

In one embodiment, the present invention provides a system to reduce stress and promote sleep including at least one remote device in communication with at least one body sensor, wherein the at least one body sensor includes at least one article temperature sensor, at least one environmental temperature sensor and at least one pressure sensor, wherein the at least one remote device collects body sensor data from the at least one body sensor, wherein the at least one remote device is operable to analyze the body sensor data, thereby creating analyzed body sensor data, wherein the analyzed body sensor data includes at least a heart rate, a respiration rate, and a bed status for a user, wherein the at least one remote device classifies the user into at least one group based on a user profile, the body sensor data, and/or user provided information, and wherein the at least one remote device provides at least one sleep report, including a sleep score for the user.

In another embodiment, the present invention provides a system to reduce stress and promote sleep including at least one remote device in communication with at least one body sensor, wherein the at least one body sensor includes at least one article temperature sensor, at least one environmental temperature sensor and at least one pressure sensor, wherein the at least one remote device collects body sensor data from the at least one body sensor, wherein the at least one remote device is operable to analyze the body sensor data, thereby creating analyzed body sensor data, wherein the at least one remote device is operable to aggregate a plurality of the at least one body sensor into one or more collections based on preferences in a user profile, and wherein the body sensor data from each of the one or more collections is analyzed separately, wherein the at least one remote device classifies a user into at least one group based on the user profile, the body sensor data, and/or user provided information, and wherein the at least one remote device provides at least one sleep report, including a sleep score for the user.

In yet another embodiment, the present invention provides a system to reduce stress and promote sleep including at least one remote device in communication with at least one body sensor, and a mattress pad, a blanket, and/or a mattress with adjustable surface temperature, wherein the at least one body sensor includes at least one article temperature sensor, at least one environmental temperature sensor and at least one pressure sensor, wherein one or more of the at least one body sensor is embedded in the mattress pad, the blanket, and/or the mattress with adjustable surface temperature, wherein the at least one remote device collects body sensor data from the at least one body sensor, wherein the at least one remote device is operable to analyze the body sensor data, thereby creating analyzed body sensor data, wherein the at least one remote device classifies a user into at least one group based on a user profile, the body sensor data, and/or user provided information, and wherein the at least one remote device provides at least one sleep report, including a sleep score for the user.

Several studies show a link between stress and illness. Stress often causes physiological changes and leads individuals to adopt health damaging behaviors (e.g., smoking, drinking, poor nutrition, lack of physical activity). These physiological changes and health damaging behaviors often cause illnesses, such as sleep disturbances, impaired wound healing, increased infections, heart disease, diabetes, ulcers, pain, depression, and obesity or weight gain.

The body reacts to stress through two systems: the autonomic nervous system and the hypothalamic-pituitary-adrenal (RPA) axis. The autonomic nervous system, which consists of the sympathetic nervous system and the parasympathetic nervous system, is responsible for reacting to short term ("acute") stress. In response to short term stress, the sympathetic nervous system activates the "fight or flight response" through the sympathoadrenal medullary (SAM) axis. This causes the adrenal medulla to secrete catecholamines (e.g., epinephrine and norepinephrine), which causes blood glucose levels to rise, blood vessels to constrict, heart rate to increase, and blood pressure to rise. Blood is diverted from nonessential organs to the heart and skeletal muscles, which leads to decreased digestive system activity and reduced urine output. Additionally, the metabolic rate increases and bronchioles dilate. The parasympathetic nervous system then returns the body to homeostasis.

The HPA axis is responsible for reacting to long term ("chronic") stress. This causes the adrenal cortex to secrete steroid hormones (e.g., mineralocorticoids and glucocorticoids). Mineralocorticoids (e.g., aldosterone) cause retention of sodium and water by the kidneys, increased blood pressure, and increased blood volume. Glucocorticoids (e.g., cortisol) cause proteins and fats to be converted to glucose or broken down for energy, increased blood glucose, and suppression of the immune system.

Thus, stress impacts the body on a cellular level and is a precursor to many disease states. Therefore, it is important to manage and treat stress to maintain health. However, as a result of modern lifestyles, most people are busy, tired, and stressed out. Most people also lack the time and energy to obtain treatments for minor ailments or treatments to prevent disease. What is needed is a convenient treatment that reduces stress and inflammation and promotes healing.

Energy medicine (e.g., biofield therapies, bioelectromagnetic therapies, acupuncture, homeopathy) focuses on the principle that small changes repeated over time change the dynamics of the body and stimulate healing. The present invention utilizes that principle to reduce stress, promote sleep, and stimulate healing. Further, the present invention reduces stress and stimulates healing in small increments throughout the day and by encouraging more restful sleep at night, which are both convenient for the user.

Referring now to the drawings in general, the illustrations are for the purpose of describing a preferred embodiment of the invention and are not intended to limit the invention thereto.

FIG. 1 illustrates the effects of a stressor on the body. The body releases catecholamines or steroid hormones as a physiological response to the stressor. Stress also leads individuals to adopt health damaging behaviors (e.g., smoking, drinking, poor nutrition, lack of physical activity). This sometimes leads to illnesses, such as sleep disturbances, impaired wound healing, increased infections, heart disease, diabetes, ulcers, pain, depression, anxiety, and/or obesity or weight gain. These illnesses themselves also often become stressors, which triggers the cycle to continue and causes further physical and mental problems.

Figure 2:
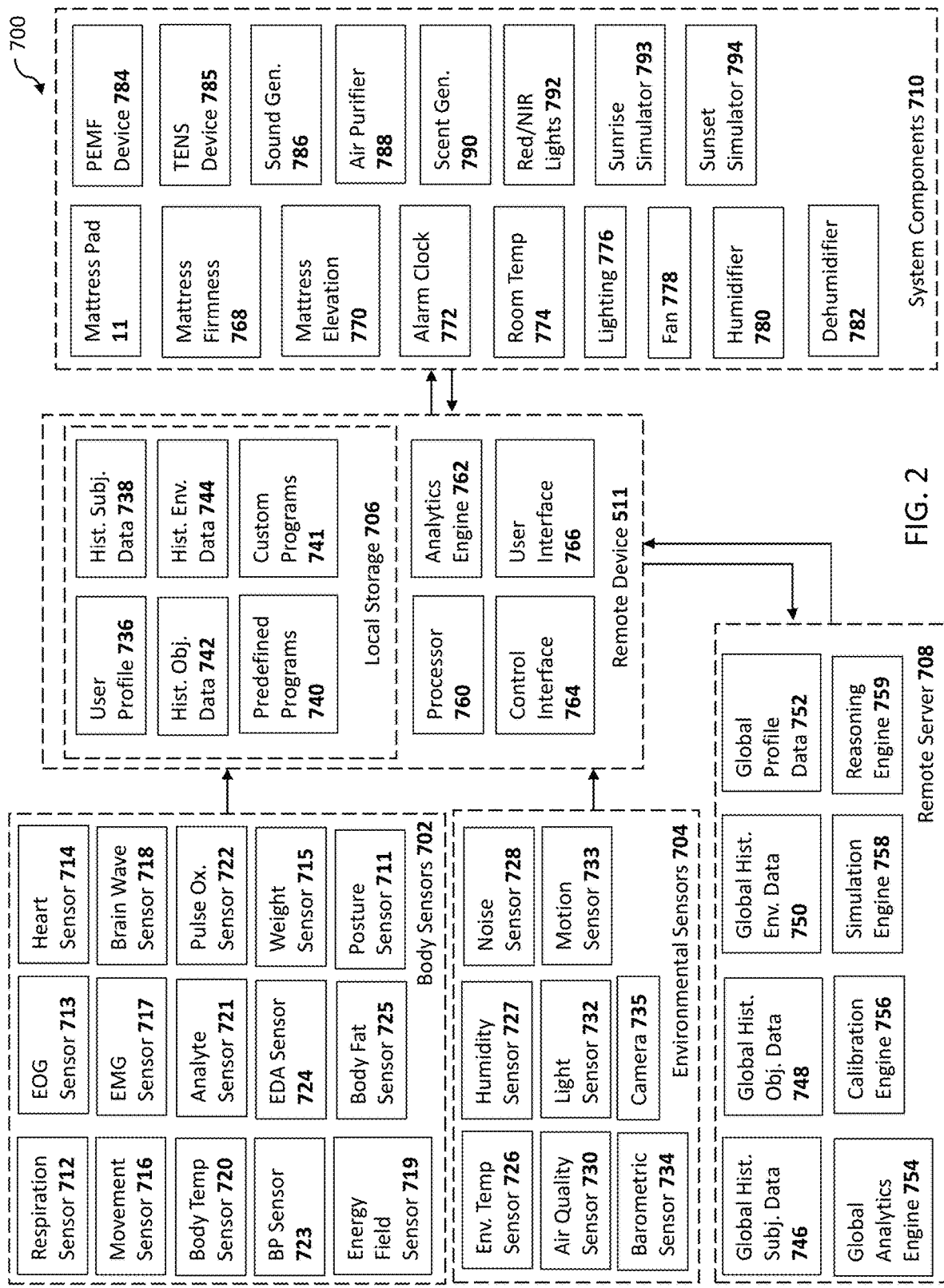
FIG. 2 is a block diagram of one embodiment of the stress reduction and sleep promotion system.

FIG. 2 is a block diagram of one embodiment of a stress reduction and sleep promotion system. The stress reduction and sleep promotion system 700 includes body sensors 702, environmental sensors 704, a remote device 511 with local storage 706, a remote server 708, and system components 710. The body sensors 702 include a posture sensor 711, a respiration sensor 712, an electrooculography (EOG) sensor 713, a heart rate sensor 714, a body weight sensor 715, a movement sensor 716, an electromyography (EMG) sensor 717, a brain wave sensor 718, a body temperature sensor 720, an analyte sensor 721, a pulse oximeter sensor 722, a blood pressure (BP) sensor 723, an electrodermal activity (EDA) sensor 724, and/or a body fat sensor 725. In one embodiment, at least one body sensor 702 is implanted in the body of a user. In a preferred embodiment, at least one body sensor 702 is operable to transmit data to the remote device 511 and/or the remote server 708 in real time.

The posture sensor 711 measures a posture of an individual. In one embodiment, the posture sensor 711 includes at least one pressure sensor. The at least one pressure sensor is preferably embedded in a seat and/or seat cushion (e.g., DARMA, SENSIMAT). In another embodiment, the posture sensor 711 is a wearable device (e.g., LUMOback Posture Sensor). In another embodiment, the posture sensor 711 includes at least one camera. The at least one camera is operable to detect a posture of the individual using, e.g., computer vision.

The respiration sensor 712 measures a respiratory rate. In one embodiment, the respiration sensor 712 is incorporated into a wearable device (e.g., a chest strap). In another embodiment, the respiration sensor 712 is incorporated into a patch or a bandage. Alternatively, the respiratory rate is estimated from an electrocardiogram, a photoplethysmogram (e.g., a pulse oximeter), and/or an accelerometer. In yet another embodiment, the respiratory sensor 712 uses a non-contact motion sensor to monitor respiration.

The electrooculography (EOG) sensor 713 measures the corneo-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position.

The heart sensor 714 is preferably incorporated into a wearable device (e.g., APPLE WATCH, FITBIT, SAMSUNG GALAXY WATCH). Alternatively, the heart sensor 714 is attached to the user with a chest strap. In another embodiment, the heart sensor 714 is incorporated into a patch or a bandage. In yet another embodiment, the heart sensor 714 is incorporated into a sensor device on or under the mattress (e.g., BEDDIT, EMFIT QS). Alternatively, the heart sensor 714 is embedded in the mattress. A heart rate is determined using electrocardiography, pulse oximetry, ballistocardiography, or seismocardiography. In one embodiment, the heart sensor 714 measures heart rate variability (HRV). HRV is a measurement of the variation in time intervals between heartbeats. A high HRV measurement is indicative of less stress, while a low HRV measurement is indicative of more stress. Studies have linked abnormalities in HRV to diseases where stress is a factor (e.g., diabetes, depression, congestive heart failure). In one embodiment, a Poincare plot is generated to display HRV on a device such as a smartphone. In another embodiment, the heart sensor 714 is an electrocardiogram.

The body weight sensor 715 is preferably a smart scale (e.g., FITBIT ARIA, WITHINGS BODY+, GARMIN INDEX, PIVOTAL LIVING SMART SCALE, IHEALTH CORE). Alternatively, the body weight sensor 715 is at least one pressure sensor embedded in a mattress or a mattress topper. In one embodiment, the stress reduction and sleep promotion system 700 is also operable to determine a height of a user using the at least one pressure sensor embedded in a mattress or a mattress topper. In another embodiment, a body mass index (BMI) of the user is calculated using the body weight of the user and the height of the user as measured by the at least one pressure sensor.

The movement sensor 716 is an accelerometer and/or a gyroscope. In one embodiment, the accelerometer and/or the gyroscope are incorporated into a wearable device (e.g., FITBIT, APPLE WATCH, SAMSUNG GALAXY WATCH, actigraph). In another embodiment, the accelerometer and/or the gyroscope are incorporated into a smartphone. In alternative embodiment, the movement sensor 716 is a non-contact sensor. In one embodiment, the movement sensor

716 is at least one piezoelectric sensor. In another embodiment, the movement sensor 716 is a pyroelectric infrared sensor (i.e., a "passive" infrared sensor). In yet another embodiment, the movement sensor 716 is at least one pressure sensor embedded in a mattress or mattress topper. Alternatively, the movement sensor 716 is incorporated into a smart fabric. In still another embodiment, the movement sensor 716 is operable to analyze a gait of a user.

The electromyography (EMG) sensor 717 records the electrical activity produced by skeletal muscles. Impulses are recorded by attaching electrodes to the skin surface over the muscle. In a preferred embodiment, three electrodes are placed on the chin. One in the front and center and the other two underneath and on the jawbone. These electrodes demonstrate muscle movement during sleep, which is able to be used to detect REM or NREM sleep. In another embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg are able to be used to detect movement of the legs during sleep, which often occurs with Restless Leg Syndrome or Periodic Limb Movements of Sleep.

The brain wave sensor 718 is preferably an electroencephalogram (EEG) with at least one channel. In a preferred embodiment, the EEG has at least two channels. Multiple channels provide higher resolution data. The frequencies in EEG data indicate particular brain states. The brain wave sensor 718 is preferably operable to detect delta, theta, alpha, beta, and gamma frequencies. In another embodiment, the brain wave sensor 718 is operable to identify cognitive and emotion metrics, including focus, stress, excitement, relaxation, interest, and/or engagement. In yet another embodiment, the brain wave sensor 718 is operable to identify cognitive states that reflect the overall level of engagement, attention and focus and/or workload that reflects cognitive processes (e.g., working memory, problem solving, analytical reasoning).

The energy field sensor 719 measures an energy field of a user. In one embodiment, the energy field sensor 719 is a gas discharge visualization (GDV) device. Examples of a GDV device are disclosed in U.S. Pat. Nos. 7,869,636 and 8,321,010 and U.S. Patent Publication No. 2010/0106424, each of which is incorporated herein by reference in its entirety. The GDV device utilizes the Kirlian effect to evaluate an energy field. In a preferred embodiment, the GDV device utilizes a high-intensity electric field (e.g., 1024 Hz, 10 kV, square pulses) input to an object (e.g., human fingertips) on an electrified glass plate. The high-intensity electric field produces a visible gas discharge glow around the object (e.g., fingertip). The visible gas discharge glow is detected by a charge-coupled detector and analyzed by software on a computer. The software characterizes the pattern of light emitted (e.g., brightness, total area, fractality, density). In a preferred embodiment, the software utilizes Mandel's Energy Emission Analysis and the Su-Jok system of acupuncture to create images and representations of body systems. The energy field sensor 719 is preferably operable to measure stress levels, energy levels, and/or a balance between the left and right sides of the body.

The body temperature sensor 720 measures core body temperature and/or skin temperature. The body temperature sensor 720 is a thermistor, an infrared sensor, or thermal flux sensor. In one embodiment, the body temperature sensor 720 is incorporated into a ring, an armband, or a wristband. In another embodiment, the body temperature sensor 720 is incorporated into a patch or a bandage. In yet another embodiment, the body temperature sensor 720 is an ingestible core body temperature sensor (e.g., CORTEMP). The body temperature sensor 720 is preferably wireless.

The analyte sensor 721 monitors levels of an analyte in blood, sweat, tears, saliva, or interstitial fluid. Alternatively, the analyte sensor 721 monitors levels of an analyte in lymph, urine, or breath (i.e., breathalyzer). In one embodiment, the analyte is an electrolyte, a small molecule (molecular weight <900 Daltons), a protein (e.g., C-reactive protein), and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). The analyte sensor 721 is preferably non-invasive. Alternatively, the analyte sensor 721 is minimally invasive or implanted. In one embodiment, the analyte sensor 721 is incorporated into a wearable device. Alternatively, the analyte sensor 721 is incorporated into a patch or a bandage.

The pulse oximeter sensor 722 monitors oxygen saturation. In one embodiment, the pulse oximeter sensor 722 is worn on a finger, a toe, or an ear. In another embodiment, the pulse oximeter sensor 722 is incorporated into a patch or a bandage. The pulse oximeter sensor 722 is preferably wireless. Alternatively, the pulse oximeter sensor 722 is wired. In one embodiment, the pulse oximeter sensor 722 is connected by a wire to a wrist strap or a strap around a hand. In another embodiment, the pulse oximeter sensor 722 is combined with a heart rate sensor 714. In yet another embodiment, the pulse oximeter sensor 722 uses a camera lens on a smartphone or a tablet.

The blood pressure (BP) sensor 723 is a sphygmomanometer. The sphygmomanometer is preferably wireless. Alternatively, the blood pressure sensor 723 estimates the blood pressure without an inflatable cuff (e.g., SALU PULSE+). In one embodiment, the blood pressure sensor 723 is incorporated into a wearable device.

The electrodermal activity sensor 724 measures sympathetic nervous system activity. Electrodermal activity is more likely to have high frequency peak patterns (i.e., "storms") during deep sleep. In one embodiment, the electrodermal activity sensor 724 is incorporated into a wearable device. Alternatively, the electrodermal activity sensor 724 is incorporated into a patch or a bandage.

The body fat sensor 725 is preferably a bioelectrical impedance device. In one embodiment, the body fat sensor 725 is incorporated into a smart scale (e.g., FITBIT ARIA, WITHINGS BODY+, GARMIN INDEX, PIVOTAL LIVING SMART SCALE, IHEALTH CORE). Alternatively, the body fat sensor 725 is a handheld device.

The environmental sensors 704 include an environmental temperature sensor 726, a humidity sensor 727, a noise sensor 728, an air quality sensor 730, a light sensor 732, a motion sensor 733, a barometric sensor 734, and/or a camera 735. In one embodiment, the environmental temperature sensor 726, the humidity sensor 727, the noise sensor 728, the air quality sensor 730, the light sensor 732, the motion sensor 733, the barometric sensor 734, the camera 735 are incorporated into a home automation system (e.g., AMAZON ALEXA, APPLE HOMEKIT, GOOGLE HOME, IF THIS THEN THAT (IFTTT), NEST). Alternatively, the environmental temperature sensor 726, the humidity sensor 727, the noise sensor 728, the light sensor 732, and/or the camera 735 are incorporated into a smartphone or tablet. In one embodiment, the noise sensor 728 is a microphone. In one embodiment, the air quality sensor 730 measures carbon monoxide, carbon dioxide, nitrogen dioxide, sulfur dioxide, particulates, and/or volatile organic compounds (VOCs). In another embodiment, at least one environmental sensor 704 is operable to transmit data to the remote device 511 and/or the remote server 708 in real time.

The remote device 511 is preferably a smartphone or a tablet. Alternatively, the remote device 511 is a laptop or a desktop computer. The remote device 511 includes a processor 760, an analytics engine 762, a control interface 764, and a user interface 766. The remote device 511 accepts data input from the body sensors 702 and/or the environmental sensors 704. The remote device also accepts data input from the remote server 708. The remote device 511 stores data in a local storage 706.

The local storage 706 on the remote device 511 includes a user profile 736, historical subjective data 738, predefined programs 740, custom programs 741, historical objective data 742, and historical environmental data 744. The user profile 736 stores stress reduction and sleep promotion system preferences and information about the user, including but not limited to, age, weight, height, gender, medical history (e.g., sleep conditions, medications, diseases), fitness (e.g., fitness level, fitness activities), sleep goals, stress level, and/or occupational information (e.g., occupation, shift information). The medical history includes caffeine consumption, alcohol consumption, tobacco consumption, use of prescription sleep aids and/or other medications, blood pressure, restless leg syndrome, narcolepsy, headaches, heart disease, sleep apnea, depression, stroke, diabetes, insomnia, anxiety or post-traumatic stress disorder (PTSD), and/or neurological disorders.

In one embodiment, the medical history incorporates information gathered from the Epworth Sleepiness Scale (ESS), the Insomnia Severity Index (IR), Generalized Anxiety Disorder 7-item (GAD-7) Scale, and/or Patient Heath Questionnaire-9 (PHQ-9) (assessment of depression). The ESS is described in Johns M W (1991). "A new method for measuring daytime sleepiness: the Epworth sleepiness scale", *Sleep,* 14 (6): 540-5, which is incorporated herein by reference in its entirety. The ISI is described in Morin et al. (2011). "The Insomnia Severity Index: Psychometric Indicators to Detect Insomnia Cases and Evaluate Treatment Response", *Sleep,* 34(5): 601-608, which is incorporated herein by reference in its entirety. The GAD-7 is described in Spitzer et al., "A brief measure for assessing generalized anxiety disorder: the GAD-7" *Arch Intern Med.,* 2006 May 22; 166(1):1092-7, which is incorporated herein by reference in its entirety. The PHQ-9 is described in Kroenke et al., "The PHQ-9: Validity of a Brief Depression Severity Measure", *J. Gen. Intern. Med.,* 2001 September; 16(9): 606-613, which is incorporated herein by reference in its entirety.

In one embodiment, the weight of the user is automatically uploaded to the local storage from a third-party application. In one embodiment, the third-party application obtains the information from a smart scale (e.g., FITBIT ARIA, WITHINGS BODY+, GARMIN INDEX, PIVOTAL LIVING SMART SCALE, IHEALTH CORE). In another embodiment, the medical history includes information gathered from a Resting Breath Hold test.

The historical objective data 742 includes information gathered from the body sensors 702. This includes information from the respiration sensor 712, the electrooculography sensor 713, the heart sensor 714, the movement sensor 716, the electromyography sensor 717, the brain wave sensor 718, the energy field sensor 719, the body temperature sensor 720, the analyte sensor 721, the pulse oximeter sensor 722, the blood pressure sensor 723, and/or the electrodermal activity sensor 724. In another embodiment, the historical objective data 742 includes information gathered from the Maintenance of Wakefulness Test, the Digit Symbol Substitution Test, and/or the Psychomotor Vigilance Test. The Maintenance of Wakefulness Test is described in Doghramji, et al., "A normative study of the maintenance of wakefulness test (MWT)", *Electroencephalogr. Clin. Neurophysiol.,* 1997 November; 103(5): 554-562, which is incorporated herein by reference in its entirety. The Digit Symbol Substitution Test is described in Wechsler, D. (1997). Wechsler Adult Intelligence Scale-Third edition (WAIS-III). San Antonio, TX: Psychological Corporation and Wechsler, D. (1997). Wechsler Memory Scale-Third edition (WMS-III). San Antonio, TX: Psychological Corporation, each of which is incorporated herein by reference in its entirety. The Psychomotor Vigilance Test is described in Basner et al., "Maximizing sensitivity of the psychomotor vigilance test (PVT) to sleep loss", *Sleep,* 2011 May 1; 34(5): 581-91, which is incorporated herein by reference in its entirety.

In another embodiment, the historical objective data 742 includes results from at least one genetic test (e.g., ANCESTRYDNA, 23 ANDME). In one embodiment, the at least one genetic test includes information regarding at least one gene, wherein the at least one gene includes RGS16, VIP, PER2, HCRTR2, RASD1, PER3, FBXL3, PLCL1, APH1A, FBXL13, NOL4, TOX3, AK5, DLSX5, PER1, and/or ALG10B. In another embodiment, the at least one genetic test includes information regarding at least one marker, wherein the at least one marker includes rs12736689, rs9479402, rs55694368, rs35833281, rs11545787, rs11121022, rs9565309, rs1595824, rs34714364, rs3972456, rs12965577, rs12927162, rs10493596, rs2948276, and/or rs6582618.

In yet another embodiment, the historical objective data 742 includes a chronotype. In one embodiment, the chronotype is determined using a self-assessment. In another embodiment, the chronotype is determined used the results from the at least one genetic test (e.g., PER3 gene). In yet another embodiment, the chronotype is determined using the body temperature sensor 720. Additional information regarding chronotype is in Putilov, et al., *How many diurnal types are there? A search for two further "bird species"* in Personality and Individual Differences, Volume 72, January 2015, pages 12-17, Schuster, et al. (2019). *Shift-specific associations between age, chronotype and sleep duration.* Chronobiology International, 36(6), 784-795. doi: 10.1080/07420528.2019.1586719, and Breus, Michael. *The Power of When: Discover Your Chronotype.* Little, Brown and Company, 2016, each of which is incorporated herein by reference in its entirety. In one embodiment, the system calculates a mid-sleep point. For example, if a sleep onset time is 11:00 pm and a sleep end time is 7:00 am, the mid-sleep point is 3:00 am.

Evidence suggests that circadian rhythms and possibly chronotype are able to be changed using temperature changes, especially cooling, have the potential to reset and change a person's circadian rhythms, as described in "Frozen? Let it go to reset circadian rhythms" by Harvey et al., EMBO J 39 (2020), which is incorporated herein by reference in its entirety.

The historical environmental data 744 includes information gathered from the environmental sensors 704. This includes information from the environmental temperature sensor 726, the humidity sensor 727, the noise sensor 728, the air quality sensor 730, the light sensor 732, the barometric sensor 734, and/or the camera 735.

The historical subjective data 738 includes information regarding sleep and/or stress. In one embodiment, the information regarding sleep is gathered from manual sleep logs (e.g., Pittsburgh Sleep Quality Index). The manual sleep logs include, but are not limited to, a time sleep is first attempted, a time to fall asleep, a time of waking up, hours of sleep, number of awakenings, times of awakenings, length of awakenings, perceived sleep quality, use of medications to assist with sleep, difficulty staying awake and/or concentrating during the day, difficulty with temperature regulation at night (e.g., too hot, too cold), trouble breathing at night (e.g., coughing, snoring), having bad dreams, waking up in the middle of the night or before a desired wake up time, twitching or jerking in the legs while asleep, restlessness while asleep, difficulty sleeping due to pain, and/or needing to use the bathroom in the middle of the night. The Pittsburgh Sleep Quality Index is described in Buysse, et al., "The Pittsburgh sleep quality index: A new instrument for psychiatric practice and research" *Psychiatry Research*. 28 (2). 193-213 (May 1989), which is incorporated herein by reference in its entirety.

In another embodiment, the historical subjective data 738 includes information gathered regarding sleepiness (e.g., Karolinska Sleepiness Scale, Stanford Sleepiness Scale, Epworth Sleepiness Scale). The Karolinska Sleepiness Scale is described in Åkerstedt, et al., "Subjective and objective sleepiness in the active individual", *Int J Neurosc.*, 1990; 52:29-37 and Baulk et al., "Driver sleepiness—evaluation of reaction time measurement as a secondary task", *Sleep,* 2001; 24(6):695-698, each of which is incorporated herein by reference in its entirety. The Stanford Sleepiness Scale is described in Hoddes E. (1972). "The development and use of the Stanford sleepiness scale (SSS)" *Psychophysiology.* 9 (150) and Maclean, et al. (1992 Mar. 1). "Psychometric evaluation of the Stanford Sleepiness Scale". *Journal of Sleep Research.* 1 (1): 35-39, each of which is incorporated herein by reference in its entirety.

In yet another embodiment, the historical subjective data 738 includes information regarding tension or anxiety, depression or dejection, anger or hostility, and/or fatigue or inertia gathered from the Profile of Mood States. The Profile of Mood States is described in the Profile of Mood States, $2^{nd}$ Edition published by Multi-Health Systems (2012) and Curran et al., "Short Form of the Profile of Mood States (POMS-SF): Psychometric information", *Psychological Assessment.* 7 (1): 80-83 (1995), each of which is incorporated herein by reference in its entirety. In another embodiment, the historical subjective data 738 includes information gathered from the Ford Insomnia Response to Stress Test (FIRST), which asks how likely a respondent is to have difficulty sleeping in nine different situations. The FIRST is described in Drake et al., "Vulnerability to stress-related sleep disturbance and hyperarousal", *Sleep,* 2004; 27:285-91 and Drake et al., "Stress-related sleep disturbance and polysomnographic response to caffeine", *Sleep Med,* 2006; 7:567-72, each of which is incorporated herein by reference in its entirety. In still another embodiment, the historical subjective data 738 includes information gathered from the Impact of Events, which assesses the psychological impact of stressful life events. A subscale score is calculated for intrusion, avoidance, and/or hyperarousal. The Impact of Events is described in Weiss, D. S., & Marmar, C. R. (1996). The Impact of Event Scale—Revised. In J. Wilson & T. M. Keane (Eds.), Assessing psychological trauma and PTSD (pp. 399-411). New York: Guilford, which is incorporated herein by reference in its entirety. In one embodiment, the historical subjective data 738 includes information gathered from the Social Readjustment Rating Scale (SRRS). The SRRS lists 52 stressful life events and assigns a point value based on how traumatic the event was determined to be by a sample population. The SRRS is described in Holmes et al., "The Social Readjustment Rating Scale", *J. Psychosom. Res.* 11(2): 213-8 (1967), which is incorporated herein by reference in its entirety.

In one embodiment, the predefined programs 740 are general sleep settings for various conditions and/or body types (e.g., weight loss, comfort, athletic recovery, hot flashes, bed sores, depression, multiple sclerosis, alternative sleep cycles). In one embodiment, a weight loss predefined program sets a surface temperature at a very cold setting (e.g., 15.56-18.89° C. (60-66° F.)) to increase a metabolic response, resulting in an increase in calories burned, which then leads to weight loss. Temperature settings are automatically adjusted to be as cold as tolerable by the user after the first sleep cycle starts to maximize the caloric burn while having the smallest impact on sleep quality. For example, the core temperature of an overweight individual often fails to drop due to a low metabolism. In one example, the surface temperature is 20° C. (68° F.) at the start of a sleep period, 18.89° C. (66° F.) during N1-N2 sleep, 18.33° C. (65° F.) during N3 sleep, 19.44° C. (67° F.) during REM sleep, and 20° C. (68° F.) to wake the user.

In one embodiment, the custom programs 741 are sleep settings defined by the user. In one example, the user creates a custom program by modifying a predefined program (e.g., the weight loss program above) to be 1.11° C. (2° F.) cooler during the N3 stage. In another example, the user creates a custom program by modifying a predefined program to have a start temperature of 37.78° C. (100° F.). The custom programs 741 allow a user to save preferred sleep settings.

The remote server 708 includes global historical subjective data 746, global historical objective data 748, global historical environmental data 750, global profile data 752, a global analytics engine 754, a calibration engine 756, a simulation engine 758, and a reasoning engine 759. The global historical subjective data 746, the global historical objective data 748, the global historical environmental data 750, and the global profile data 752 include data from multiple users.

The system components 710 include a mattress pad 11 with adjustable temperature control, a mattress with adjustable firmness 768, a mattress with adjustable elevation 770, an alarm clock 772, a thermostat to adjust the room temperature 774, a lighting system 776, a fan 778, a humidifier 780, a dehumidifier 782, a pulsed electromagnetic field (PEMF) device 784, a transcutaneous electrical nerve stimulation (TENS) device 785, a sound generator 786, an air purifier 788, a scent generator 790, a red light and/or near-infrared lighting device 792, a sunrise simulator 793, and/or a sunset simulator 794.

The body sensors 702, the environmental sensors 704, the remote device 511 with local storage 706, the remote server 708, and the system components 710 are designed to connect directly (e.g., Universal Serial Bus (USB) or equivalent) or wirelessly (e.g., BLUETOOTH, WI-FI, ZIGBEE) through systems designed to exchange data between various data collection sources. In a preferred embodiment, the body sensors 702, the environmental sensors 704, the remote device 511 with local storage 706, the remote server 708, and the system components 710 communicate wirelessly through BLUETOOTH. Advantageously, BLUETOOTH emits lower electromagnetic fields (EMFs) than WI-FI and cellular signals.

Additional information regarding the stress reduction and sleep promotion system is in U.S. Patent Publication Nos. 2018/0000255 and 2018/0110960, each of which is incorporated herein by reference in its entirety. U.S. Provisional Patent Application No. 62/780,637, filed Dec. 17, 2018, discusses a system for enhancing sleep recovery and promoting weight loss and is incorporated herein by reference in its entirety. U.S. Provisional Patent Application No. 62/792,572, filed Jan. 15, 2019, discusses a health data exchange platform and is incorporated herein by reference in its entirety.

Figure 3:
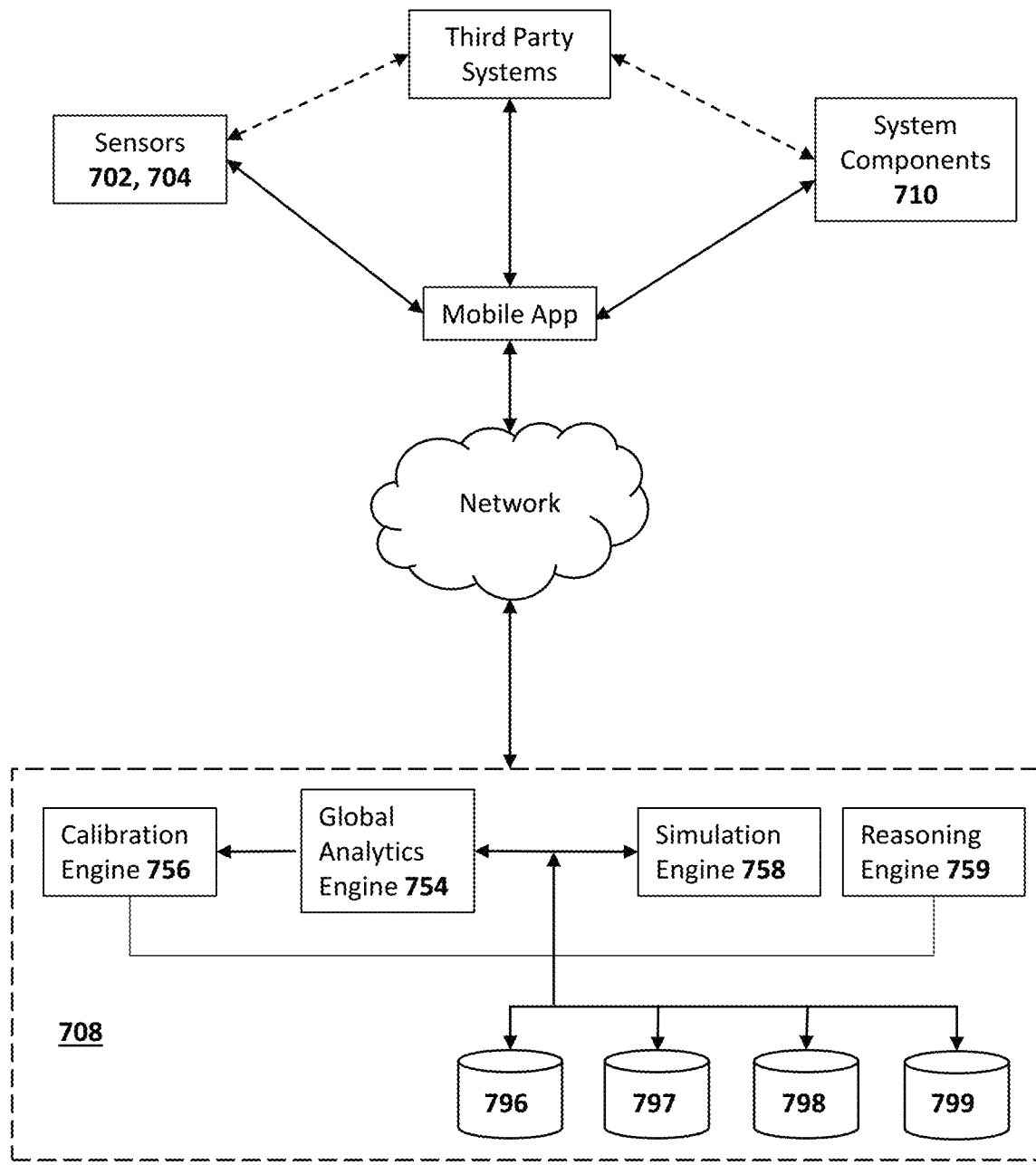
FIG. 3 is a block diagram of one embodiment of the system architecture.

As shown in FIG. 3, in one embodiment, the remote server 708 hosts a global analytics engine 754, a calibration engine 756, a simulation engine 758, a reasoning engine 759, and databases 796, 797, 798, and 799. Although four databases are shown, it is equally possible to have any number of databases greater than one. The global analytics engine 754 generates predicted values for a monitored stress reduction and sleep promotion system using a virtual model of the stress reduction and sleep promotion system based on real-time data. The calibration engine 756 modifies and updates the virtual model based on the real-time data. Any operational parameter of the virtual model is able to be modified by the calibration engine 756 as long as the resulting modification is operable to be processed by the virtual model.

The global analytics engine 754 analyzes differences between the predicted values and optimized values. If the difference between the optimized values and the predicted values is greater than a threshold, then the simulation engine 758 determines optimized values of the monitored stress reduction and sleep promotion system based on the real-time data and user preferences. In one embodiment, the global analytics engine 754 determines whether a change in parameters of the system components 710 is necessary to optimize sleep based on the output of the simulation engine 758. If a change in parameters is necessary, the new parameters are transmitted to a mobile application on the remote device and then to the system components 710. The calibration engine 756 then updates the virtual model with the new parameters. Thus, the system autonomously optimizes the stress reduction and sleep promotion system (e.g., surface temperature) without requiring input from a user.

In another embodiment, the remote server 708 includes a reasoning engine 759 built with artificial intelligence (AI) algorithms. The reasoning engine 759 is operable to generate a reasoning model based on multiple sets of training data. The multiple sets of training data are a subset of global historical subjective data, global historical objective data, global historical environmental data, and global profile data. For example, a user's stress level and/or sleep efficiency significantly improve after engaging in an activity over a period of time, which is then included in the training data. The training data includes context data (e.g., baseline data, body sensor data) and action data (e.g., activity data, system component use). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. patent application Ser. No. 15/900,398 is incorporated herein by reference in its entirety.

Figure 4:
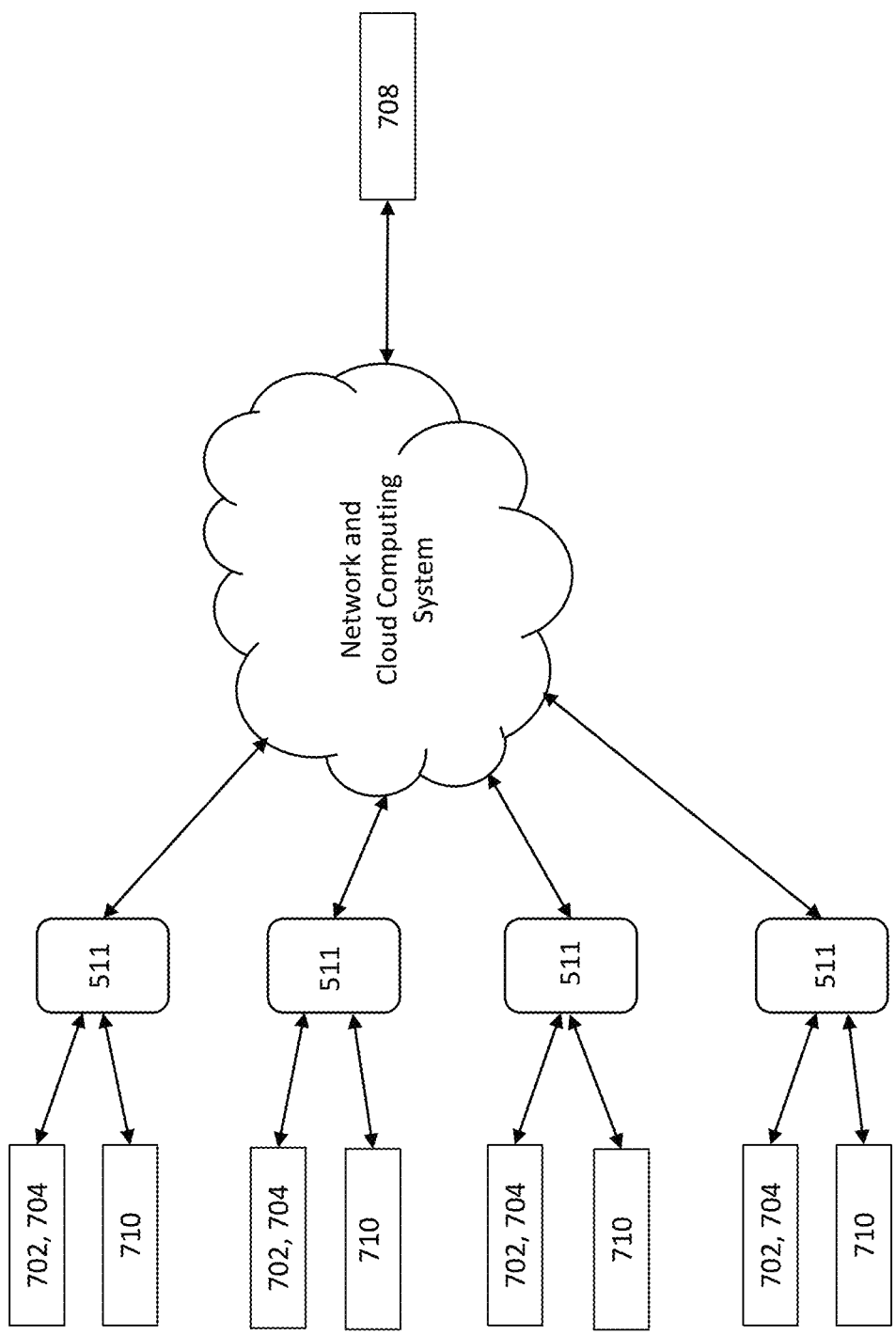
FIG. 4 is an illustration of a network of stress reduction and sleep promotion systems.

FIG. 4 is an illustration of a network of stress reduction and sleep promotion systems. Data from multiple users is able to be stored on a remote server 708. The remote server 708 is connected through a network and cloud computing system to a plurality of remote devices 511. Each of the plurality of remote devices 511 is connected to body sensors 702 and/or environmental sensors 704, as well as system components 710. Although one remote server is shown, it is equally possible to have any number of remote servers greater than one. A user is able to opt into sending their data to the remote server 708, which is stored in at least one database on the remote server 708. The simulation engine on the remote server 708 is operable to use data from the multiple users to determine customized and optimized sleep settings for the user based on personal preferences (e.g., a target number of hours of sleep, a preferred bed time, a preferred wake time, a faster time to fall asleep, fewer awakenings during the sleeping period, more REM sleep, more deep sleep, and/or a higher sleep efficiency) or physical condition (e.g., weight loss, comfort, athletic recovery, hot flashes, bed sores, depression). In one example, the temperature settings for a temperature-conditioned mattress pad for a user with hot flashes are automatically determined by the simulation engine examining data obtained from other users with hot flashes and a temperature-conditioned mattress pad stored in databases on the remote server. The simulation engine is also operable to use data from the multiple users to provide recommendations (e.g., activities, system components) to users with a similar background (e.g., gender, age, health condition).

The stress reduction and sleep promotion system includes a virtual model of the stress reduction and sleep promotion system. The virtual model is initialized based on the program selected. The virtual model of the stress reduction and sleep promotion system is dynamic, changing to reflect the status of the stress reduction and sleep promotion system in real time or near real time. The virtual model includes information from the body sensors and the environmental sensors. Based on the data from the body sensors and the environmental sensors, the virtual model generates predicted values for the stress reduction and sleep promotion system. A sleep stage (e.g., awake, Stage N1, Stage N2, Stage N3, REM sleep) for the user is determined from the data from the body sensors.

The stress reduction and sleep promotion system is monitored to determine if there is a change in status of the body sensors (e.g., change in body temperature), the environmental sensors (e.g., change in room temperature), the system components (e.g., change in temperature of mattress pad), or sleep stage of the user. If there is a change in status, the virtual model is updated to reflect the change in status. Predicted values are generated for the stress reduction and sleep promotion system. If a difference between the optimized values and the predicted values is greater than a threshold, a simulation is run on the simulation engine to optimize the stress reduction and sleep promotion system based on the real-time data. The simulation engine uses information including, but not limited to, global historical subjective data, global historical objective data, global historical environmental data, and/or global profile data to determine if a change in parameters is necessary to optimize the stress reduction and sleep promotion system. In one example, the temperature of the mattress pad is lowered to keep a user in Stage N3 sleep for a longer period of time. In another example, the mobile application provides recommendations of an activity to a user.

As previously mentioned, the at least one remote device preferably has a user interface (e.g., a mobile application for a smartphone or tablet) that allows the stress reduction and sleep promotion system to adjust the parameters of the stress reduction and sleep promotion system. The parameters of the stress reduction and sleep promotion system (e.g., target temperatures of a mattress pad) are able to be manipulated through the sleeping period using a predefined program or a customized program based on user preferences to produce a deeper, more restful sleep.

Because the target temperatures are able to be set at any time, those target temperatures are able to be manipulated through the sleeping period in order to match user preferences or a program to correlate with user sleep cycles to produce a deeper, more restful sleep.

In one embodiment, the mobile application measures a time when a user began attempting to sleep (TATS), a TATS start time, a TATS end time, a time in bed (TIB), a TIB start time, and/or a TIB end time. The mobile application calculates a total TATS duration based on the TATS start time and the TATS end time. The mobile application also calculates a total TIB duration based on the TIB start time and the TIB end time. In one embodiment, the TATS start time, the TATS end time, the TIB start time, and/or the TIB end time are indicated by the user (e.g., by pressing a button in the mobile application). Alternatively, the TATS start time, the TATS end time, the TIB start time, and/or the TIB end time are determined by sensors. In one example, the TATS start time is determined by a user's eyes closing while in bed. In another example, the TATS end time is determined by increased motion as measured by a movement sensor and/or opening of the eyes. In yet another example, the TIB start time is determined by sensors indicating a user is horizontal and/or bed or room sensors indicating the user is in bed. In still another example, the TIB end time is determined by sensors indicating a user is not horizontal and/or bed or room sensors indicating the user is not in bed.

The mobile application is operable to determine whether a user is awake or asleep. The state of wakefulness (i.e., "awake") is characterized by cognitive awareness and/or consciousness, responsiveness to environmental cues, sustained movement detected by a movement sensor, beta and/or alpha waves as detected by EEG, increased heart rate, increased respiration, increased blood pressure, increased electrodermal activity, increased body temperature, open eyes, voluntary eye movements, and/or increased EMG on the chin. The state of sleep (i.e., "asleep") is characterized by loss of alertness and/or consciousness, lack of response to environmental cues, lack of movement, reduction in alpha waves as detected by EEG, increased theta and delta waves as detected by EEG, decreased heart rate, decreased respiration, decreased blood pressure, decreased body temperature, closed eyes, eye twitches, and/or decreased oxygen saturation.

In a preferred embodiment, the mobile application is operable to measure an initial sleep onset time and/or a final awakening time. The initial sleep onset time is a first occurrence of sleep after the TATS start time. The final awakening time is a time immediately after the last occurrence of sleep before the TATS end time. In one embodiment, the mobile application calculates a latency to sleep onset as the duration of a time interval between the TATS start time to the initial sleep onset time. In another embodiment, the mobile application calculates a latency to arising as the duration of a time interval between the final awakening time to the TATS end time. In a preferred embodiment, the mobile application is operable to calculate a sleep efficiency percentage. In one embodiment, the sleep efficiency percentage is defined as the total sleep time divided by the total TATS duration. In an alternative embodiment, the sleep efficiency percentage is defined as the total sleep time divided by the total TIB duration.

In one embodiment, the mobile application is operable to determine a total sleep period duration, a total sleep time, a sleep maintenance percentage, a total wakefulness duration, a wakefulness duration after initial sleep onset, a total number of awakenings, an awakening rate per hour, and/or a sleep fragmentation rate.

In another embodiment, the mobile application is operable to determine REM sleep, N1 sleep, N2 sleep, and/or N3 sleep. REM sleep is characterized by low-voltage, mixed-frequency EEG activity with less than 15 seconds of alpha activity, saw-tooth theta EEG activity, rapid eye movements, and/or decreased or absent EMG activity on the chin. N1 sleep is characterized by low-voltage, mixed-frequency EEG activity with less than 15 seconds of alpha activity in a 30-second epoch, no sleep spindles or K complexes, possible slow rolling eye movements, and/or diminished EMG activity on the chin. N2 sleep is characterized by sleep spindle and/or K complex activity, absence of eye movements, and/or diminished EMG activity on the chin. N3 sleep is characterized by high amplitude (e.g., greater than 75 µV peak-to-peak), slow wave (e.g., frequency of 4 Hz or less) EEG activity. In yet another embodiment, the mobile application is operable to calculate REM sleep duration, percentage, and latency from sleep onset; N1 sleep duration, percentage, and latency from sleep onset; N2 sleep duration, percentage, and latency from sleep onset; and/or N3 sleep duration, percentage, and latency from sleep onset.

Alternatively, the calculations and determining of sleep states described above are determined over the network on a remote server. In one embodiment, the calculations and determining of sleep states are then transmitted to at least one remote device. In yet another embodiment, the calculations and determining of sleep states described above are determined using third party software and transmitted to the mobile application.

The mobile application preferably serves as a hub to interface with the system components, the body sensors, the environmental sensors, and/or at least one third-party application (e.g., APPLE HEALTH, MYFITNESSPAL, nutrition tracker). The mobile application is operable to obtain data from a mattress pad (e.g., OOLER) and/or a wearable (e.g., OURA, APPLE WATCH, FITBIT, SAMSUNG GALAXY WATCH). The mobile application is operable to recognize patterns the user does not already see and help guide them to a new pattern. For example, many nutrition trackers monitor food and water intake and set daily and long-term calorie and weight goals. However, these nutrition trackers do not combine this information with additional data. In one example, data from the nutrition tracker is combined with GPS information to prompt a user before they eat fast food. The mobile application uses the chatbot to interact with the user before they eat fast food (e.g., positive quote, breathing exercise, reminder about goals). Additionally, the mobile application encourages the user to add the food into the mobile application and/or third-party application before they eat so the user is aware of what they are consuming. The mobile application also is operable to propose a meal for the user and/or an exercise plan that allows the user to meet goals or minimize damage from the fast food.

Additionally, the mobile application uses cognitive behavioral therapy (CBT) with artificial intelligence (AI) to help a user make incremental changes to improve sleep and health. CBT relies on three components: actions, thoughts, and feelings. The mobile application encourages activities, positive thoughts, and social interaction to increase happiness and decrease depression. The mobile application preferably uses a chatbot to interact with the user. Alternatively, the mobile application has at least one coach to interact with the user. The mobile application is operable to provide repetitive coaching, which is necessary for long-term habit change. For example, the mobile application reminds a user to take a vitamin every morning until the user begins logging the action on their own. The mobile application also reminds the user to take the vitamin when the user does not log the action. The mobile application is also operable to assist a user in creating positive coping mechanisms to manage and diffuse stress daily. For example, the mobile application learns over time that the user enjoys walking for stress relief. When the mobile application detects that a user is stressed, the mobile application recommends taking a walk. Further, the mobile application is operable to understand natural language voices, converse with the user, and execute voice commands.

The mobile application uses machine learning to identify positive behaviors, negative behaviors, antecedents or causes of positive behaviors, antecedents or causes of negative behaviors, triggers, early or past experiences that impact current behavior, and/or core belief structures and patterns. The mobile application is also operable to use machine learning to identify timing of the positive behaviors, the negative behaviors, the antecedents or causes of positive behaviors, the antecedents or causes of negative behaviors, and/or the triggers. The timing is a daily, weekly, monthly, or other interval (e.g., two weeks, six weeks) basis.

The mobile application also uses machine learning to identify patterns of habits and behaviors. For example, the mobile application is operable to determine when to push notifications based on when a user is likely to be looking at their phone (e.g., before work, during lunch, after work). The mobile application is also operable to determine when a user is stressed (e.g., via user identification and/or sensor data). In one embodiment, the machine learning incorporates information, including, but not limited to, mobile phone usage, mobile application usage, GPS location, and/or sensor data.

In one embodiment, the mobile application updates the machine learning models via feedback from a user, a friend, a family member, a healthcare provider, and/or an expert (e.g., nutritionist, sleep coach, trainer, therapist, fitness coach).

In one embodiment, the mobile application asks the user to identify at least one problem the user wants to improve. The mobile application is operable to identify patterns, triggers, and stimuli for stress. In another embodiment, the mobile application is operable to analyze the at least one problem to determine which one of the at least one problem is easiest for the user to remedy. In one example, the mobile application prioritizes the one of the at least one problem. Advantageously, this allows the user to experience success with achieving a goal, providing motivation to tackle additional problems. The mobile application is operable to document a user's progress over time. In one embodiment, the mobile application provides positive feedback to a user when goals are achieved. In another embodiment, the mobile application is operable to designate at least one goal based on an amount of time to achieve the at least one goal (e.g., short term goal, medium term goal, long term goal).

In another embodiment, the mobile application provides a journaling component. In one example, a user is worried about financial problems, which are able to be dealt with via budget, planning, and/or organization tips via the mobile application. However, the journaling component provides a way to document and validate the user's stress, allowing the user to focus on other tasks during the day and sleep at night. In one embodiment, the journaling component includes a gratitude journal.

The mobile application preferably provides a social network component for a user to interact with other users with similar interests or health conditions. In one embodiment, the mobile application identifies at least one group for a user based on health markers, mental health markers, goals, age, gender, social and economic groups, religion, etc. The social network component also allows for the creation of sharing groups that promote trust. In one example, the mobile application allows for the creating of a sharing group dedicated to domestic abuse survivors to provide emotional support to members of the group. Further, patterns of response trigger movement between groups. For example, a user with social anxiety falls into multiple groups, but based on their response to interventions and the types of interventions that are having success, the prediction of what will help the most and, therefore, the group assignment will change. In another example, an overweight user with sleep apnea who loses weight and remedies the sleep apnea naturally will move out of the sleep apnea group after the weight loss. However, that user is also able to move into a group that focuses on social anxiety and/or using food as a coping mechanism. Additionally, the social network component allows for a user to challenge other users to complete activities.

The mobile application allows a user to identify stress, label the source of the stress, and put users into patterns of emotions, thoughts, and behaviors to categorize intervention suggestions. In one example, a user suffers from social anxiety and, therefore, avoids phone calls and large group events. The mobile application allows a user to rank activities based on stress level (e.g., scale from 1 to 10). The mobile application provides suggestions for how to manage stress and requests feedback from the user to identify what is working. For example, the mobile application encourages a user to meditate both before and after a large group event. Additionally, the mobile application provides a checklist and measurements for success.

In another example, the mobile application assists a user through a death. Based on time and patterns for grief (e.g., Kubler-Ross model), the mobile application encourages a user through the process of healing. The mobile application includes visualization exercises (e.g., visualizing putting bigger hurts in a closet and taking them out in small moments). The mobile application is operable to map a tree of support (e.g., family, friends, other users of the mobile application). The mobile application provides a positive quote, encourages meditation, and/or encourages a walk when the user is having a bad day (e.g., as noted by the user and/or detected by sensors).

In a preferred embodiment, the mobile application includes geolocation data. The geolocation data allows for targeted suggestions that are relevant to a user's location. For example, the mobile application suggests activities (e.g., races, events) located near the user. Additionally, geolocation data allows for tracking activity and behaviors by location. For example, the geolocation data allows for analysis of sleep, stress, and health (e.g., mental health) patterns for users in Alaska versus users located near the equator.

Figures 5, 6:
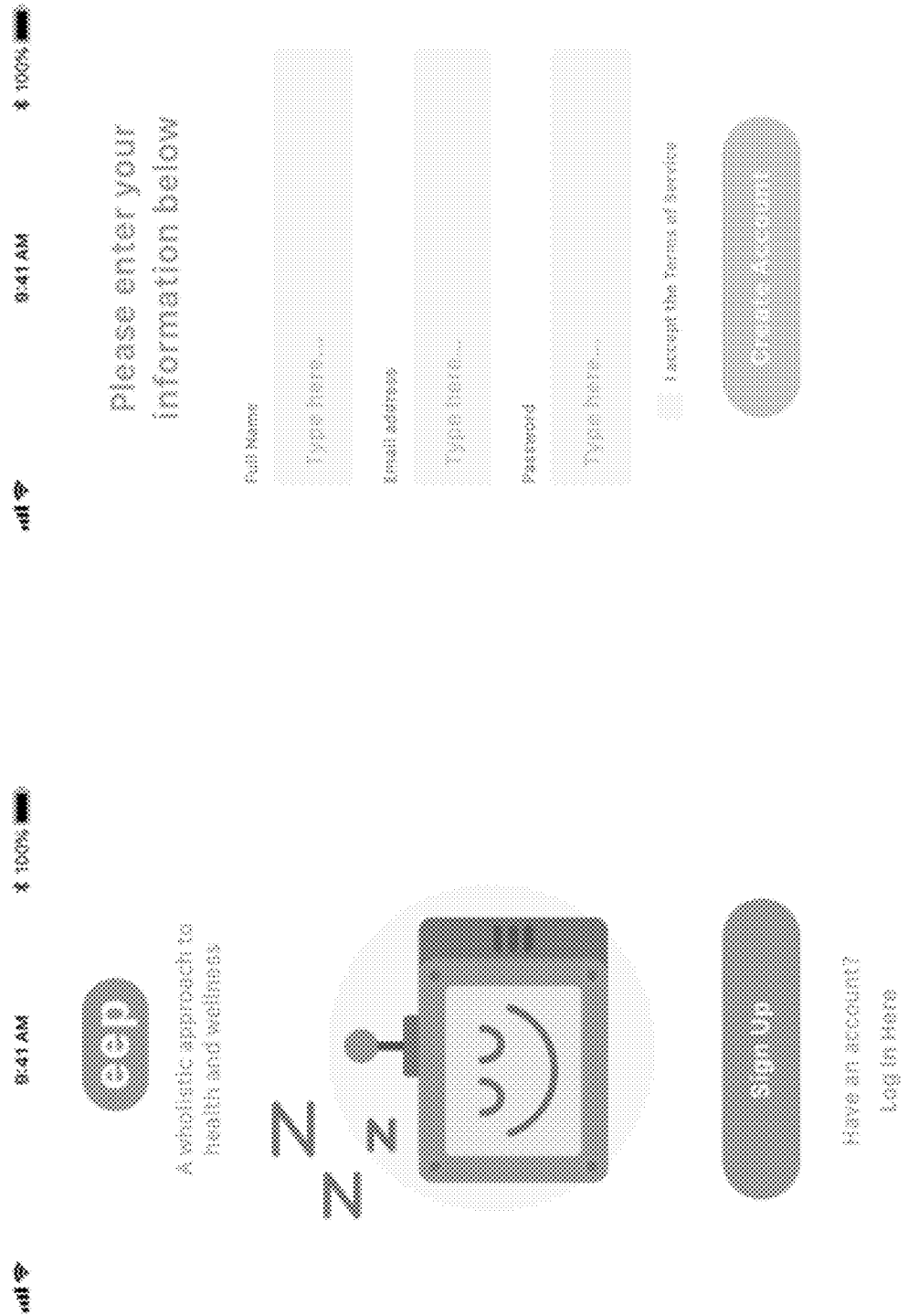
FIG. 5 illustrates a welcome screen for one embodiment of a GUI for a mobile application.
FIG. 6 illustrates an account creation screen for one embodiment of a GUI for a mobile application.
Figures 7, 8:
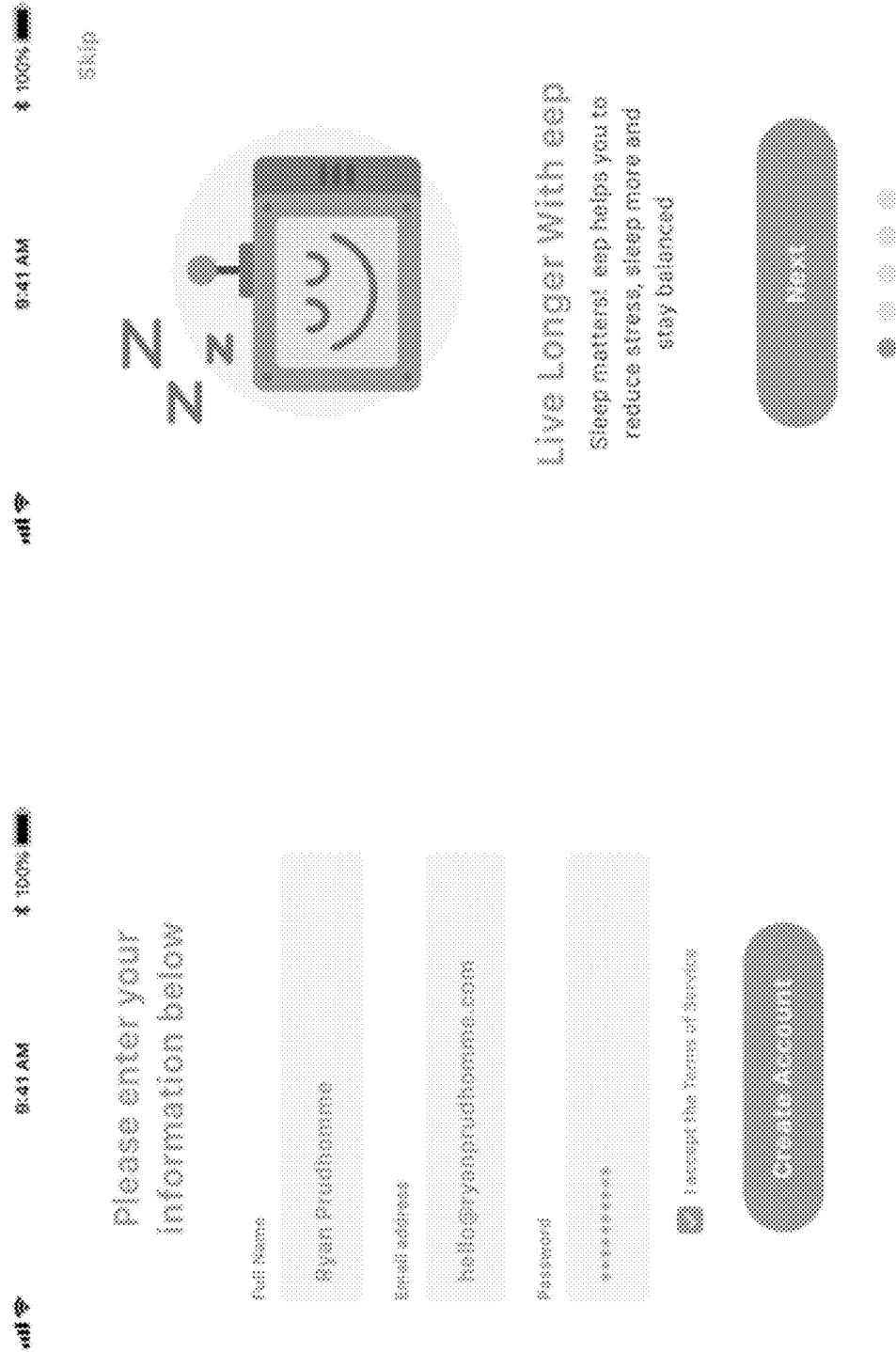
FIG. 7 illustrates the account creation screen with the user information added.
FIG. 8 illustrates an example of a GUI describing benefits of using the mobile application.

FIG. 5 illustrates a welcome screen for one embodiment of a GUI for a mobile application. The welcome screen allows a user to sign up for an account or log in to an established account. FIG. 6 illustrates an account creation screen for one embodiment of a GUI for a mobile application. The user enters a name (e.g., first and last), an email address, and a password. FIG. 7 illustrates the account creation screen with the user information added.

Figures 9, 10:
FIG. 9 illustrates an example of a GUI describing the relationship between stress and sleep.
FIG. 10 illustrates an example of a GUI describing how incremental changes in lifestyle add time to a user's life.
Figures 11, 12:
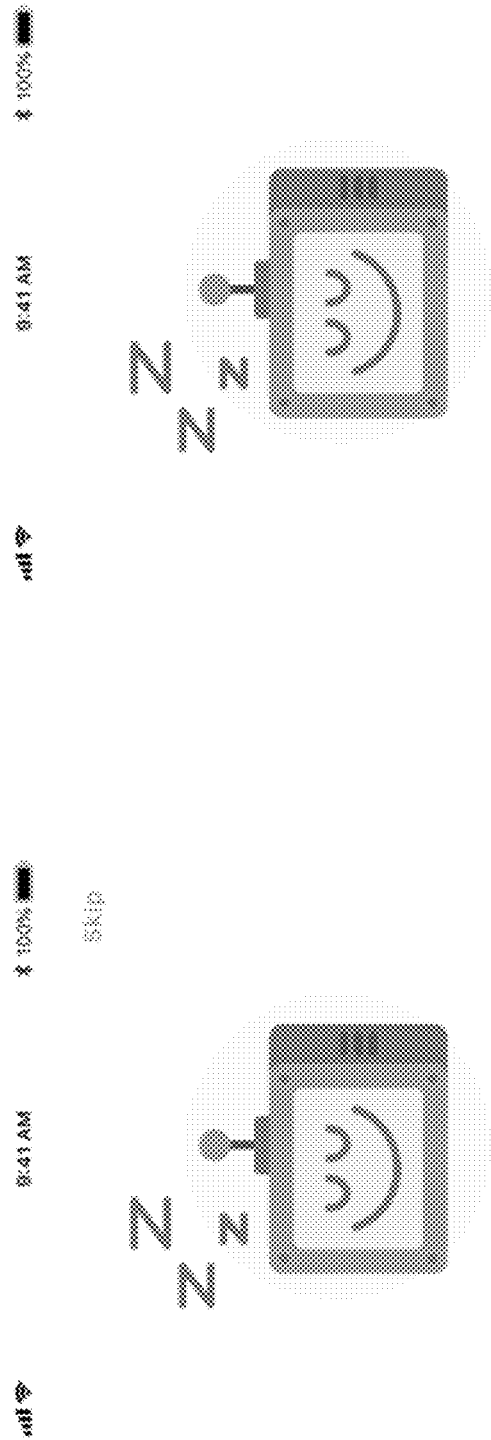
FIG. 11 illustrates an example of a GUI describing the combination of science, sleep, diet, and exercise adds time to a user's life.
FIG. 12 illustrates an example of a GUI describing the mobile application as a technological assistant to improve quality of life.

FIGS. 8-12 illustrate examples of onboarding screens for one embodiment of a GUI for a mobile application. FIG. 8 illustrates an example of a GUI describing benefits of using the mobile application. FIG. 9 illustrates an example of a GUI describing the relationship between stress and sleep. FIG. 10 illustrates an example of a GUI describing how incremental changes in lifestyle (e.g., mindfulness activities, sleep improvement, stress reduction) add time to a user's life. FIG. 11 illustrates an example of a GUI describing the combination of science, sleep, diet, and exercise adds time to a user's life. FIG. 12 illustrates an example of a GUI describing the mobile application as a technological assistant to improve quality of life (e.g., less stress, more sleep).

Figure 14:
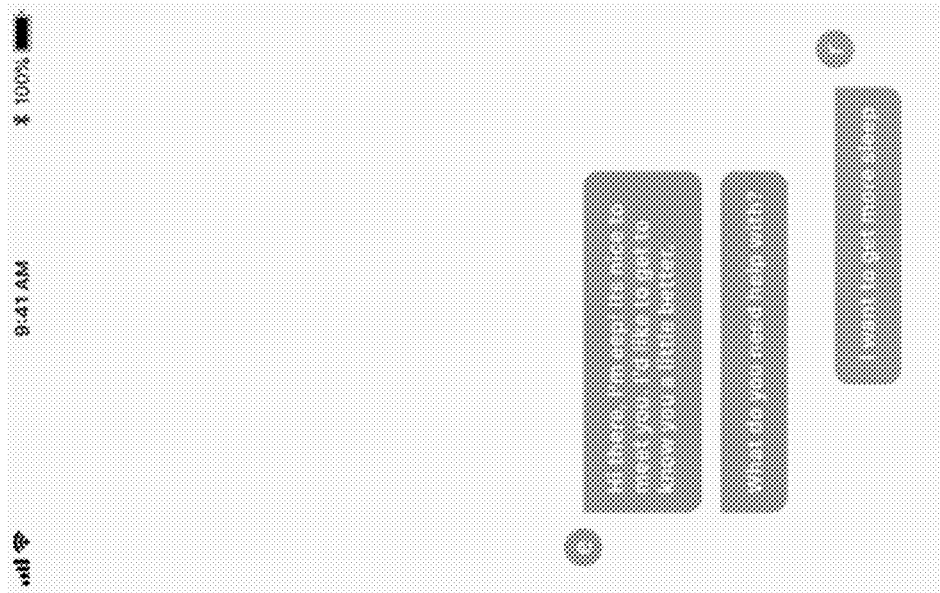
FIG. 14 illustrates an example of a chat where the user requests help getting more sleep.
Figure 13:
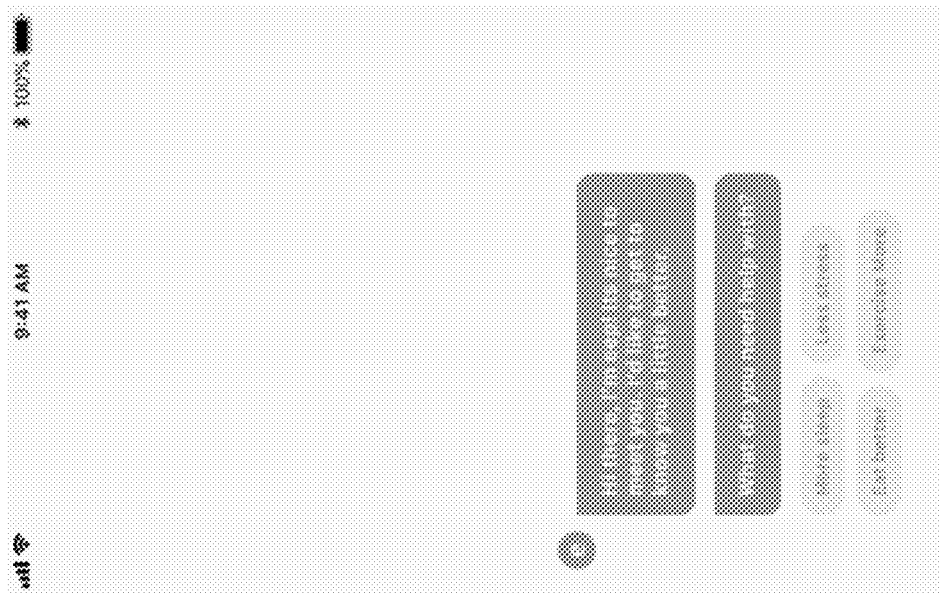
FIG. 13 illustrates an example of a chat where a chatbot asks what the user needs help with and provides buttons to select a topic.
Figure 16:
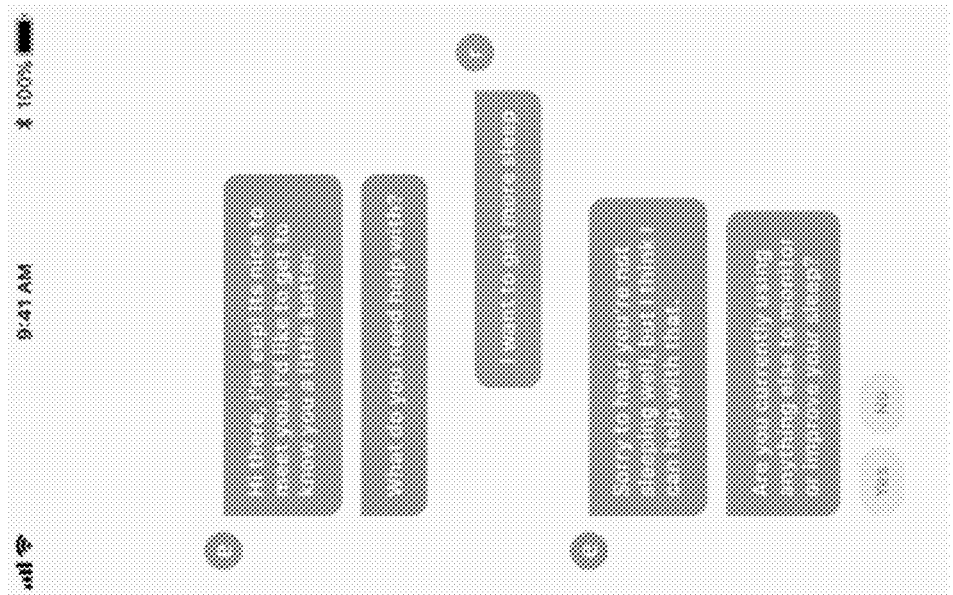
FIG. 16 illustrates an example of a chat where the chatbot allows a user to select yes or no in response to the question in FIG. 15.
Figure 15:
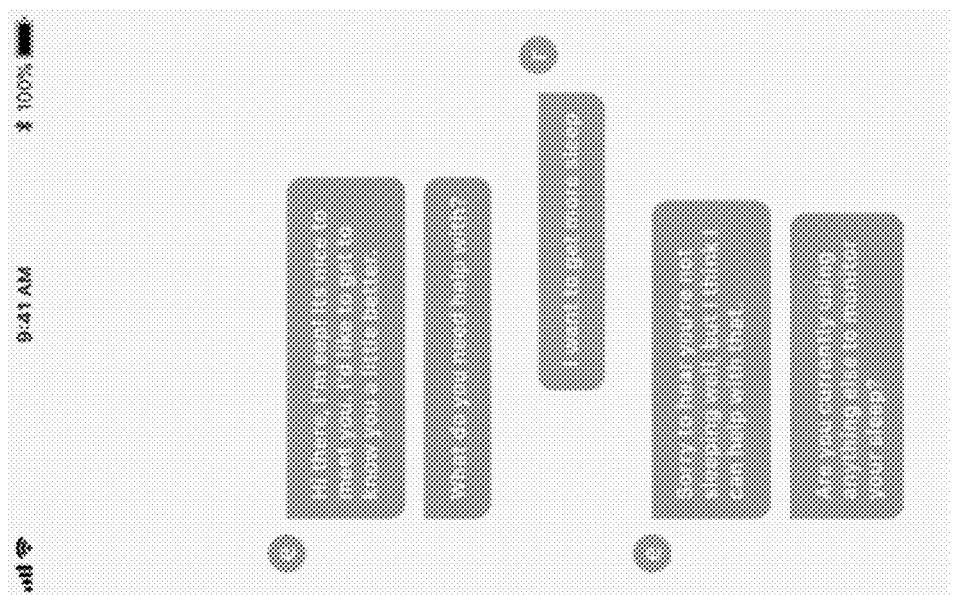
FIG. 15 illustrates an example of a chat where the chatbot asks if the user is currently using anything to monitor their sleep.
Figure 18:
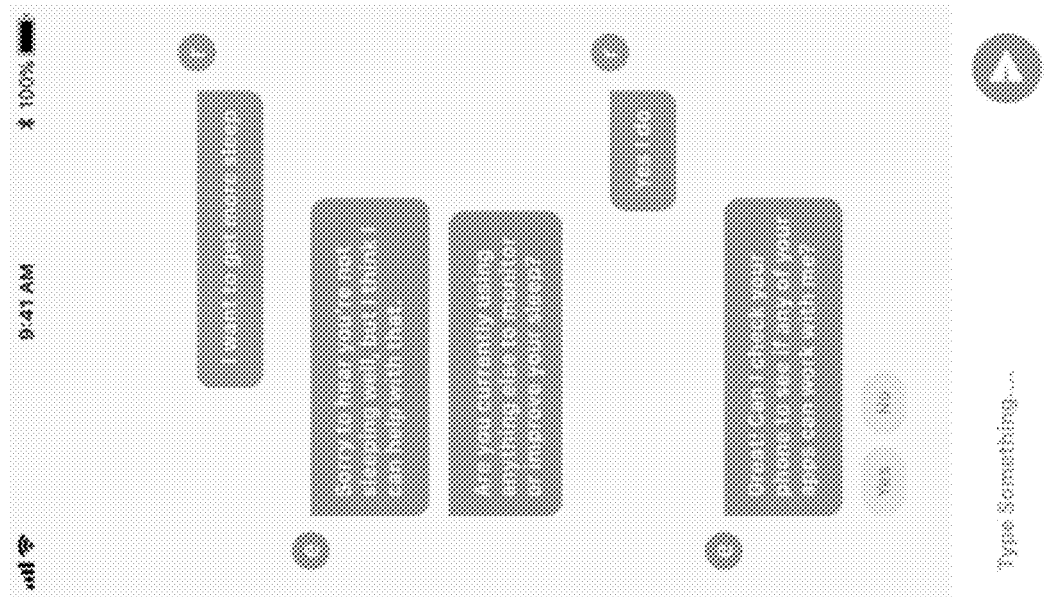
FIG. 18 illustrates an example of a chat where the chatbot asks if the mobile application is able to check the mobile device for other applications compatible with the mobile application.
Figure 17:
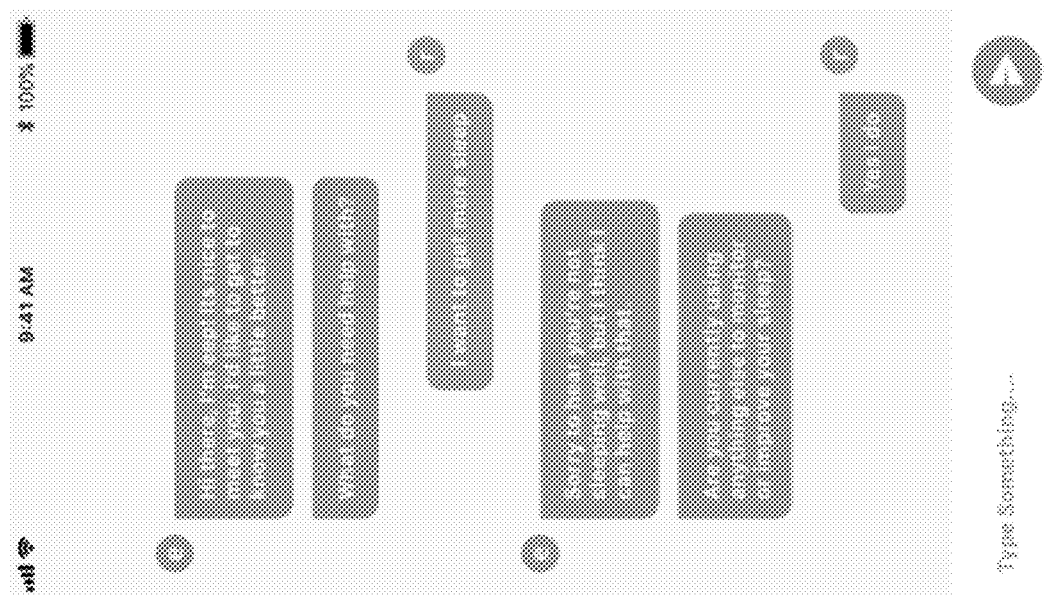
FIG. 17 illustrates an example of a chat where the user's response to the question in FIG. 15 is recorded.
Figure 20:
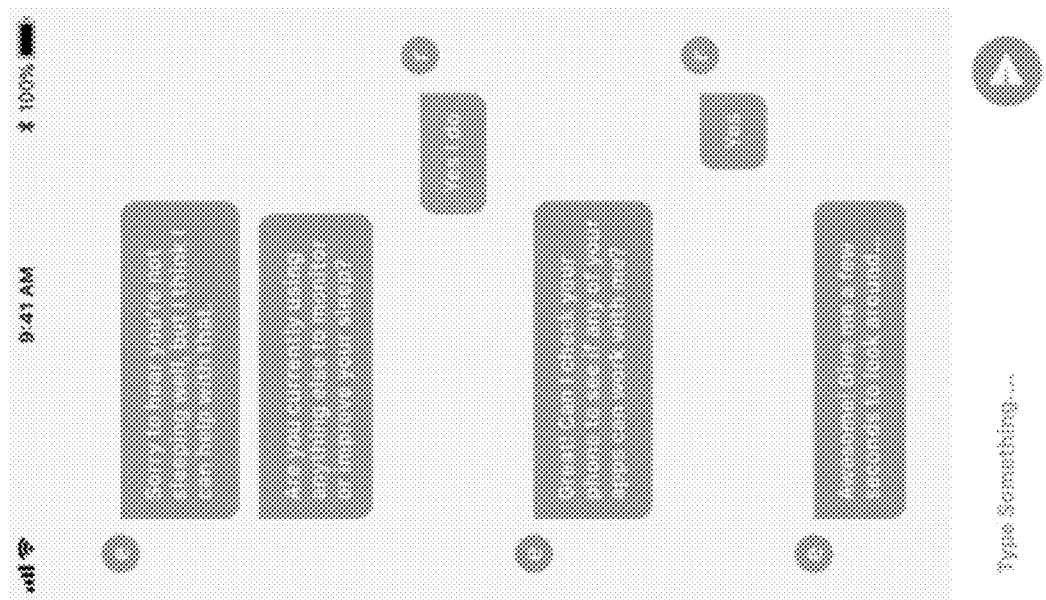
FIG. 20 illustrates an example of a chat where the chatbot thanks the user for the response and communicates that the mobile application is looking for other compatible applications.
Figure 19:
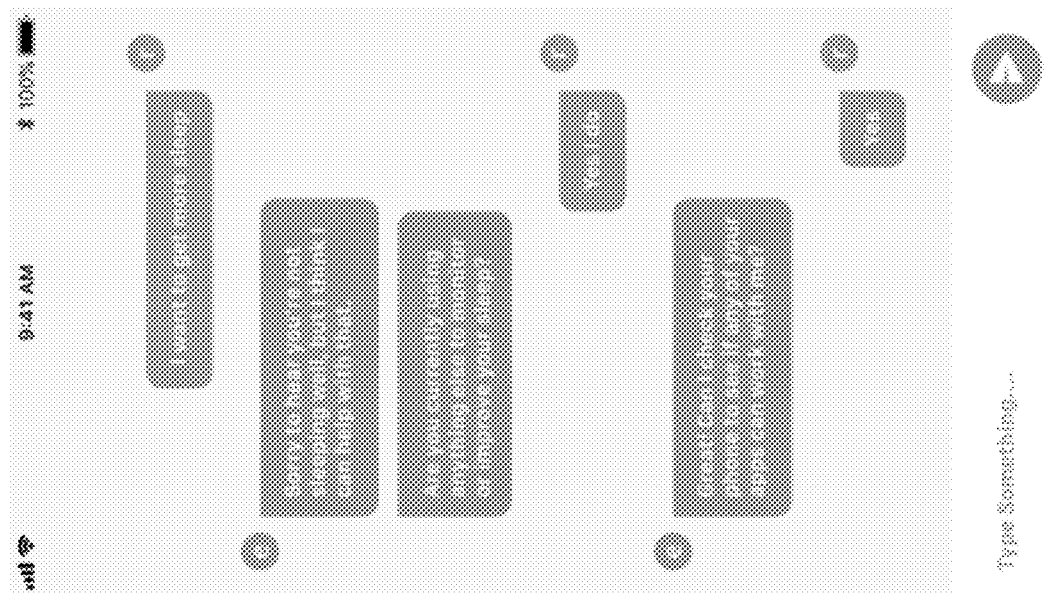
FIG. 19 illustrates an example of a chat where the user's response to the question in FIG. 18 is recorded.

FIGS. 13-20 illustrate examples of an onboarding chat for one embodiment of a GUI for a mobile application. FIG. 13 illustrates an example of a chat where a chatbot asks what the user needs help with and provides buttons to select a topic (e.g., more sleep, less stress, eat better, exercise more). FIG. 14 illustrates an example of a chat where the user requests help getting more sleep. FIG. 15 illustrates an example of a chat where the chatbot asks if the user is currently using anything to monitor their sleep. FIG. 16 illustrates an example of a chat where the chatbot allows a user to select yes or no in response to the question in FIG. 15. FIG. 17 illustrates an example of a chat where the user's response to the question in FIG. 15 is recorded. FIG. 18 illustrates an example of a chat where the chatbot asks if the mobile application is able to check the mobile device (e.g., phone, tablet) for other applications compatible with the mobile application. The chatbot allows a user to select yes or no in response to the question. FIG. 19 illustrates an example of a chat where the user's response to the question in FIG. 18 is recorded. FIG. 20 illustrates an example of a chat where the chatbot thanks the user for the response and communicates that the mobile application is looking for other compatible applications.

The mobile application is operable to determine a user's preferences over time. For example, if the user never selects running as a physical option, the chatbot asks why the user does not like to run. The chatbot allows a user to select a response (e.g., it hurts, don't like it, no place to do it). The chatbot is operable to provide a suggestion based on the user's response. For example, if the user selects "no place to do it", the chatbot provides suggestions of gyms and/or free recreational facilities near the user's work or home. As the mobile application learns more about a user's preferences and health, the mobile application is able to use machine learning (e.g., via the reasoning engine) to make better predictions about what is helpful to the user.

Figure 22:
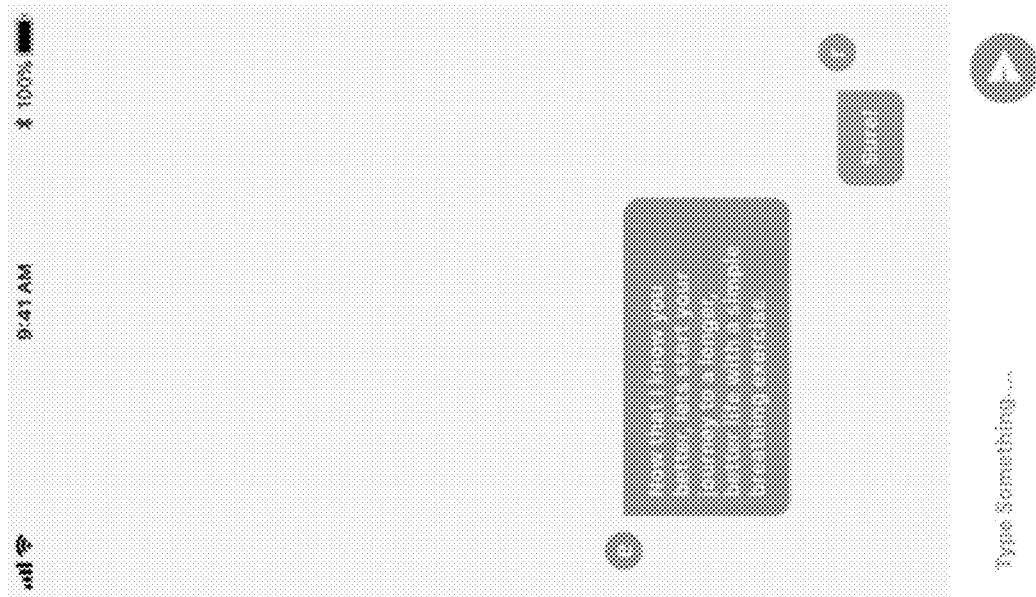
FIG. 22 illustrates an example of a chat where the user's response to the question in FIG. 21 is recorded.
Figure 21:
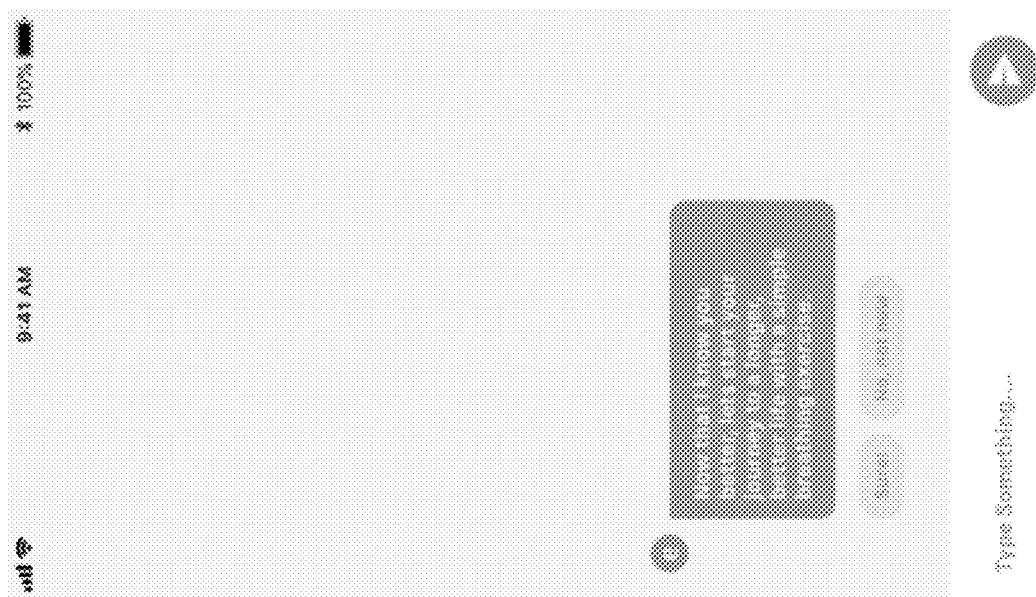
FIG. 21 illustrates an example of a chat where the chatbot asks if the user wants to complete a breathing exercise.
Figure 23:
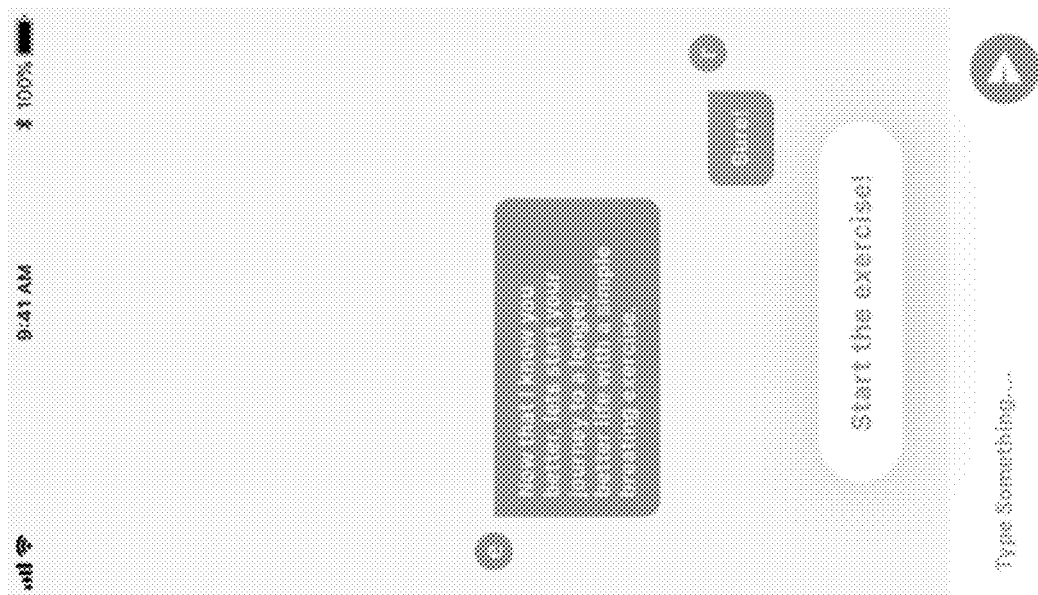
FIG. 23 illustrates an example of a chat where the chatbot allows the user to start the exercise.

FIGS. 21-23 illustrate examples of a breathing exercise chat for one embodiment of a GUI for a mobile application. FIG. 21 illustrates an example of a chat where the chatbot asks if the user wants to complete a breathing exercise. The chatbot allows a user to select a positive or negative response (e.g., yes or no) in response to the question. FIG. 22 illustrates an example of a chat where the user's response to the question in FIG. 21 is recorded. FIG. 23 illustrates an example of a chat where the chatbot allows the user to start the exercise.

Figure 24:
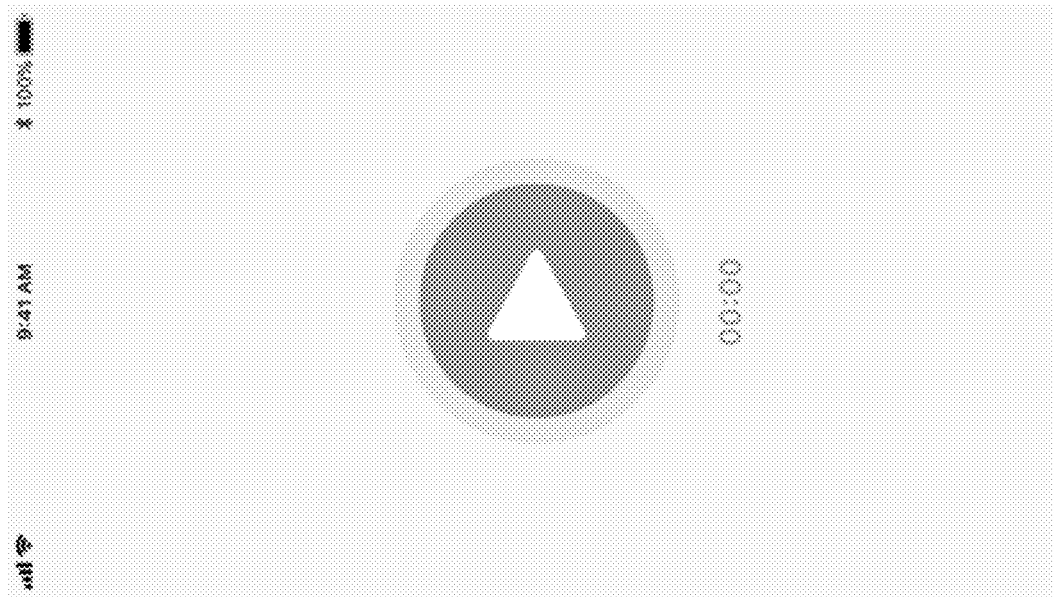
FIG. 24 illustrates an example of a start screen for a breathing exercise.
Figure 26:
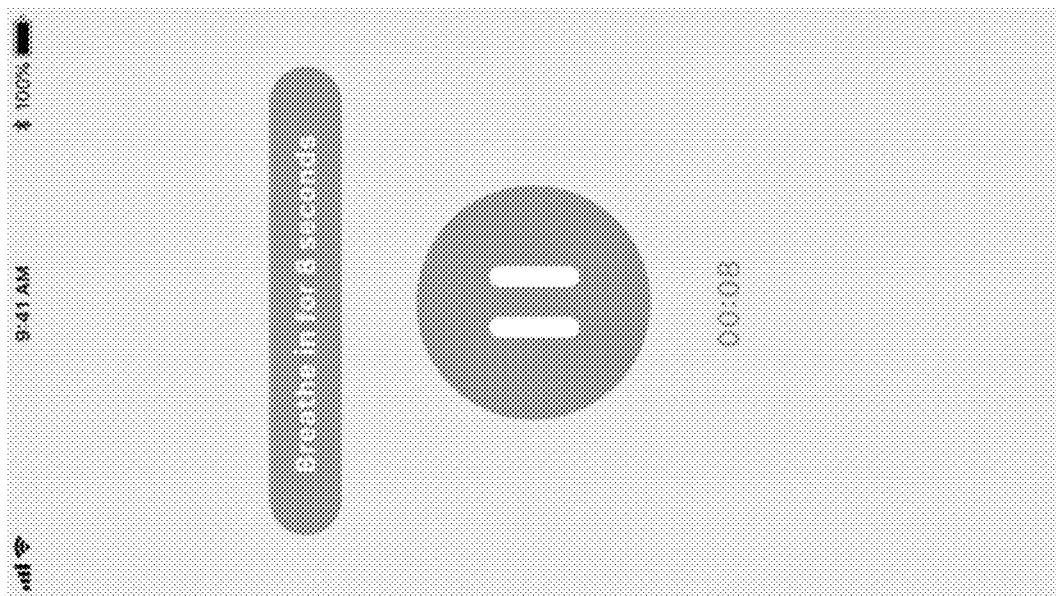
FIG. 26 illustrates another example of a breathing exercise in progress.
Figure 25:
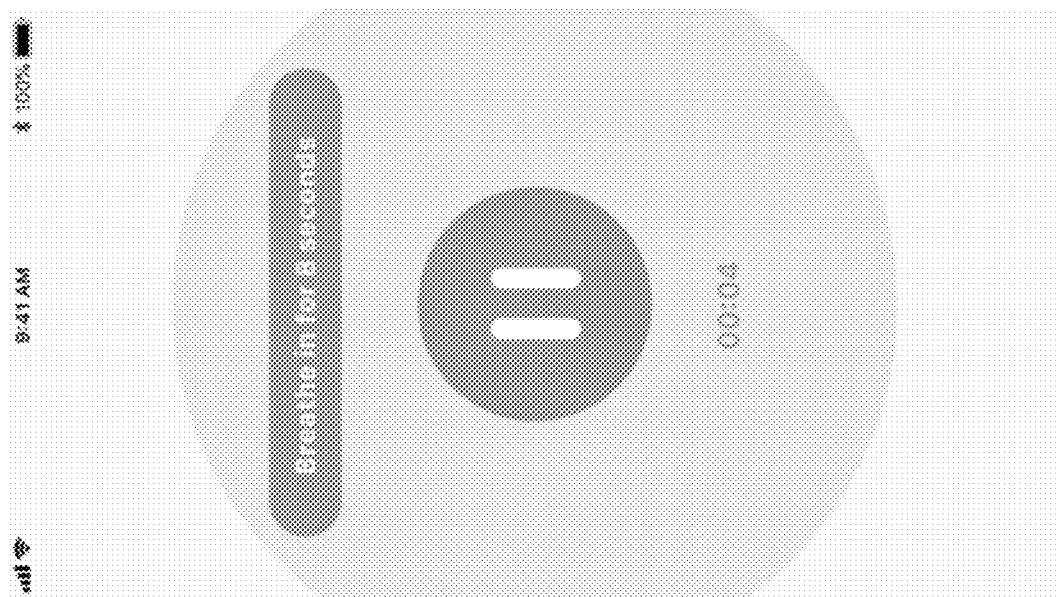
FIG. 25 illustrates an example of a breathing exercise in progress.
Figure 28:
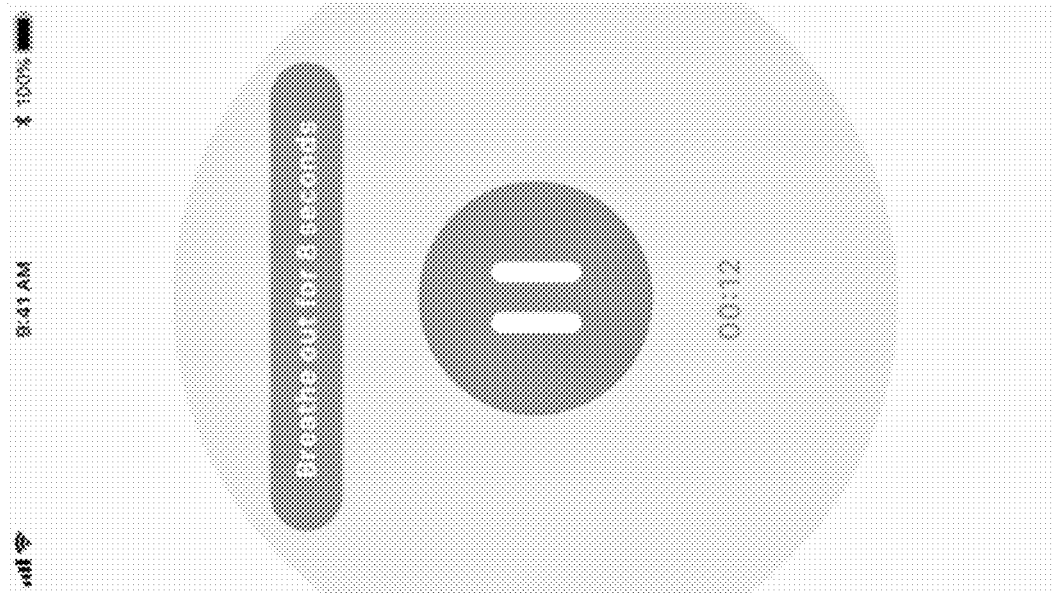
FIG. 28 illustrates still another example of a breathing exercise in progress.
Figure 27:
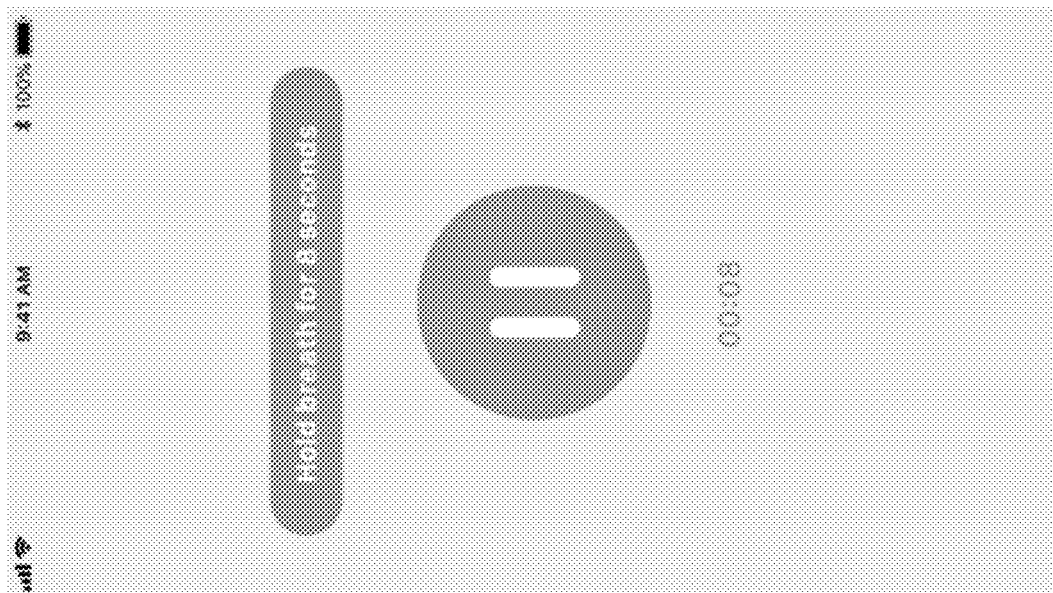
FIG. 27 illustrates yet another example of a breathing exercise in progress.
Figure 29:
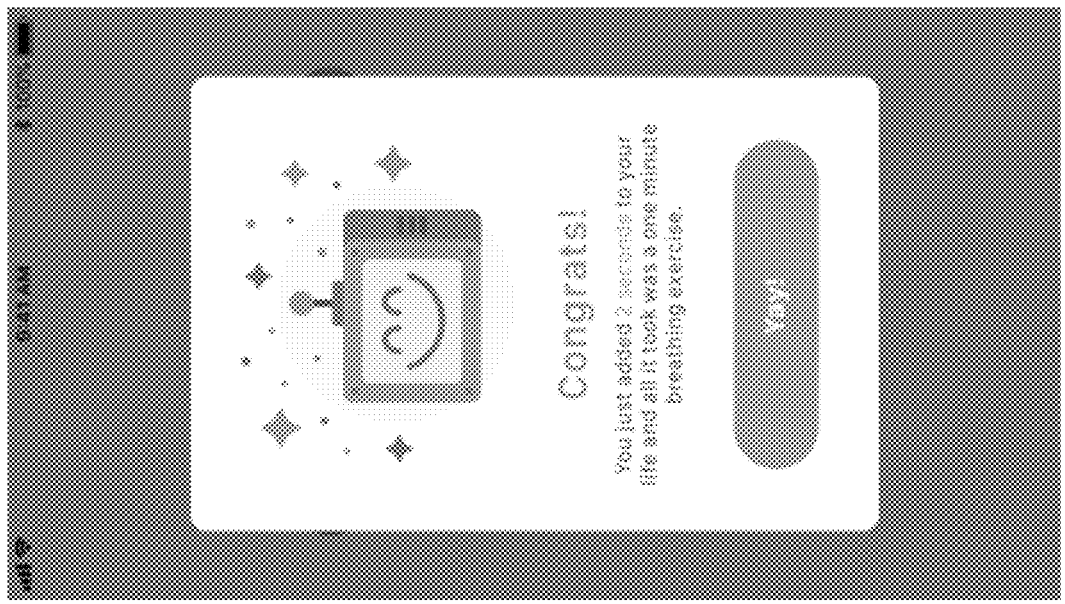
FIG. 29 illustrates a congratulations screen for completing the breathing exercise.

FIGS. 24-29 illustrate examples of a breathing exercise for one embodiment of a GUI for a mobile application. FIG. 24 illustrates an example of a start screen for a breathing exercise. The breathing exercise begins when the play button is pressed. FIG. 25 illustrates an example of a breathing exercise in progress (e.g., 4 seconds into breathing in for 8 seconds). FIG. 26 illustrates another example of a breathing exercise in progress (e.g., 8 seconds into breathing in for 8 seconds). FIG. 27 illustrates yet another example of a breathing exercise in progress (e.g., hold breath for 8 seconds). FIG. 28 illustrates still another example of a breathing exercise in progress (e.g., breathe out for 8 seconds). FIG. 29 illustrates a congratulations screen for completing the breathing exercise.

Figure 30:
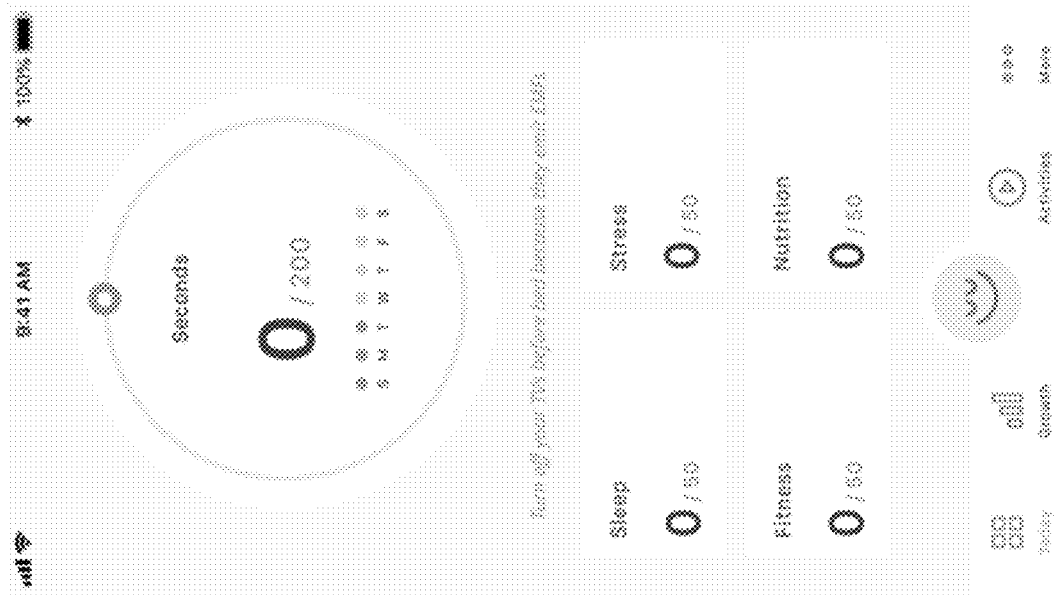
FIG. 30 illustrates an example of a dashboard at the start of a day.
Figure 32:
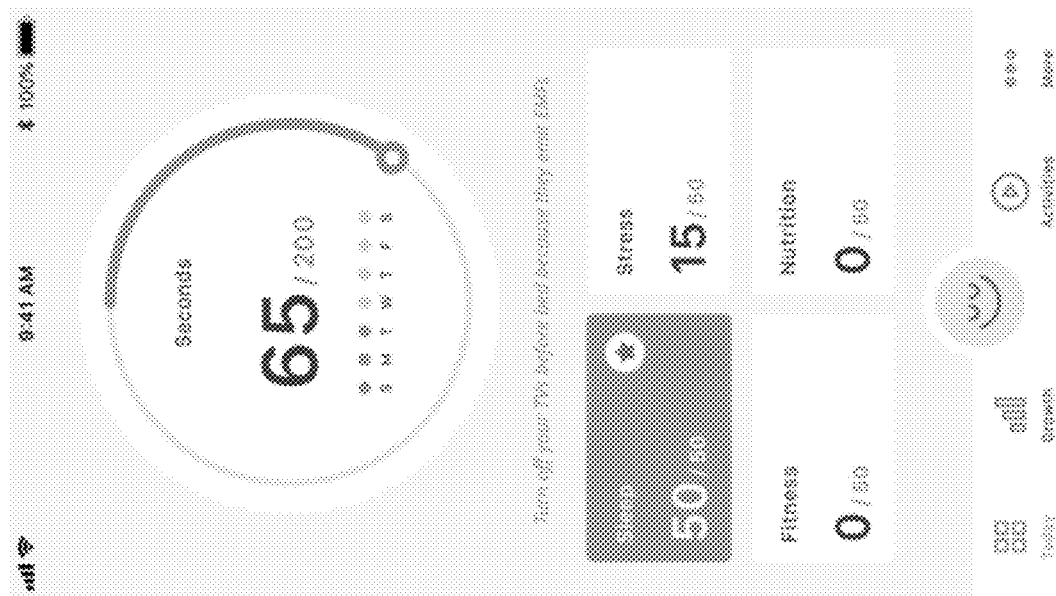
FIG. 32 illustrates an example of a dashboard with 65 seconds added.
Figure 31:
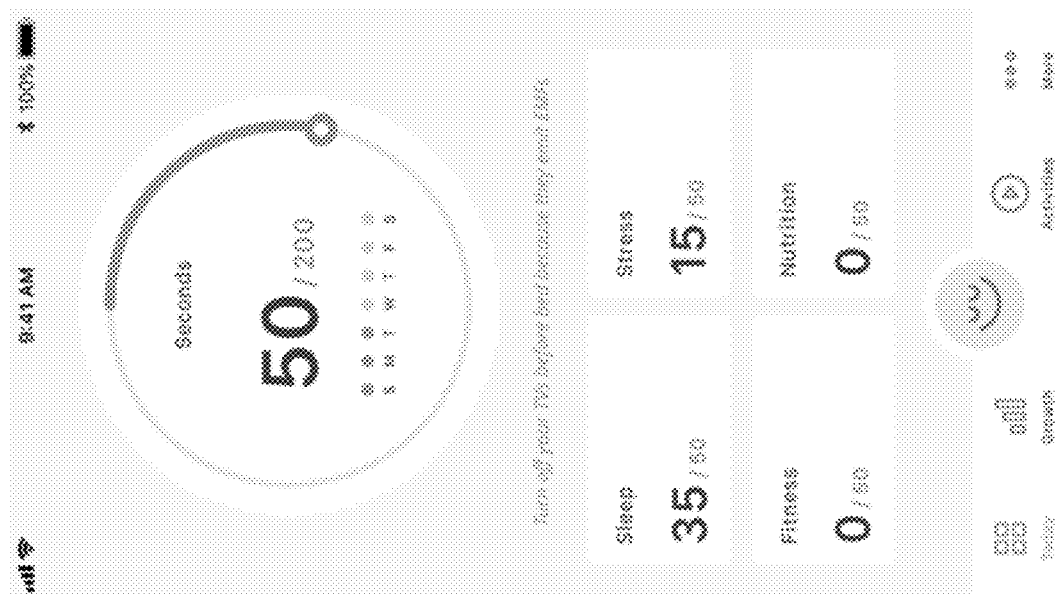
FIG. 31 illustrates an example of a dashboard with 50 seconds added.
Figure 33:
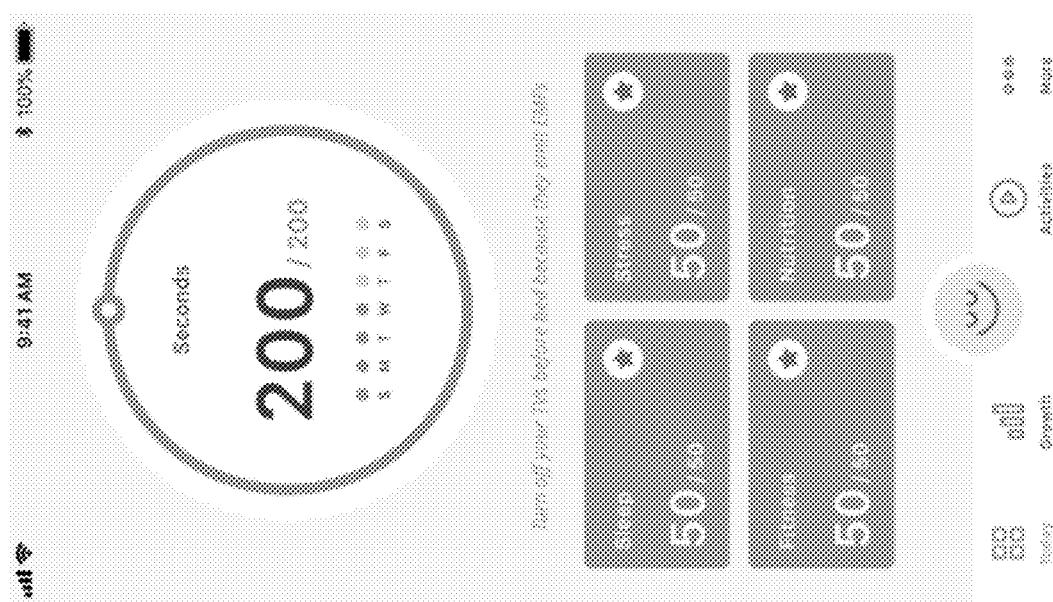
FIG. 33 illustrates an example of a dashboard with 200 seconds added.

FIGS. 30-33 illustrate examples of a dashboard for one embodiment of a GUI for a mobile application. In a preferred embodiment, the mobile application tracks a number of seconds (e.g., 200) added to a life due to healthy choices. FIG. 30 illustrates an example of a dashboard at the start of a day. FIG. 31 illustrates an example of a dashboard with 50 seconds added. FIG. 32 illustrates an example of a dashboard with 65 seconds added. FIG. 33 illustrates an example of a dashboard with 200 seconds added.

Figure 34:
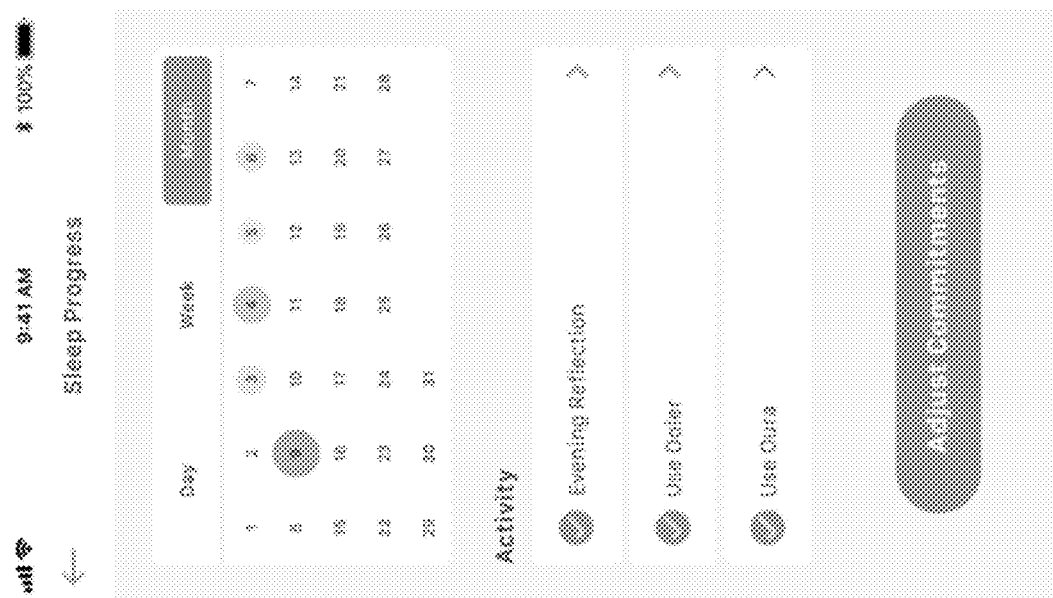
FIG. 34 illustrates an example of a month view of a sleep progress screen.
Figures 35, 36:
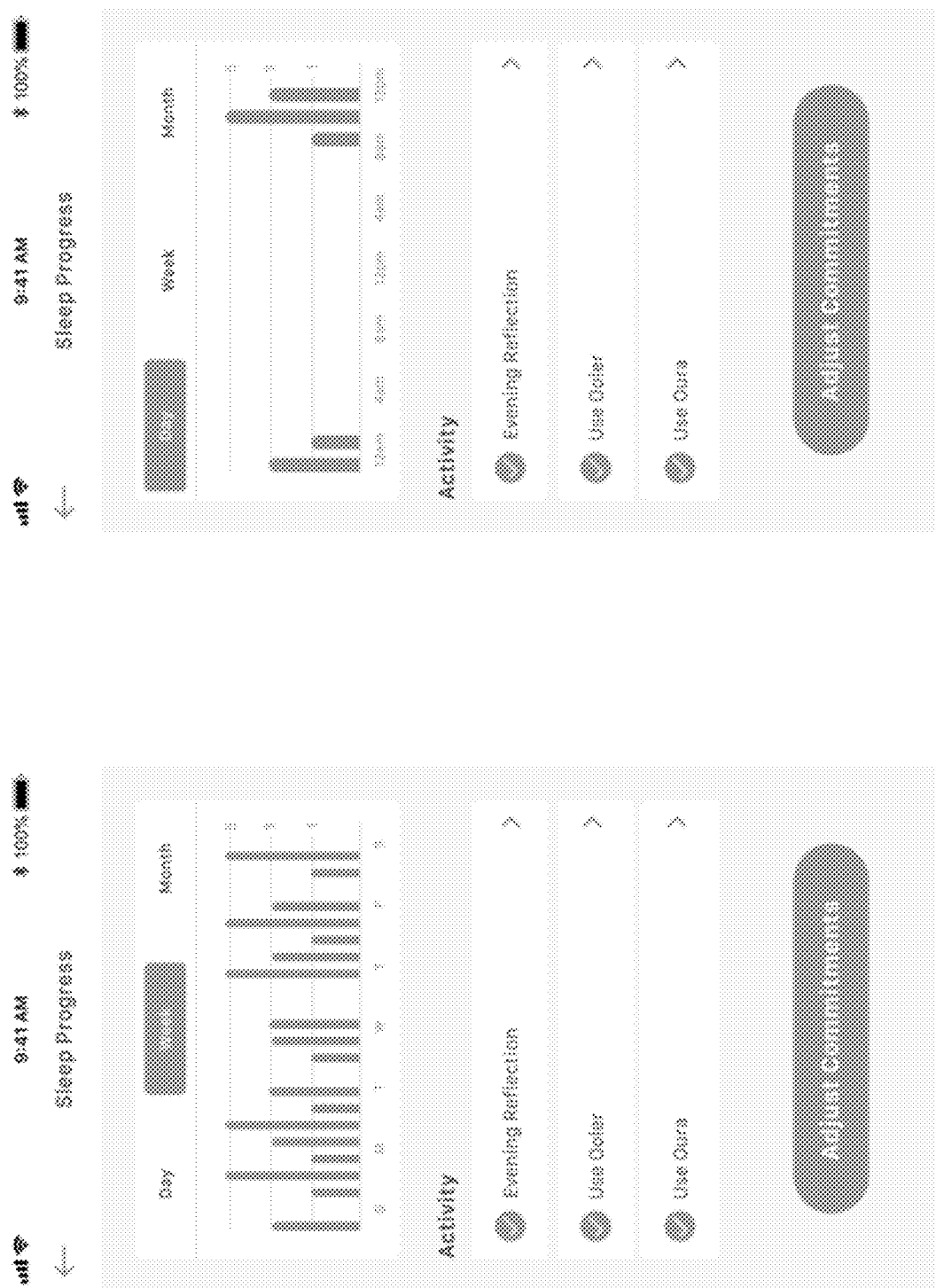
FIG. 35 illustrates an example of a week view of a sleep progress screen.
FIG. 36 illustrates a daily view of a sleep progress screen.

FIGS. 34-36 illustrate examples of a sleep progress screen for one embodiment of a GUI for a mobile application. FIG. 34 illustrates an example of a month view of a sleep progress screen. The sleep progress screen includes links for activities, including, but not limited to, evening reflection, a temperature control device (e.g., OOLER), and a sleep tracker (e.g., OURA). FIG. 35 illustrates an example of a week view of a sleep progress screen. FIG. 36 illustrates a daily view of a sleep progress screen.

The mobile application preferably allows a user to make commitments to activities. The mobile application preferably provides rewards (e.g., points, badges) and/or other incentives for completing activities over a time period. FIGS. 37-38 illustrate examples of a sleep commitment screen for one embodiment of a GUI for a mobile application. FIG. 37 illustrates an example of a sleep commitment screen where an additional 50 seconds are added per day based on the user's commitments. The user is committed to a sleep survey, evening reflection, using a temperature control device (e.g., OOLER), and using a sleep tracker (e.g., OURA). Additionally, the user is able to select daily meditation. FIG. 38 illustrates an example of a sleep commitment screen describing the benefits of using the sleep tracker.

Figure 39:
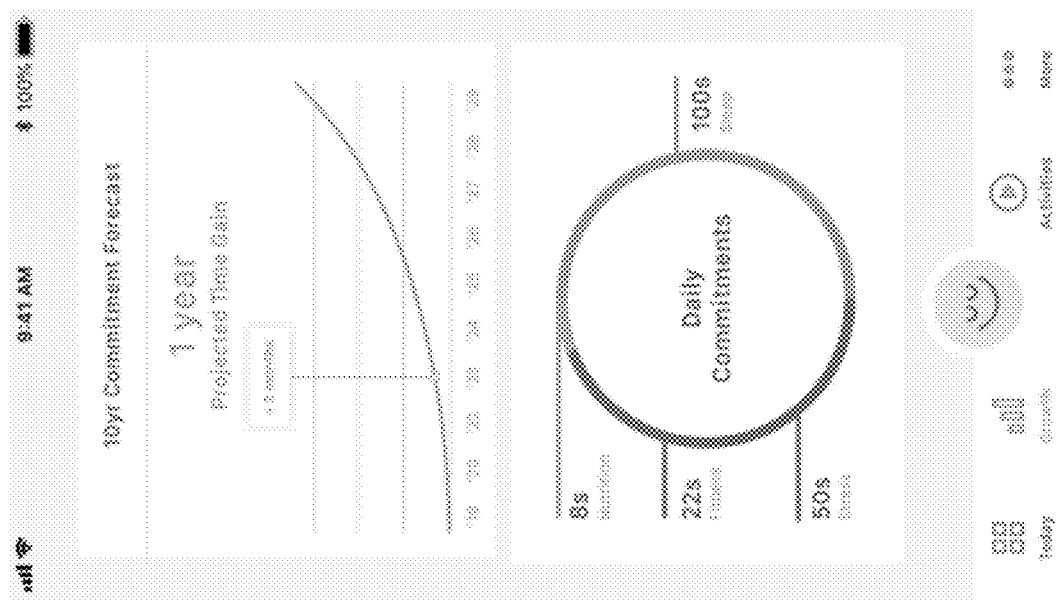
FIG. 39 illustrates an example of a commitment forecast screen for one embodiment of a GUI for a mobile application.

FIG. 39 illustrates an example of a commitment forecast screen for one embodiment of a GUI for a mobile application. In the example shown in FIG. 39, the mobile application projects a 1-year time gain with continual use of the mobile application for a 10-year period. A daily commitment graph illustrates a contribution from nutrition, fitness, stress reduction, and sleep.

Figure 40:
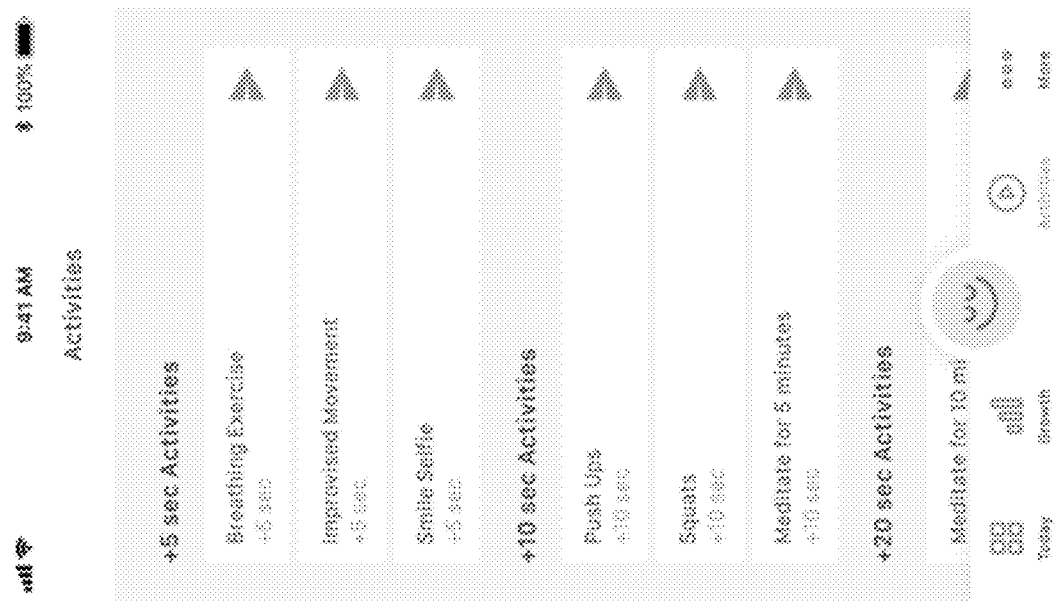
FIG. 40 illustrates an example of an activity screen various activities and scores associated with each activity.
Figure 42:
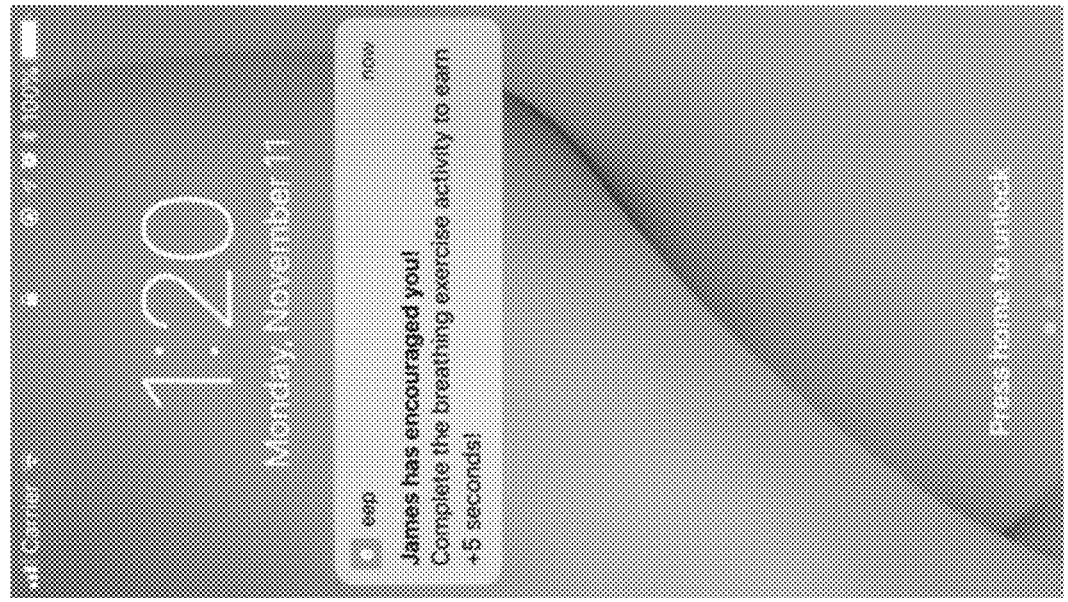
FIG. 42 illustrates an example of an activity challenge notification for one embodiment of a GUI for a mobile application.
Figure 41:
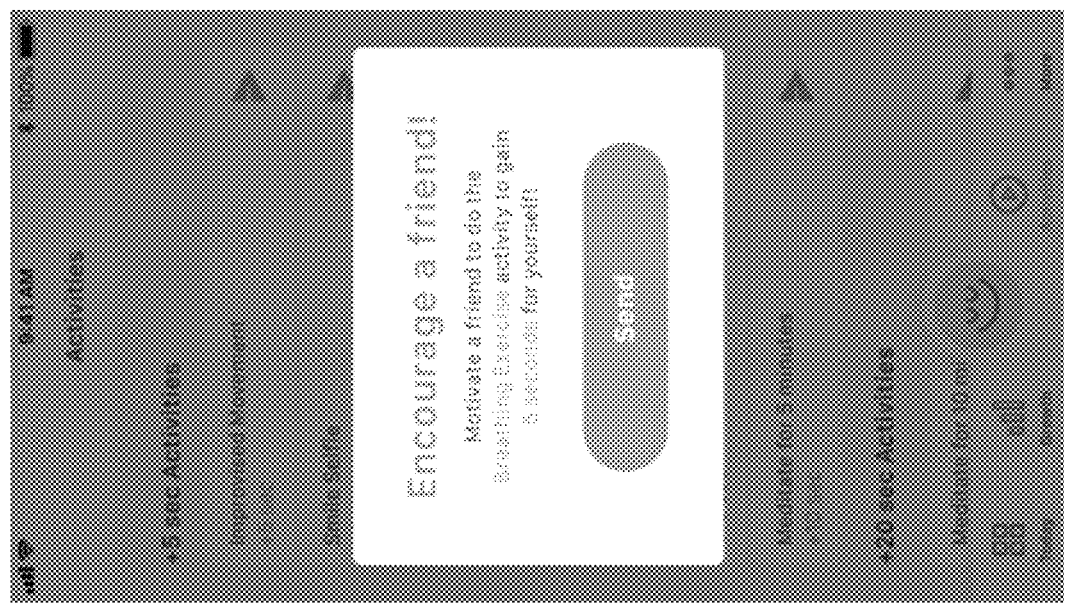
FIG. 41 illustrates an example of sending a challenge to another user to complete an activity.

FIGS. 40-41 illustrate examples of an activity screen for one embodiment of a GUI for a mobile application. FIG. 40 illustrates an example of an activity screen various activities and scores (e.g., in time) associated with each activity. In the example shown in FIG. 40, the activity screen lists 5 second activities (e.g., breathing exercise, improvised movement, smile selfie) and 10 second activities (e.g., push ups, squats, meditation for 5 minutes). The mobile application encourages users to increase minutes of exercise, improve diet, include flexibility training (e.g., yoga) into a regimen of high-intensity interval and/or weight training (e.g., CROSSFIT), walk and/or bike to work, spend time being active with children, watch less television, try aromatherapy, a new supplement, add more minutes of sunshine each day, and spend more time performing good behaviors instead of bad. FIG. 41 illustrates an example of sending a challenge to another user to complete an activity. FIG. 42 illustrates an example of an activity challenge notification for one embodiment of a GUI for a mobile application.

As previously discussed, the mobile application allows a user to challenge another user to complete an activity and/or share an activity with another user. In one embodiment, the mobile application allows a user to share a game that requires motor movement and/or memory utilization with an elderly grandparent. In one example, the user shares a Simon Says game with a grandparent with Parkinson's disease. Daily improvised movement helps to improve mobility, strength, and quality of life. In another example, the mobile application allows a specialist (e.g., doctor, psychologist) to share an exercise in CBT.

In another embodiment, the mobile application allows a user to share data, research, and/or information with another user (e.g., physician, psychologist, coach, nutritionist, friend). In one example, a fitness or sport coach shares data and information with an athlete. In yet another embodiment, the mobile application allows for users to establish group commitments. In one example, a group of people commit to a race, an event, and/or a change in habit. For example, a group of co-workers decide to quit smoking, run a race, and/or lose weight together. The challenges and/or the shared activities in the mobile application provides for accountability within the mobile application and/or outside of the mobile application (e.g., with family and friends).

Figure 44:
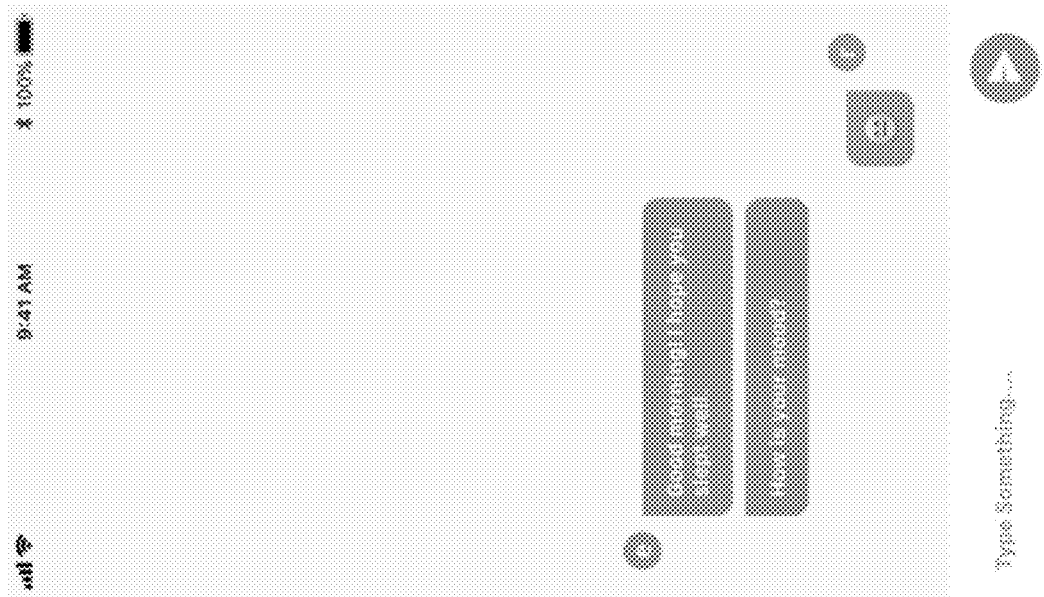
FIG. 44 illustrates an example of a chat where the user's response to the question in FIG. 43 is recorded.
Figure 43:
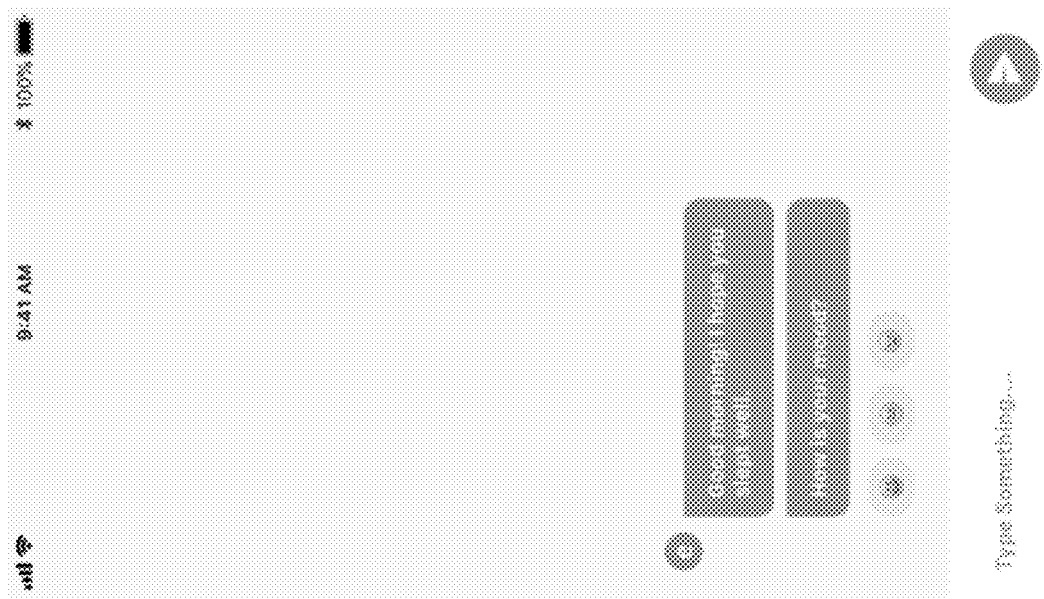
FIG. 43 illustrates an example of a chat where the chatbot asks about the user's mood.
Figure 46:
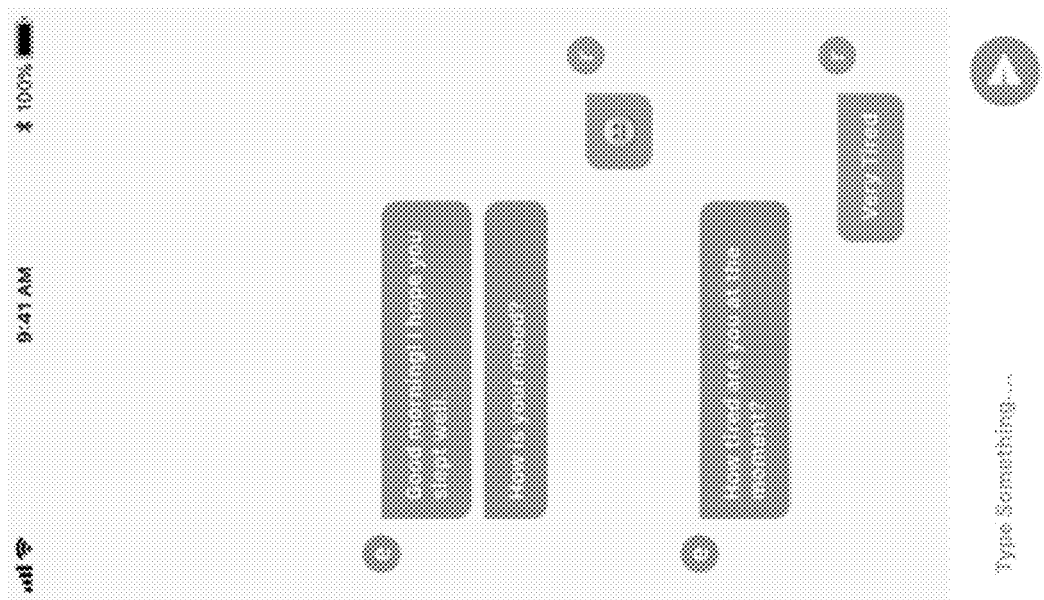
FIG. 46 illustrates an example of a chat where the user's response to the question in FIG. 45 is recorded.
Figure 45:
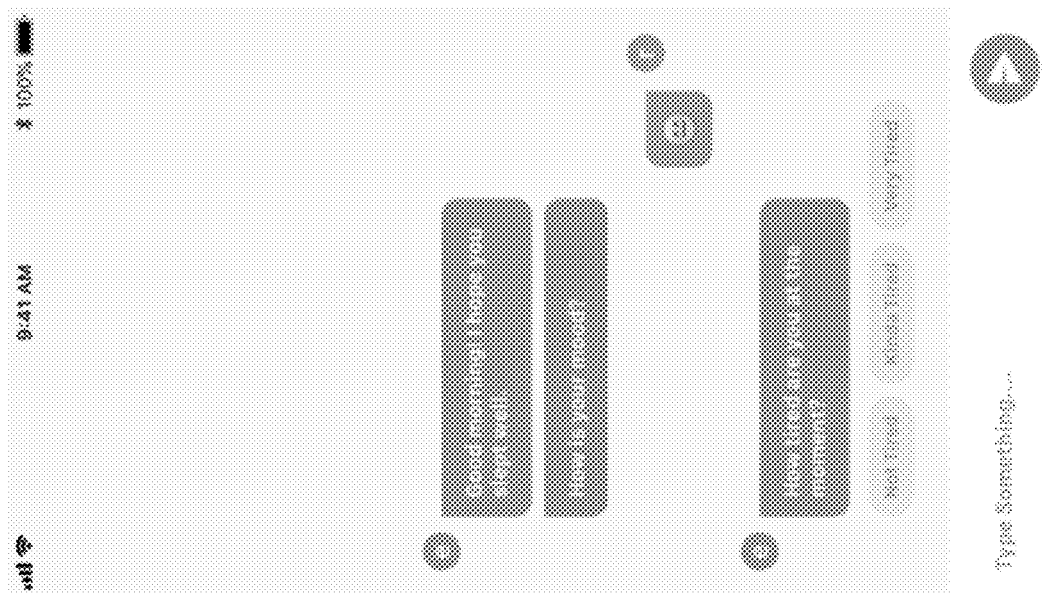
FIG. 45 illustrates an example of a chat where the chatbot asks about how tired the user is at the moment.
Figure 47:
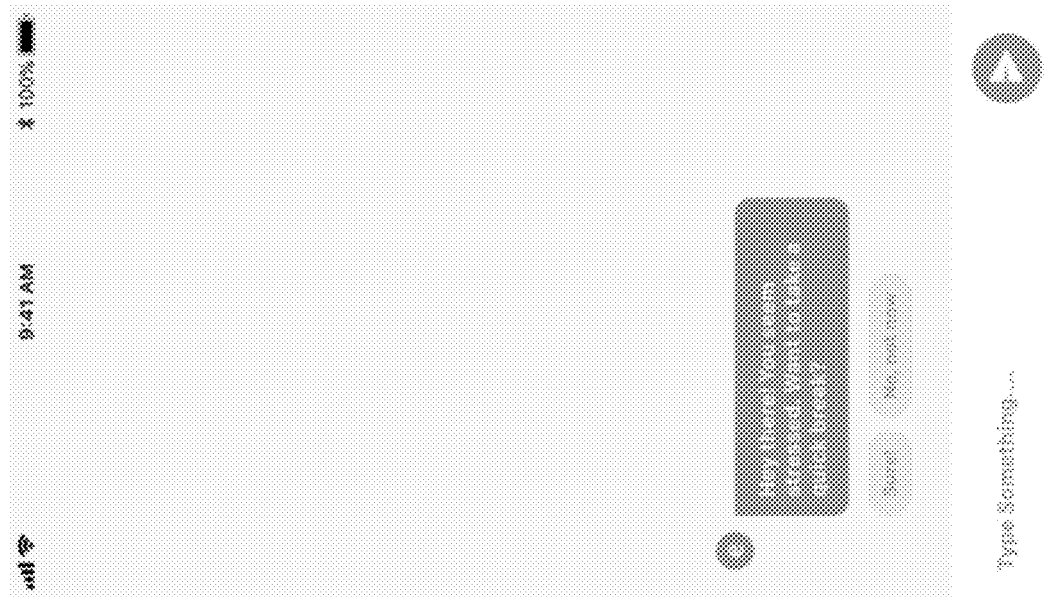
FIG. 47 illustrates an example of a chat where the chatbot includes a health tip about sleep and health.

FIGS. 43-47 illustrate examples of a mood survey chat for one embodiment of a GUI for a mobile application. FIG. 43 illustrates an example of a chat where the chatbot asks about the user's mood. In the example shown in FIG. 43, the chatbot allows the user to select an emoji reflecting the user's mood (e.g., happy, neutral, sad). FIG. 44 illustrates an example of a chat where the user's response to the question in FIG. 43 is recorded. FIG. 45 illustrates an example of a chat where the chatbot asks about how tired the user is at the moment. In the example shown in FIG. 45, the chatbot allows a user to select a response to the question (e.g., not tired, kind of tired, very tired). FIG. 46 illustrates an example of a chat where the user's response to the question in FIG. 45 is recorded. FIG. 47 illustrates an example of a chat where the chatbot includes a health tip about sleep and health.

In one embodiment, the mobile application is operable to determine a user's mood via body sensor data and/or information from third-party applications. For example, if information from a third-party food tracker indicates that a user is eating a significantly higher number of calories for the day, the mobile application asks if the user is stressed. In another example, the mobile application uses data supplied by the EDA sensor to determine changes in emotion (e.g., high skin conductivity indicates a greater amount of sweating due to stress). In yet another example, the mobile application uses data supplied by the heart sensor and movement sensor to determine changes in emotion (e.g., high heart rate with low movement indicates stress). In still another embodiment, the mobile application uses data supplied by the heart sensor to measure stress over time (e.g., decrease in HRV indicates stress, while increase in HRV indicates reduced stress). In one embodiment, the mobile application uses data supplied by the posture sensor determine changes in emotion (e.g., user is slouching, indicating sadness).

The mobile application is preferably operable to display a mood calendar. The mood calendar displays a user's mood over a period of time (e.g., week, month, year). Examples of moods that are tracked using the mobile application include, but are not limited to, joyful, angry, surprised, fearful, sad, disgusted, relaxed, stressed, nervous, upset, depressed, bored, fatigued, relaxed, and happy.

In another embodiment, the mobile application is operable to display a wheel of life. The wheel of life includes, but is not limited to, physical environment, business/career, finances, health, family, friends, romance, personal growth, fun and recreation, emotional health, spiritual health, and/or intellectual challenge. The mobile application allows a user to rate an aspect of the wheel of life (e.g., spiritual health). The mobile application tracks a user's ratings over time. For example, if the rating drops, the mobile application is operable to ask questions to determine the problem and provide suggestions to the user. In one example, the mobile application suggests that a user practice meditation, start a gratitude journal, and/or join a religious study group to improve spiritual health.

Figure 48:
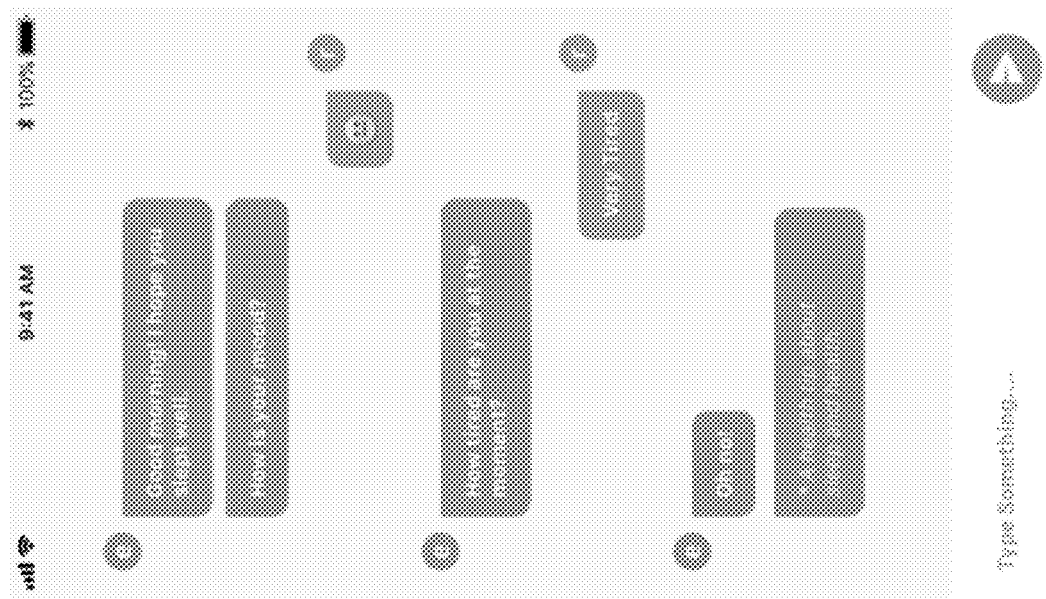
FIG. 48 illustrates an example of a chat where the chatbot observes that the user seems stressed and asks if the user wants to take a break.
Figure 50:
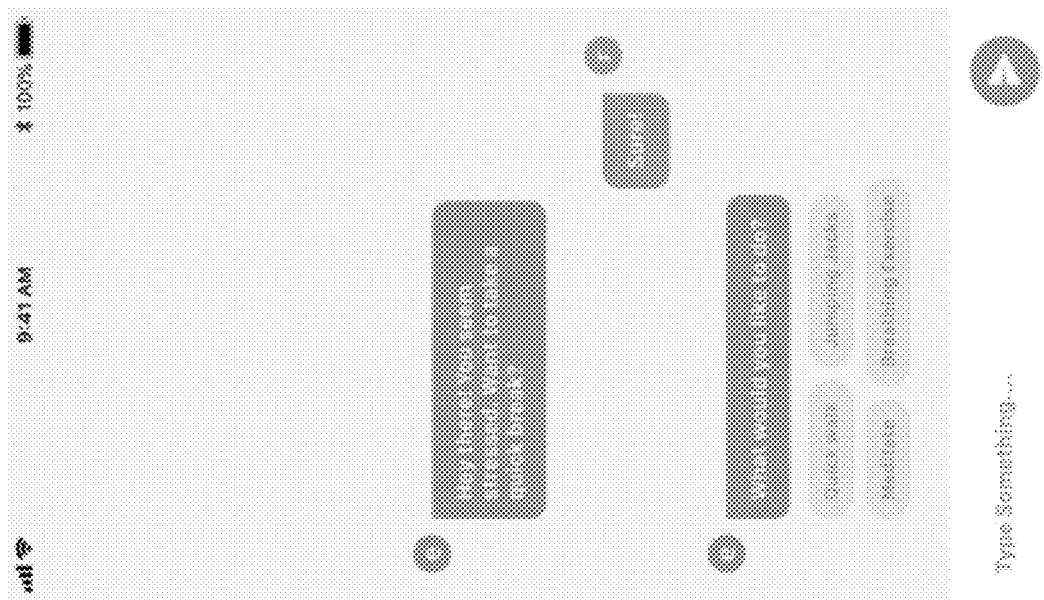
FIG. 50 illustrates an example of a chat where the chatbot asks what activity the user wants to complete.
Figure 49:
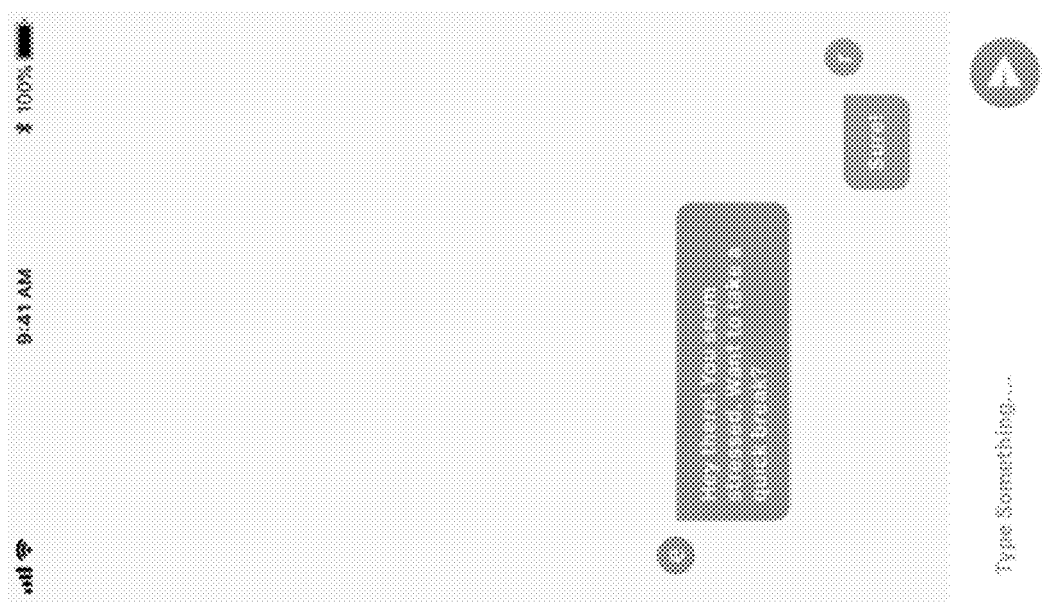
FIG. 49 illustrates an example of a chat where the user's response to the question in FIG. 48 is recorded.
Figure 52:
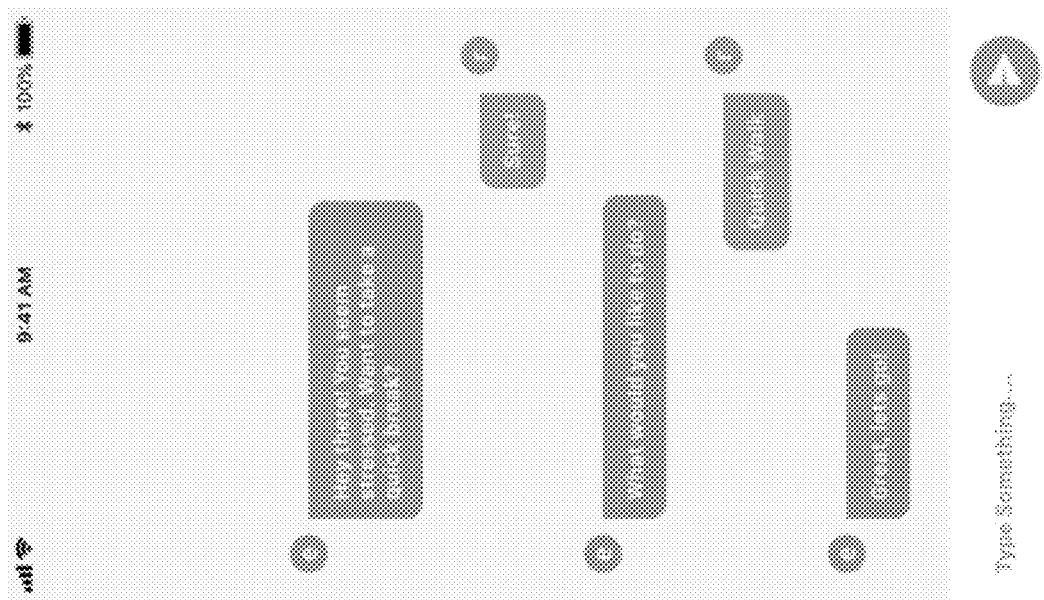
FIG. 52 illustrates an example of a chat where the chatbot encourages the user to participate in the activity.
Figure 51:
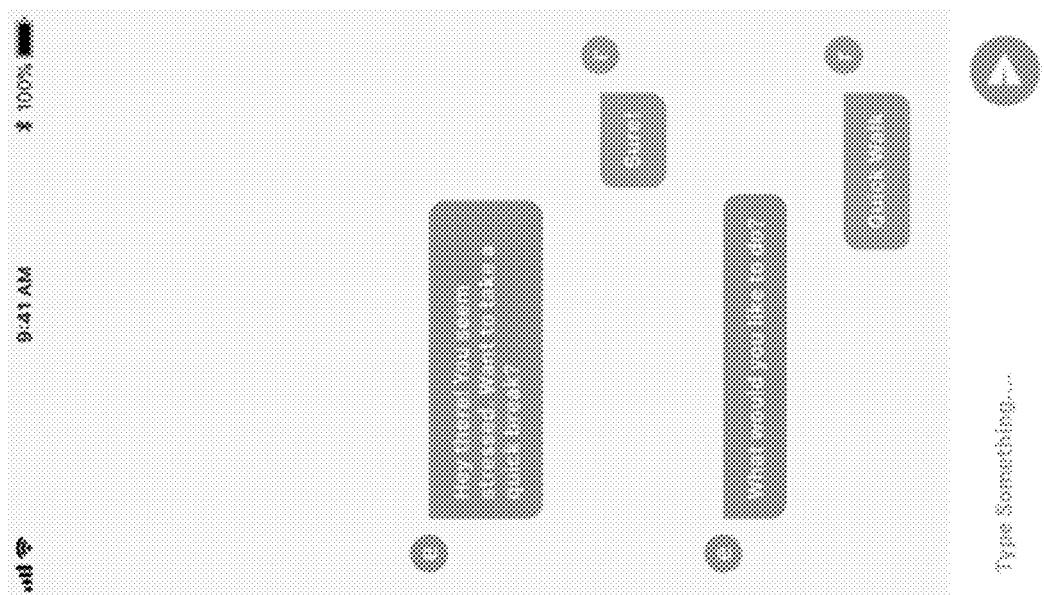
FIG. 51 illustrates an example of a chat where the user's response to the question in FIG. 50 is recorded.

FIGS. 48-52 illustrate examples of a stress break chat for one embodiment of a GUI for a mobile application. FIG. 48 illustrates an example of a chat where the chatbot observes that the user seems stressed and asks if the user wants to take a break. In the example shown in FIG. 48, the chatbot allows the user to select a response to the question (e.g., yes, no). FIG. 49 illustrates an example of a chat where the user's response to the question in FIG. 48 is recorded. FIG. 50 illustrates an example of a chat where the chatbot asks what activity the user wants to complete. In the example shown in FIG. 50, the chatbot allows the user to select a response to the question (e.g., quick walk, meditate, jumping jacks, breathing exercise). FIG. 51 illustrates an example of a chat where the user's response to the question in FIG. 50 is recorded. FIG. 52 illustrates an example of a chat where the chatbot encourages the user to participate in the activity.

Figure 54:
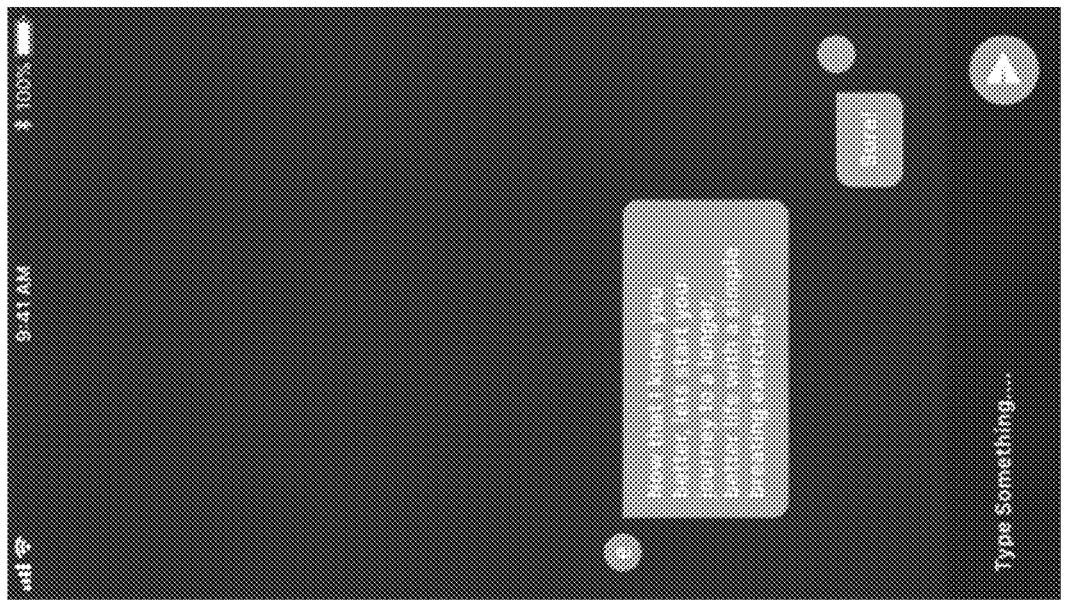
FIG. 54 illustrates an example of a chat where the user's response to the question in FIG. 53 is recorded.
Figure 53:
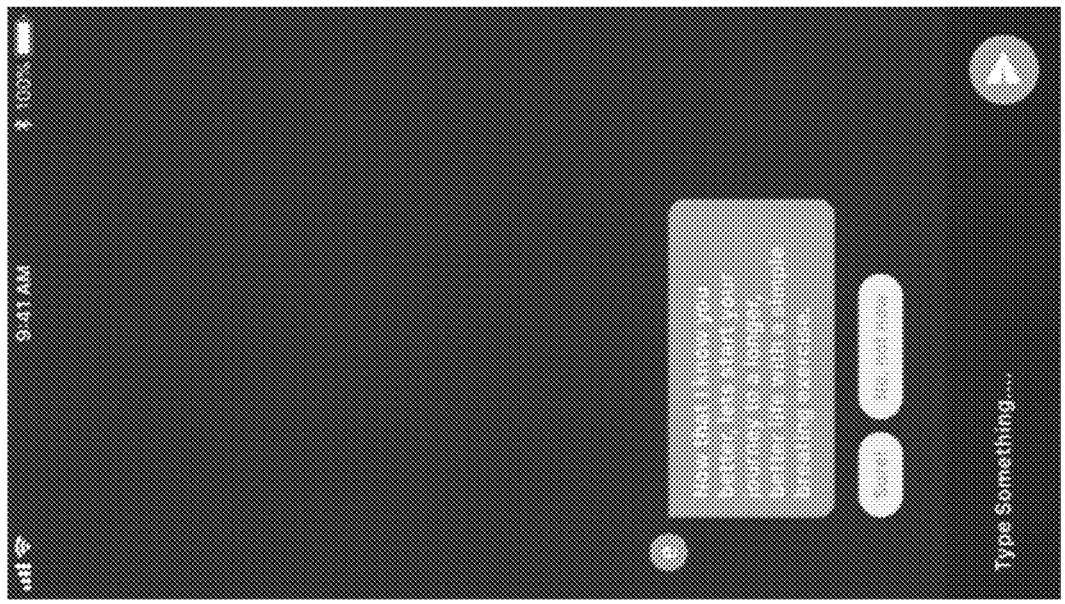
FIG. 53 illustrates an example of a night mode chat where the chatbot asks if the use wants to do a breathing exercise.

FIGS. 53-54 illustrate examples of a night mode screen for one embodiment of a GUI for a mobile application. Advantageously, the GUI has a black background, which prevents the user from being exposed to large amounts of blue light. Blue light often suppresses melatonin production and make it more difficult to sleep. FIG. 53 illustrates an example of a night mode chat where the chatbot asks if the use wants to do a breathing exercise. In the example shown in FIG. 53, the chatbot allows the user to select a response to the question (e.g., yes, no). FIG. 54 illustrates an example of a chat where the user's response to the question in FIG. 53 is recorded.

Figure 56:
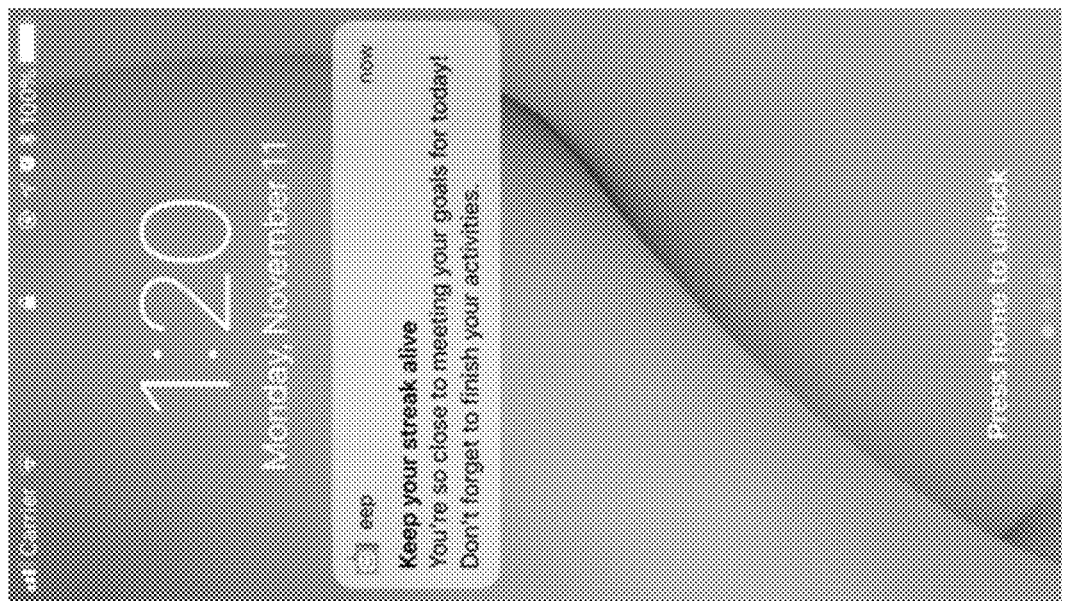
FIG. 56 illustrates an example of the mobile application sending a push notification to remind a user to complete activities to a mobile device.
Figure 55:
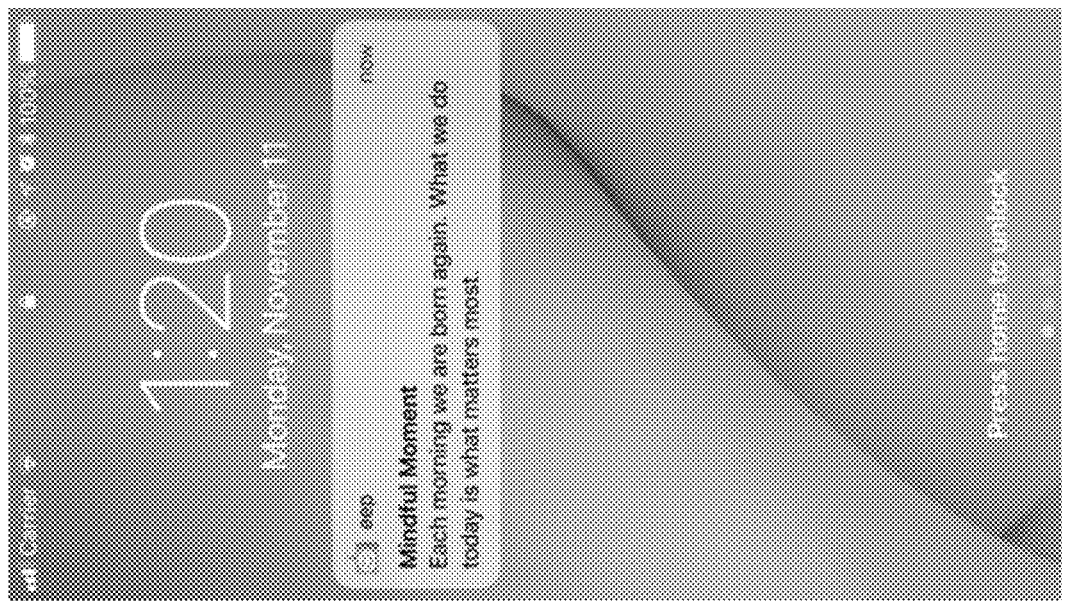
FIG. 55 illustrates an example of the mobile application sending a push notification about mindfulness to a mobile device.
Figure 58:
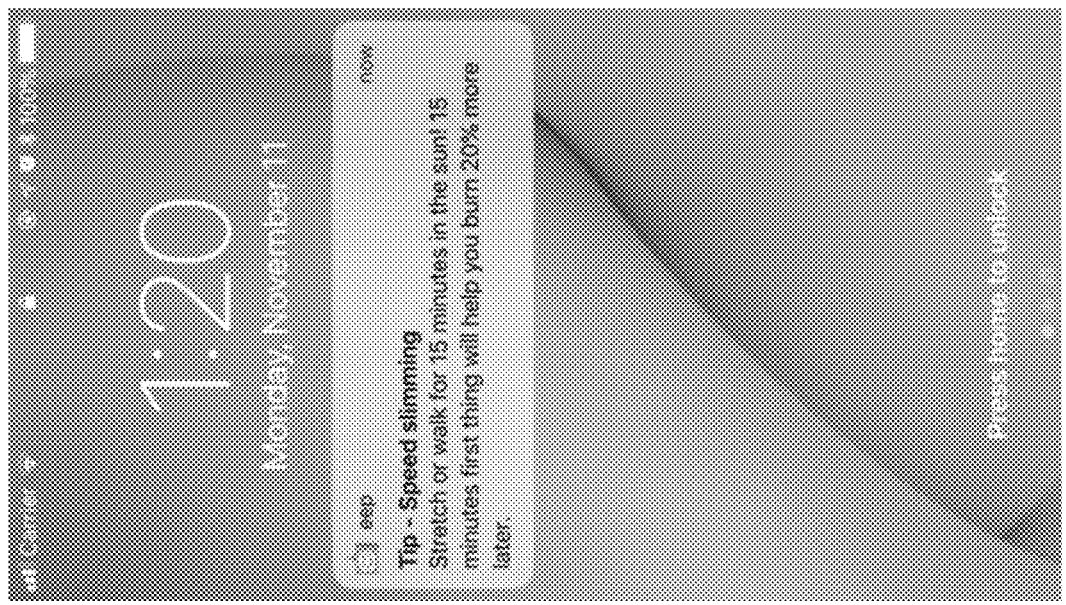
FIG. 58 illustrates an example of the mobile application sending a push notification regarding fitness to a mobile device.
Figure 57:
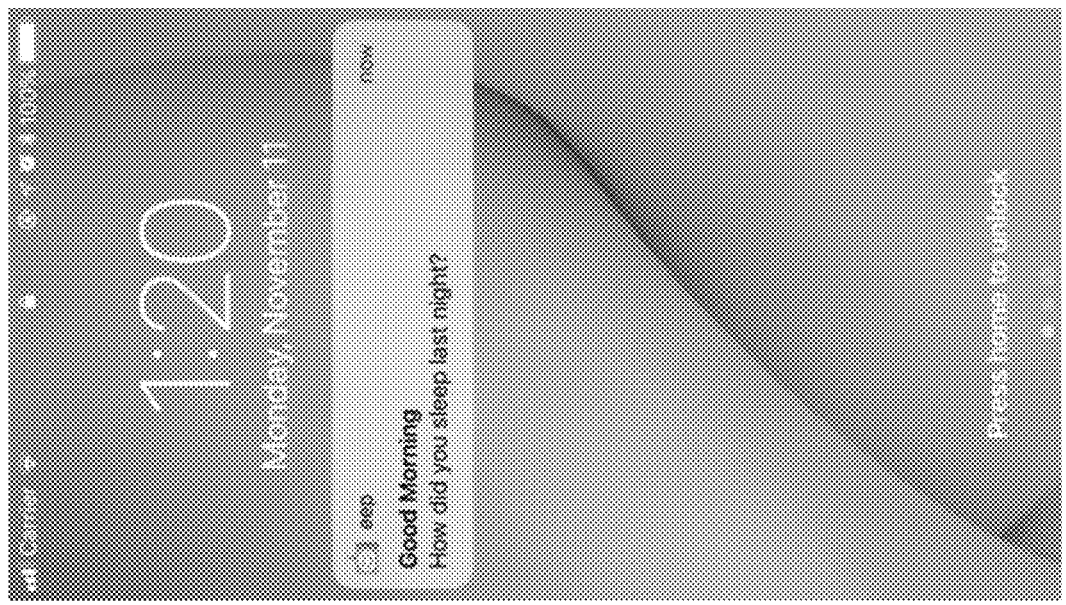
FIG. 57 illustrates an example of the mobile application sending a push notification regarding a sleep survey to a mobile device.
Figure 60:
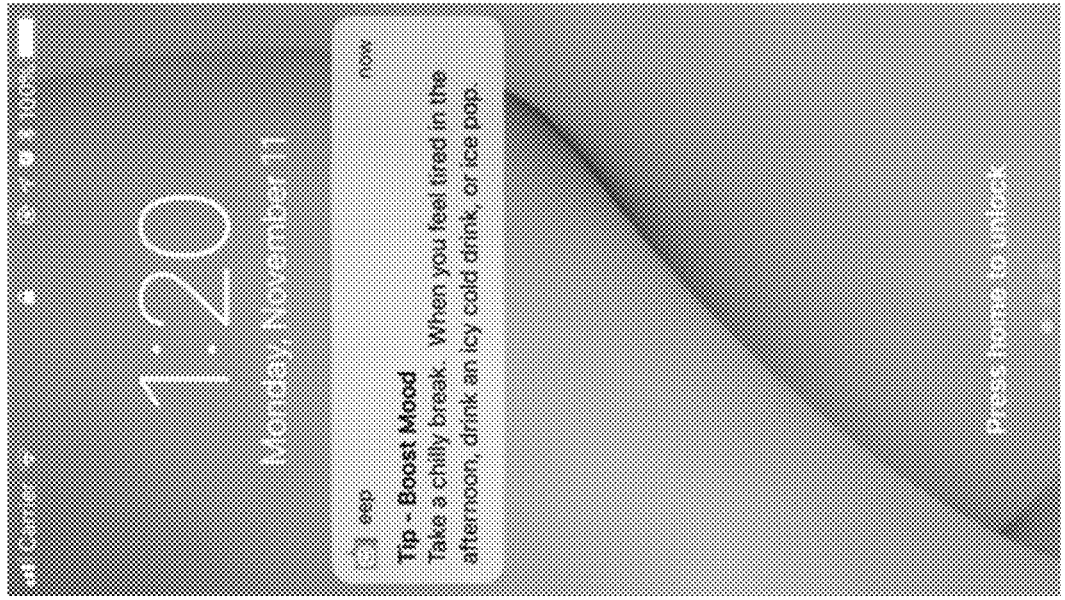
FIG. 60 illustrates an example of the mobile application sending a push notification with a mood boosting tip to a mobile device.
Figure 59:
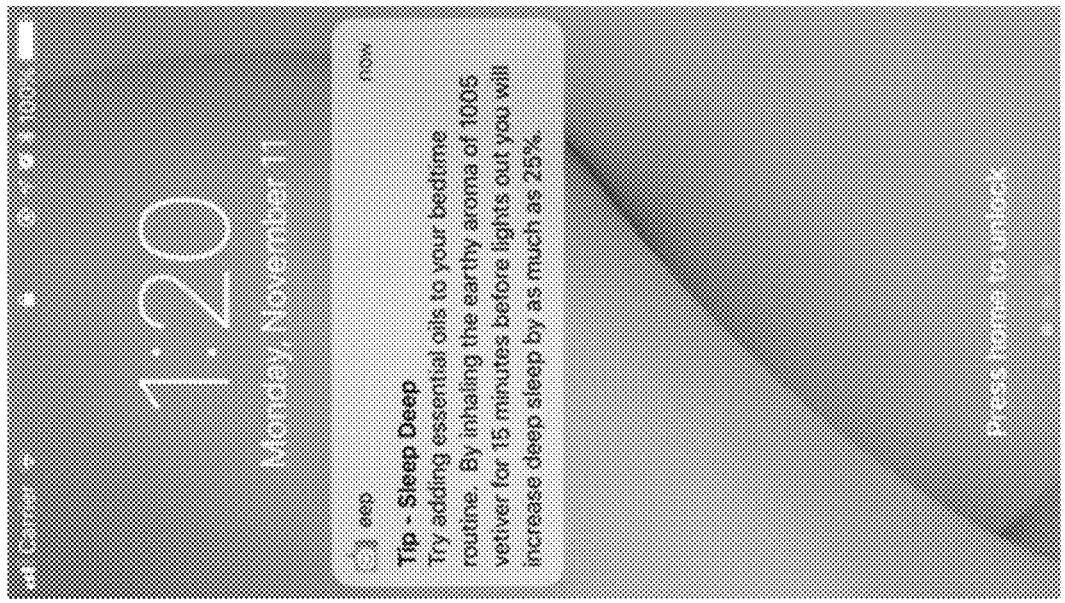
FIG. 59 illustrates an example of the mobile application sending a push notification with a sleep tip to a mobile device.
Figure 62:
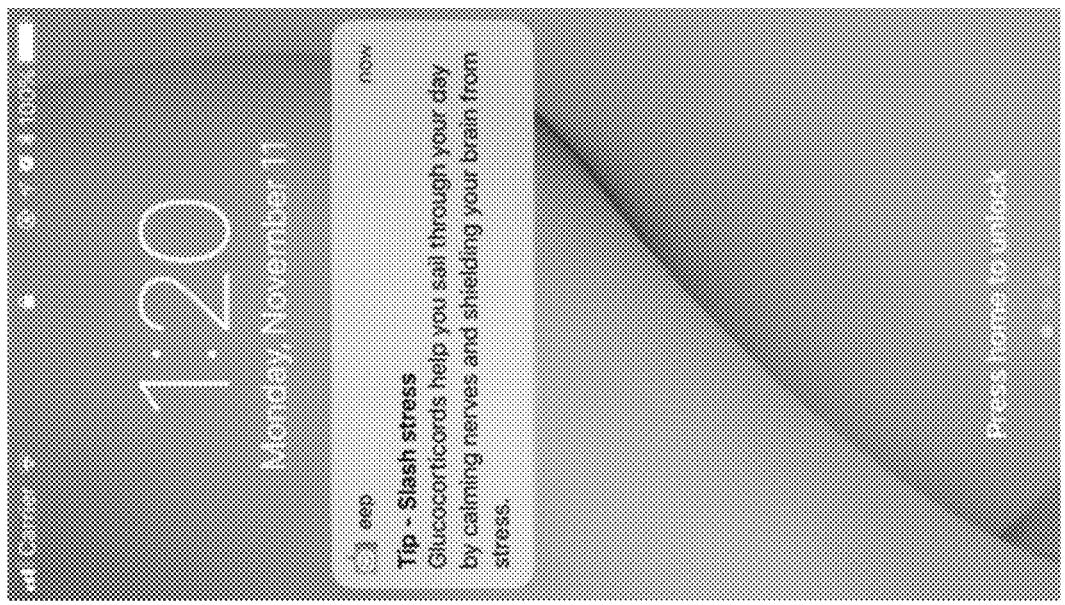
FIG. 62 illustrates an example of the mobile application sending a push notification with a focus improvement tip to a mobile device.
Figure 61:
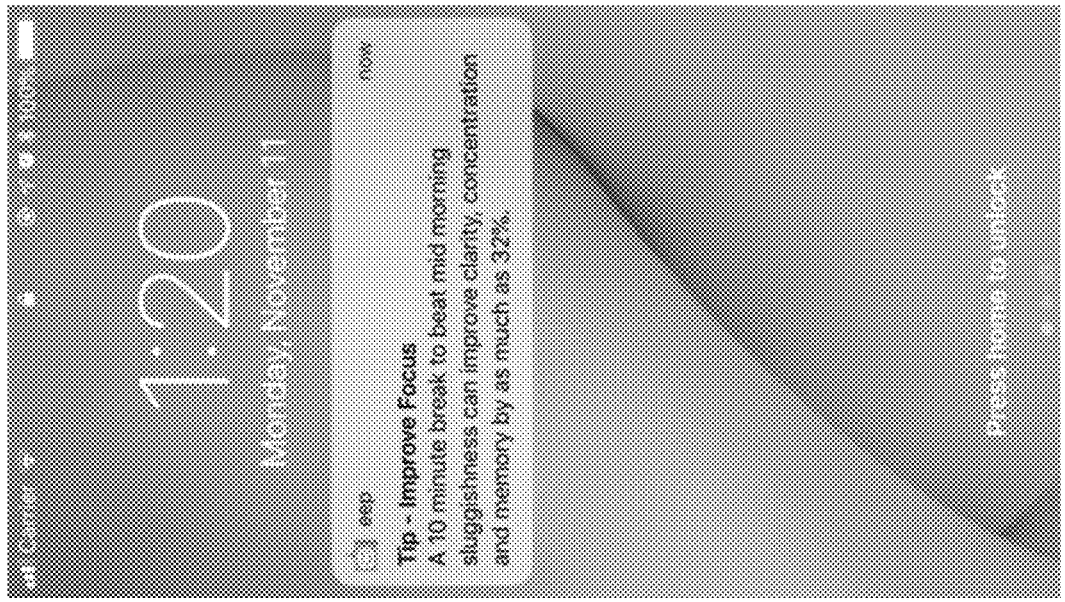
FIG. 61 illustrates an example of the mobile application sending a push notification with a stress relieving tip to a mobile device.

FIGS. 55-62 illustrate examples of push notifications to a mobile device. In FIG. 55, the mobile application sends a push notification about mindfulness to a mobile device. In FIG. 56, the mobile application sends a push notification to remind a user to complete activities to a mobile device. In FIG. 57, the mobile application sends a push notification regarding a sleep survey to a mobile device. In FIG. 58, the mobile application sends a push notification regarding fitness to a mobile device. In FIG. 59, the mobile application sends a push notification with a sleep tip to a mobile device. In FIG. 60, the mobile application sends a push notification with a mood boosting tip to a mobile device. In FIG. 61, the mobile application sends a push notification with a stress relieving tip to a mobile device. In FIG. 62, the mobile application sends a push notification with a focus improvement tip to a mobile device.

Figure 64:
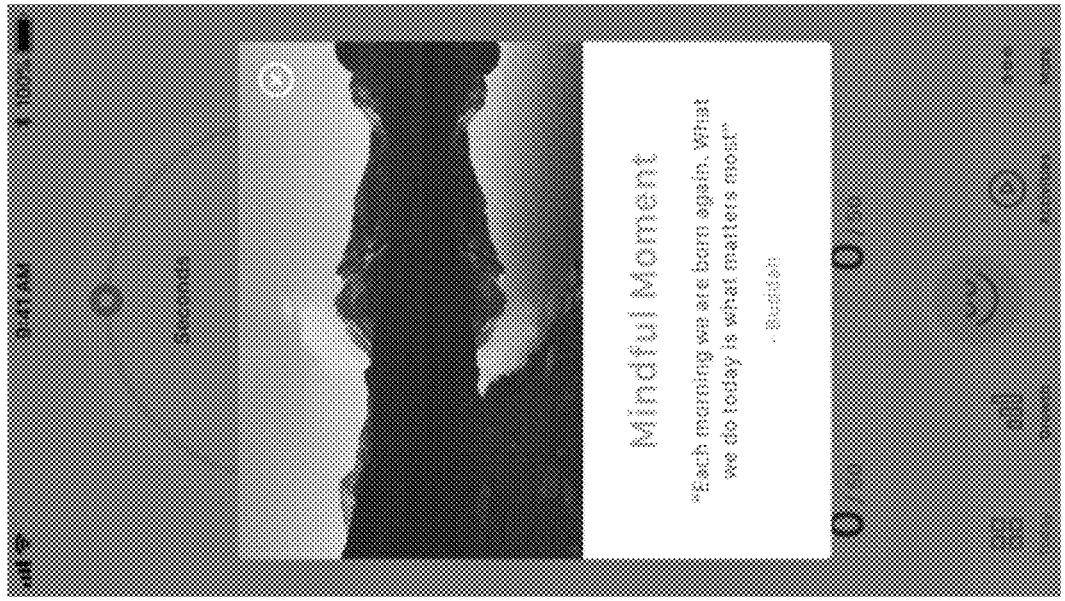
FIG. 64 illustrates a detail screen of the push notification in FIG. 55.
Figure 63:
FIG. 63 illustrates a detail screen of the push notification in FIG. 58.

FIG. 63 illustrates a detail screen of the push notification in FIG. 58. FIG. 64 illustrates a detail screen of the push notification in FIG. 55.

Figure 65:
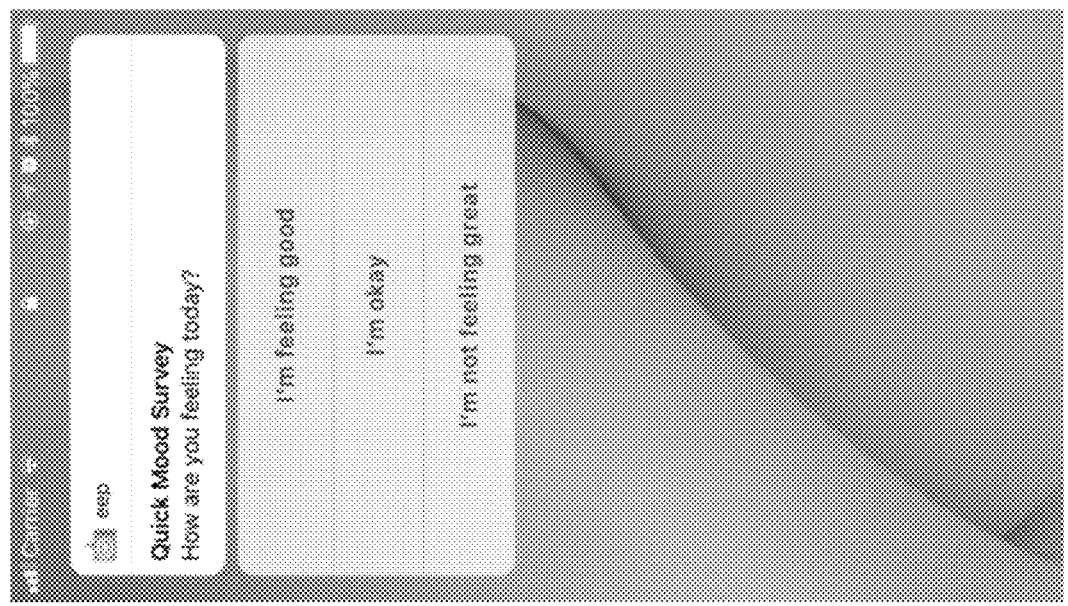
FIG. 65 illustrates an example of an interactive push notification.

FIG. 65 illustrates an example of an interactive push notification. In the example shown in FIG. 65, the mobile application asks the user to complete a mood survey. The push notification provides selectable responses to the question (e.g., good, okay, not good). Advantageously, the interactive push notification allows the mobile application to acquire data about the user directly from the interactive push notification without having to open the mobile application.

In one embodiment, the mobile application is on a smartphone or a tablet. The mobile application is preferably operable to interface with a camera on the smartphone or the tablet. In one embodiment, the mobile application is operable to estimate gender, age, and/or body mass index (BMI) from an image (e.g., a selfie) taken with the camera. In another embodiment, the mobile application is operable to detect chronic disease, alcohol use, and/or evidence of smoking from the image. In yet another embodiment, the mobile application is operable to age progress an image. In still another embodiment, the mobile application is operable to detect an emotion from a facial expression in the image. In one embodiment, the emotion includes, but is not limited to, joy, anger, fear, disgust, contempt, sadness, and/or surprise. The mobile application uses computer vision algorithms to perform facial analysis. In one embodiment, the mobile application uses the International Affective Picture System (TAPS) to determine a user's emotion. Examples of facial analysis software are disclosed in U.S. Pat. Nos. 9,646,046, 9,317,740, 9,311,564, 9,177,230, 9,152,845, 9,147,107, 9,008,416, 8,913,839, 8,818,111, 8,780,221, 8,705,875, and 8,676,740 and U.S. Patent Publication Nos. 2017/0105568, 2014/0242560, and 2013/0158437, each of which is incorporated herein by reference in its entirety.

In another embodiment, the mobile application is operable to recognize an emotion based on a user's voice. Examples of voice analysis software are disclosed in U.S. Pat. Nos. 9,786,299, 8,965,770, 7,940,914, 7,451,079, and 7,340,393 and U.S. Patent Publication Nos. 2018/0005646 and 2015/0310878, each of which is incorporated herein by reference in its entirety. In yet another embodiment, the mobile application is operable to classify at least one health state or condition from a voice sample, such as disclosed in U.S. Pat. No. 10,475,530 and U.S. Patent Publication No. 2018/0254041, each of which is incorporated herein by reference in its entirety.

In still another embodiment, the mobile application is operable to educate a user. In one embodiment, the mobile application is operable to incorporate data from at least one genetic test (e.g., ANCESTRYDNA, 23 ANDME). Based on the at least one genetic test, the mobile application is operable to inform a user about health habits (e.g., diet, supplements) that will optimize the user's future health. In one example, the mobile application advises a user that a lack of sleep, too much stress, and the results of the at least one genetic test indicate that the user is predisposed to diabetes and/or autoimmune disorders.

The mobile application is also operable to manage exchanges between a user and their environment. In one example, the mobile application notes that the user's commute time is negatively impacting their stress level. In another example, the mobile application notes that interaction with an individual raises their stress level (e.g., toxic relationship). In yet another example, the mobile application is operable to detect a negative impact of social media use on the user. The mobile application advises a user to minimize time on social media due to the negative impact (e.g., measured through stress responses by the EDA and/or heart sensors). The mobile application preferably identifies these exchanges and coaches the user to minimize stress. The mobile application is also operable to identify positive influences. In one example, the mobile application identifies at least one individual that positively impacts a user's stress level. When the user is stressed out, the mobile application suggests that the user contact the at least one individual for support.

In yet another embodiment, the system is a decentralized platform utilizing blockchain technology. The decentralized platform is operable to store information regarding the user's health, sleep, and stress levels. In one embodiment, the data blocks within the chain are encrypted using cryptography. Individual users are able to grant access to their data by providing another individual (e.g., healthcare provider) with a private password or key. The blockchain-based decentralized platform provides security for peer-to-peer sharing of medical information by preventing unauthorized access to the user's private medical information.

As previously stated, the user is able to grant access to their data to third parties (e.g., healthcare provider, psychologist, nutritionist, fitness coach, researchers). In one embodiment, the system allows the user to be compensated (e.g., micropayments) for sharing the user's data. In another embodiment, the system provides information to the user regarding clinical trials for medical conditions. In yet another embodiment, the system allows researchers to initially screen users to determine if a user is potentially eligible for a clinical trial. The system also allows insurance companies and/or employers to reward users for positive behaviors (e.g., sleep goals, nutrition goals, fitness goals).

The system preferably determines a chronotype for a user. In one embodiment, the chronotype includes, but is not limited to, morning person, less morning person, neither morning person or night owl, less night owl, and/or night owl. Alternatively, the chronotype includes dolphin, bear, lion, and/or wolf. In one embodiment, the chronotype is determined by a genetic test. In another embodiment, the chronotype is determine by measuring body temperature. For example, a dolphin experiences an increase in core body temperature at night, a morning person/a lion experiences a core body temperature drop around 7:00 pm, a neither morning person or night owl/a bear experiences a core body temperature drop around 9:00 pm, and a night owl/a wolf experiences a core body temperature drop around 10:00 pm. In yet another embodiment, the system determines the chronotype using a self-assessment quiz. FIG. 66 illustrates one embodiment of a quiz to determine chronotype.

In a preferred embodiment, the at least one remote device schedules at least one event or task (e.g., workout, meeting, test, meal, bedtime, wakeup time) based on the chronotype. In one embodiment, the system is operable to interact with at least one calendar on the at least one remote device. In one example, the mobile application suggests a morning person/a lion exercise between 5:00-6:00 pm to increase energy. In another example, the mobile application suggests that a neither morning person nor night owl/a bear refrain from eating after 8:00 μm. In yet another example, the mobile application suggests that a neither morning person nor night owl/a bear not consume caffeine until 9:30-10:00 am.

In a preferred embodiment, the system includes lifestyle assessment questions. In one embodiment, the lifestyle assessment questions include, but are not limited to, a preferred wake up time, a preferred bedtime, alarm clock usage, a time spent in bed prior to falling asleep (e.g., sleep latency), a time spent in bed prior to getting out of bed (e.g., sleep inertia), bed sharing status (i.e., user shares a bed with at least one other individual or pet), exposure to light (e.g., natural light outdoors, blue light, light emitting diodes (LEDs)), a work schedule (e.g., start time, end time, lunch break, days of the week, shift work, commute times), a travel schedule (e.g., time zone changes), financial information (e.g., budget for interventions, budget for joining a gym), and/or household information (e.g., children, ages of children, chronotype of children, spouse or partner, chronotype of spouse or partner). In another embodiment, the lifestyle assessment questions include questions about satisfaction with career, finance, home environment, personal growth, health, family, friends, love (e.g., relationship with significant other), social life, spirituality, emotional health, nutrition, purpose, fun, adventure, creativity, self-esteem, achievements, and/or creativity.

In one embodiment, the system includes questions regarding fatigue. In one embodiment, the questions regarding fatigue are from Krupp, et al. (1989). The Fatigue Severity Scale. Application to patients with multiple sclerosis and systemic lupus erythematosus. Archives of neurology. 46. 1121-3.

In one embodiment, the system includes recommendations regarding blue light usage, night-time caffeine usage, and/or napping. Studies such as "Natural Sleep and Its Seasonal Variations in Three Pre-industrial Societies" by Yetish et al., *Current Biology* V. 25, I. 21 (November 2015), which is incorporated herein by reference in its entirety, show that factors such as blue light, caffeine, and decrease napping have impacted human circadian rhythms relative to those in pre-industrial societies.

In another embodiment, the system determines a nap onset, a nap end, and a nap duration. The nap onset and the nap end are determined by the body sensors and/or from subjective information (e.g., questionnaires). In one embodiment, the system calculates a total duration of sleep in a 24-hour period (i.e., including the nap duration).

In yet another embodiment, the system includes information regarding a difficulty level for an intervention. In one embodiment, the information regarding a difficulty level for the intervention is determined by the user. In another embodiment, the information regarding the difficulty level for the intervention is determined by a coach and/or an influencer. In yet another embodiment, the information regarding the difficulty level for the intervention is determined by a machine learning algorithm. In one embodiment, the machine learning algorithm uses an adoption level of the intervention over all users, an adoption level of the intervention over similar users, a user's tolerance for and/or openness to adopt interventions, a financial cost of the intervention, a time required for the intervention, a user profile, a user medical history (e.g., injury), and/or a user history to determine the difficulty level for the intervention.

In one embodiment, the mobile application includes at least one challenge program. The at least one challenge program incorporates at least one small change into a user's life. The at least one challenge program is preferably for a predetermined period of time (e.g., 21 days, 4 weeks, 30 days, 1 month, 2 months, 3 months, etc.). In one embodiment, the at least one challenge program is related to sleep (e.g., bedtime, wake time, amount of sleep), nutrition (e.g., keto, WHOLE30, eat more vegetables, no candy, no soda, drink 8 glasses of water daily, no alcohol, bring lunch to work), fitness (e.g., daily exercise, push-ups, planks), mental health (e.g., gratitude journal, meditation, connecting with friends and family), and/or habits (e.g., quit smoking, spend time on a hobby, write a novel, reading, decluttering, no television, budget).

In one embodiment, the at least one challenge program is divided into multiple phases, wherein certain challenges and/or habits only appear in specific phases, before a specific phase, or after a specific phase. In one embodiment, each phase of the at least one challenge program includes a minimum and/or maximum number of challenges and/or habits. For example, in one embodiment, each phase has a maximum of 10 associated challenges and/or habits. In one embodiment, the challenges and/or habits selected for each user in each phase are prioritized based on an internal platform ranking and/or based on data associated with each user (e.g., sleep data, data from one or more smart appliances, etc.). In one embodiment, certain challenges and/or habits require that a user possess specific hardware (e.g., a smart light bulb, a weighted blanket, etc.) and those challenges are only provided if the platform receives an input that the user possesses such hardware. In one embodiment, challenges and/or habits are automatically provided by the platform to the user based on a chronotype (e.g., early bird, middle of the pack, night owl, etc.) of the user. In one embodiment, certain challenges and/or habits are only presented to a user during certain time periods (e.g., morning, day, evening, night, etc.) or only on specific times during the week (e.g., only weekends, only week days, etc.). For example, a challenge to take a mid-day nap every week only appears to users having a "night owl" chronotype. In one embodiment, the platform is operable to provide immediate habits and/or sleep recommendations for assisting in falling asleep.

In one embodiment, each challenge and/or habit provided by the platform includes an associated description of the challenge and/or habit. In one embodiment, each challenge and/or habit includes additional reading resources for learning more about the challenge and/or habit and its effect on sleep. Examples of challenges and/or habits include, but are not limited to, doing a good deed, taking a warm bath before bed, taking a mid-day nap, having a game night, making one's bed, stop hitting the snooze button, acupressure, acupuncture, make early dinner reservations, make a cryotherapy appointment, organize something, taking an ice bath, reading a physical book, turning off screens before bed, using diffuse lavender oil, drinking a glass of water in the morning, and using a weighted blanket, among others. In one embodiment, challenges and/or habits include taking one or more supplements, including, but not limited to, magnesium, glycine, *Ginkgo biloba*, B-vitamins, or other supplements. In one embodiment, challenges and/or habits include drinking one or more different types of tea, including, but not limited to, sleepytime tea, chamomile, passion flower, lemon balm, and other types of tea.

In one embodiment, the mobile application suggests additional interventions and/or lifestyle changes when a user is successful with current interventions and/or lifestyle changes. For example, if a user is getting enough sleep, the mobile application suggests that the user start walking or drink more water. In another embodiment, the mobile application suggests alternative interventions and/or lifestyle changes when a user is not successful with current interventions and/or lifestyle changes. For example, if a user is not successful with ice baths, the mobile application suggests cold showers. If the user is not successful with the cold showers, the mobile application suggests turning the temperature on the HVAC at night and/or adding a temperature-regulating mattress pad (e.g., CHILIPAD and/or OOLER).

Figure 67:
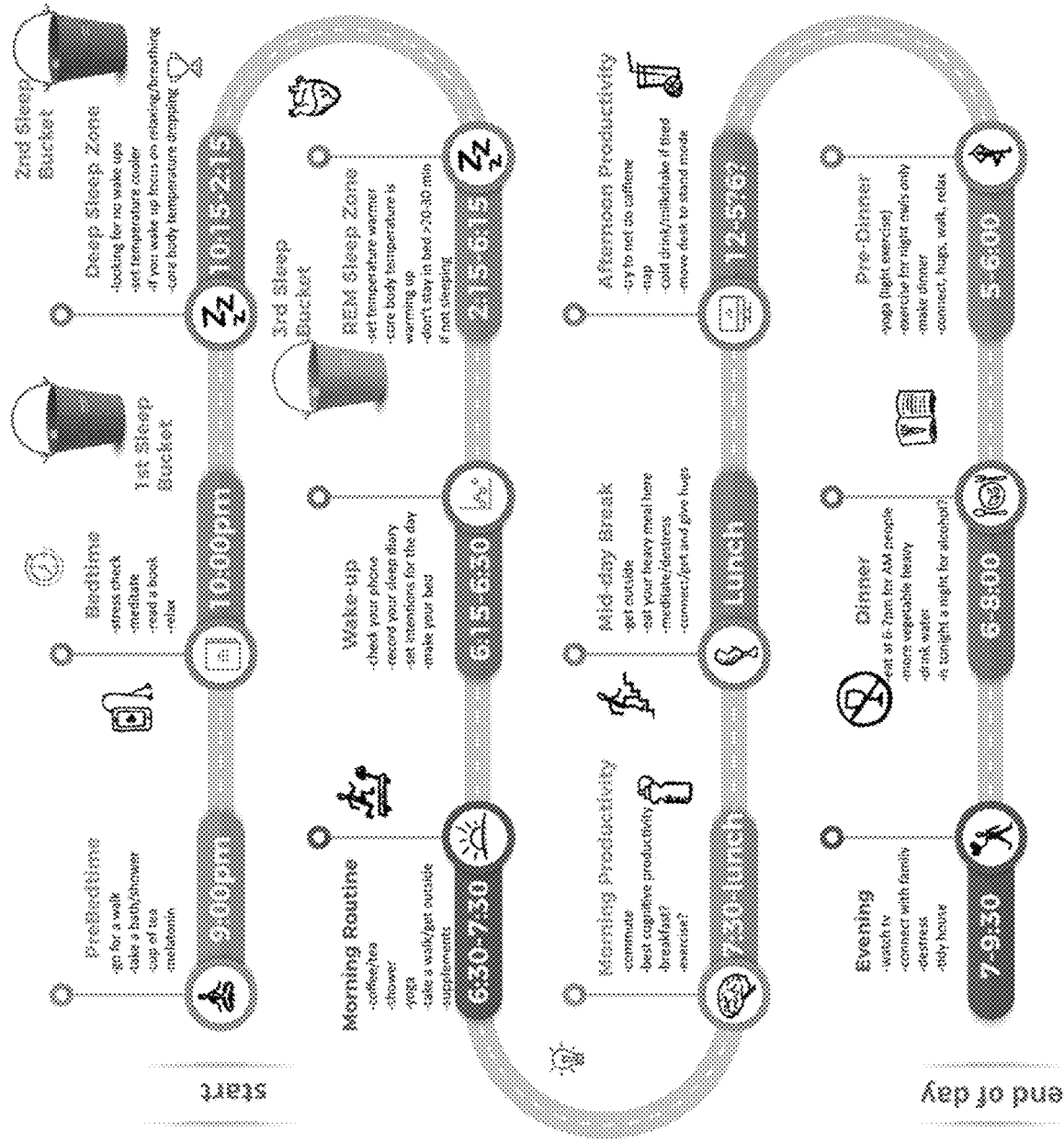
FIG. 67 illustrates an example of a breakdown of a 24-hour period.

FIG. 67 illustrates one example of a breakdown of a 24-hour period. Before bedtime (e.g., 9:00 pm), the mobile application suggests that a user take a walk, take a bath or shower, drink a cup of tea, or take melatonin. At bedtime (e.g., 10:00 pm), the mobile application does a stress check, and encourages a user to meditate, read a book, and/or relax. During the deep sleep zone (e.g., 10:15 pm-2:15 am), the mobile application determines whether there are any wake ups, sets temperature cooler (e.g., room temperature and/or surface temperature of a mattress/mattress pad/blanket), and monitors body temperature to determine that the body temperature is dropping. If the mobile application detects that the user wakes, the mobile application suggests relaxing and/or breathing exercises. During the REM sleep zone (e.g., 2:15-6:16 am), the mobile application sets the temperature warmer (e.g., room temperature and/or mattress/mattress pad temperature) and monitors the body temperature to determine that the body temperature is warming. If the mobile application detects that the user wakes, the mobile application suggests that the user not remain in bed more than 20-30 minutes after waking if the user cannot fall back asleep. At wake-up (e.g., 6:15-6:30 am), the mobile application prompts the user to record a sleep diary and set intentions for the day. In a preferred embodiment, the mobile application records and stores the sleep diary (e.g., in the historical subjective database and/or the global historical subjective database) and the intentions (e.g., in local storage). In one embodiment, the system records and stores the sleep diary, the intentions, and/or a journal (e.g., gratitude journal) on the cloud.

The mobile application is preferably operable to record caffeine consumption (e.g., coffee, tea, energy drinks), exercise information (e.g., type of exercise, duration, intensity, calories burned), and/or supplements (e.g., vitamins, minerals, herbs) taken, for example, during the morning routine. The morning productivity period is a time of best cognitive productivity. In a preferred embodiment, the mobile application records nutrition information (e.g., breakfast), including, but not limited to, number of calories, grams of fat, grams of carbohydrates, grams of protein, vitamins, minerals, and/or ingredients. During the mid-day break (e.g., lunch), the mobile application suggests that the user go outside, eat the heaviest meal of the day, meditate and/or destress, and/or connect with other individuals (e.g., communication, physical touch). The mobile application provides a prompt to not drink caffeine after a time point (e.g., noon). During a pre-dinner time, the mobile application suggests light exercise (e.g., yoga) for non-night owls, and suggests relaxing and connecting with other individuals.

Figure 68:
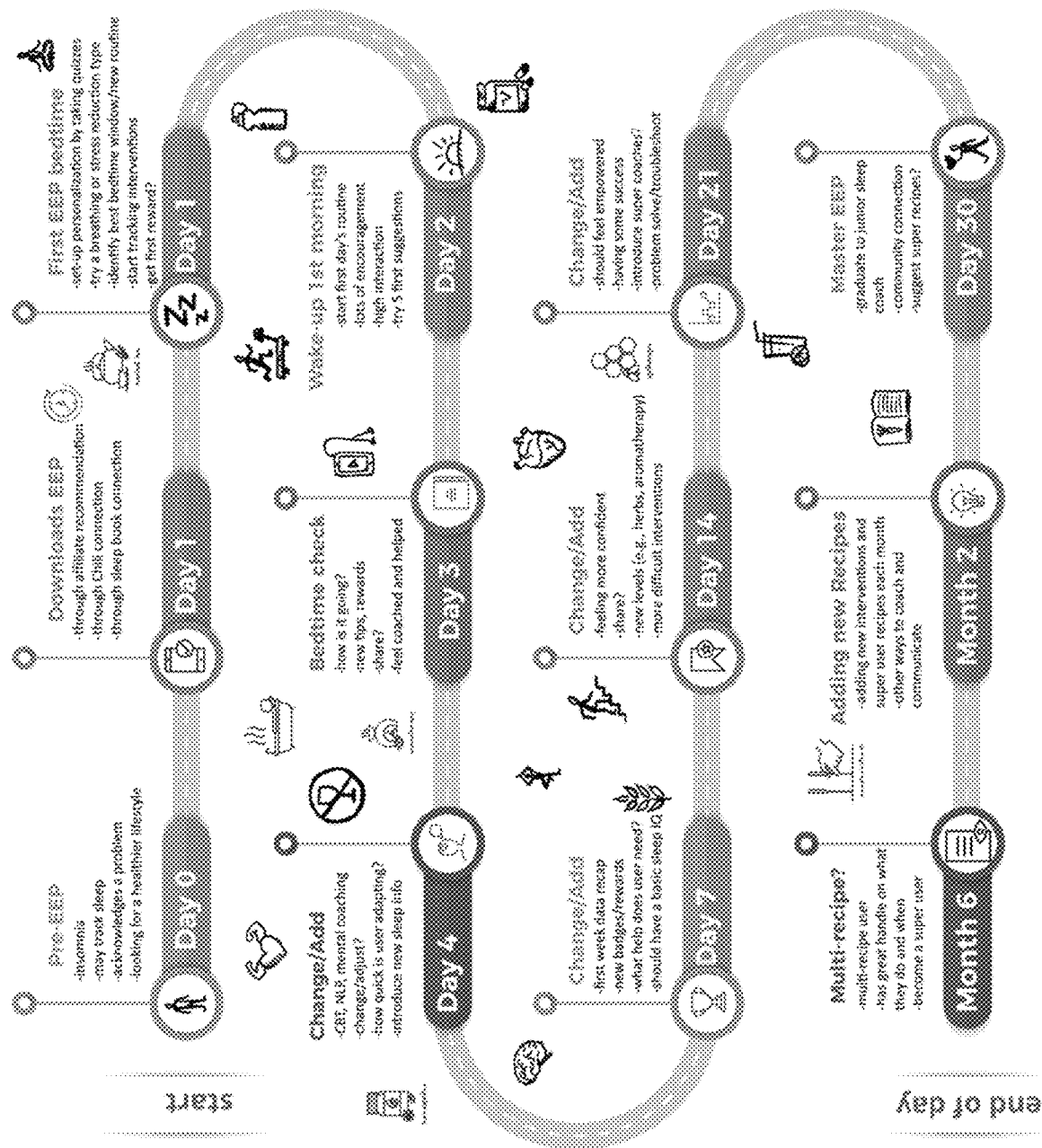
FIG. 68 illustrates one example of a breakdown of a 6-month period.

FIG. 68 illustrates one example of a breakdown of a 6-month period. For example, before using the mobile application, the user has insomnia and/or want to be healthier. On the first day of use, the mobile application provides quizzes to personalize suggestions for the user, including determining a chronotype. The mobile application begins tracking interventions on the first day of use. One the second day, the mobile application requests feedback from the user, provides a routine (e.g., based on chronotype), and interacts with the user. The mobile application is preferably operable to provide at least one reward (e.g., badge, status level, icon) to a user. The mobile application evaluates interventions to determine if the interventions are successful or not successful. If one or more interventions are not successful, the mobile application is operable to suggest at least one alternative intervention. In a preferred embodiment, the mobile application initially suggests interventions that are easy (e.g., go to bed at a specific time). The mobile application then suggests more difficult interventions as time passes. Alternatively, the mobile application initially suggests interventions projected to have the greatest impact, followed by interventions projected to have less impact. For example, the mobile application suggests a change in bedtime and wake time based on the chronotype.

In one embodiment, the mobile application is operable to prioritize user goals. For example, a user wants to exercise more and sleep better. The mobile application prioritizes solving the user's sleep problems in the first week, which will allow the user to have more energy to exercise in the second week.

FIG. 69 shows a table with an example of connections for users. In the example shown in FIG. 69, users are connected to a chronotype, a diet, at least one fitness type, at least one intervention, at least one influencer, and/or at least one coach. In one embodiment, the chronotype includes, but is not limited to, morning person, less morning person, neither morning person or night owl, less night owl, and/or night owl. Alternatively, the chronotype includes dolphin, bear, lion, and/or wolf. Diet includes any way of eating, including, but not limited to, ketogenic (keto) diet, paleo diet, fasting (e.g., intermittent fasting), WHOLE30, caloric restriction, vegan diet, vegetarian diet, Mediterranean diet, and gluten-free diet. Fitness includes any form of exercise (e.g., aerobic, strength, flexibility, balance), including, but not limited to, yoga, swimming, weights, running, cycling, kickboxing, CROSSFIT, ORANGE THEORY, barre, Pilates, walking, high intensity interval training (HIIT), and bodyweight exercises (e.g., push-ups, burpees, planks, squats, lunges). Interventions include any intervention that reduces stress or promotes sleep, including, but not limited to, meditation, journaling, breathing exercises, tiny habits, and medication or supplements (e.g., antihistamines, benzodiazepines, anti-depressants, melatonin, chamomile, ashwagandha, valerian root, omega-3 fatty acids, B-vitamins, L-theanine). Influencers are individuals with the ability to influence other users to adopt fitness, diet, and/or intervention regimens. Coaches are individuals with the ability to suggest users adopt particular fitness, diet, and/or intervention regimens based on personalized goals and/or needs.

In another embodiment, the connections also include, but are not limited to, health condition (e.g., injury), predisposition to health condition (e.g., family history of diabetes, history of gestational diabetes), age, relationship status (e.g., married, living with a partner, divorced, widowed, single), location, parental status, gender, medication, supplement, and/or a degree of willingness to accept alternative medicine.

Figure 70:
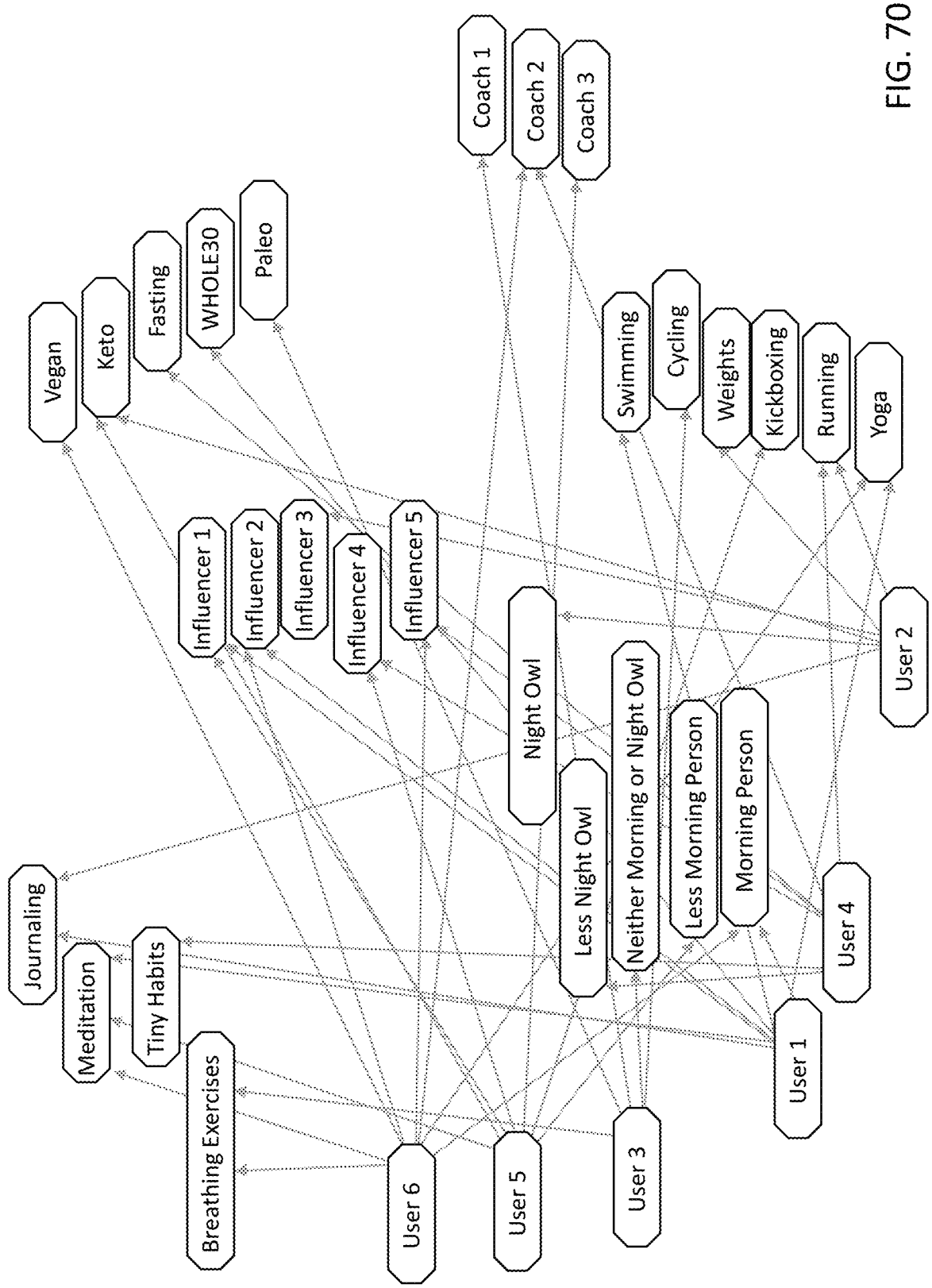
FIG. 70 shows a map of the connections from the table in FIG. 69.

FIG. 70 shows a map of the connections from the table in FIG. 69.

In one embodiment, the system allows a user to follow at least one influencer, at least one coach, and/or at least one other user. In another embodiment, the system provides a social networking component. The social networking component allows users to post updates and/or photos for other users to view, provide reactions (e.g., like, sad, etc.), and/or comment. In yet another embodiment, the social networking component is accessible via a third-party application.

In another embodiment, the mobile application updates the machine learning models based on recommendations from influencers. In one embodiment, the mobile application is operable to weigh recommendations based on ratings from the user. For example, if a user follows or is connected to two influencers and rates a first influencer as an $8/10$ and a second influencer as a $6/10$, the mobile application is operable to weigh recommendations from the first influencer higher than recommendations from the second influencer.

In one embodiment, the system uses global data (e.g., global historical subjective data, global historical objective data, global historical environmental data, global profile data) to initially train the machine learning algorithms. The machine learning algorithms preferably suggest at least one intervention to the user to reduce stress, increase health, and/or promote sleep. In another embodiment, the machine learning algorithms are further refined and/or personalized by sensor data (e.g., body sensors, environmental sensors), user data (e.g., user profile, historical subjective data, historical objective data, historical environmental data), and/or feedback (e.g., user feedback, healthcare professional feedback, expert feedback, etc.). In yet another embodiment, the mobile application uses if-then rules to provide interventions and/or suggestions. For example, if a heart rate sensor determines that a user's heart rate is high without accompanying movement detected on an accelerometer, the mobile application provides a suggestion to meditate or take a walk.

The system is preferably operable to detect pivots or changes in a user's lifestyle. For example, the system offers different interventions to a pregnant woman or a breastfeeding mother (e.g., supplements, less rigorous exercise) than to a fit woman. In one embodiment, the system detects whether a user has moved and/or is travelling. In another embodiment, the system uses GPS to determine whether the user has moved and/or is travelling.

The system is preferably operable to integrate with at least one calendar for the user. In one embodiment, the system provides notifications to a user and/or a checklist for a user. For example, the system provides a notification for the user to lay out supplements on Sunday.

In one embodiment, the camera on the at least one remote device is operable to scan a room and/or a sleeping environment. The system is operable to user the scan of the room and/or the sleeping environment to provide feedback to a user and/or suggest at least one intervention or at least one change to the room and/or the sleeping environment (e.g., darker blinds, declutter) to reduce stress and/or promote sleep. In one embodiment, the system uses augmented reality to display the at least one intervention or the at least one change to the room and/or the sleeping environment on the at least one remote device. Advantageously, this allows a user to see how the at least one intervention or the at least one change to the room and/or the sleeping environment affects the room and/or sleeping environment.

Figure 71:
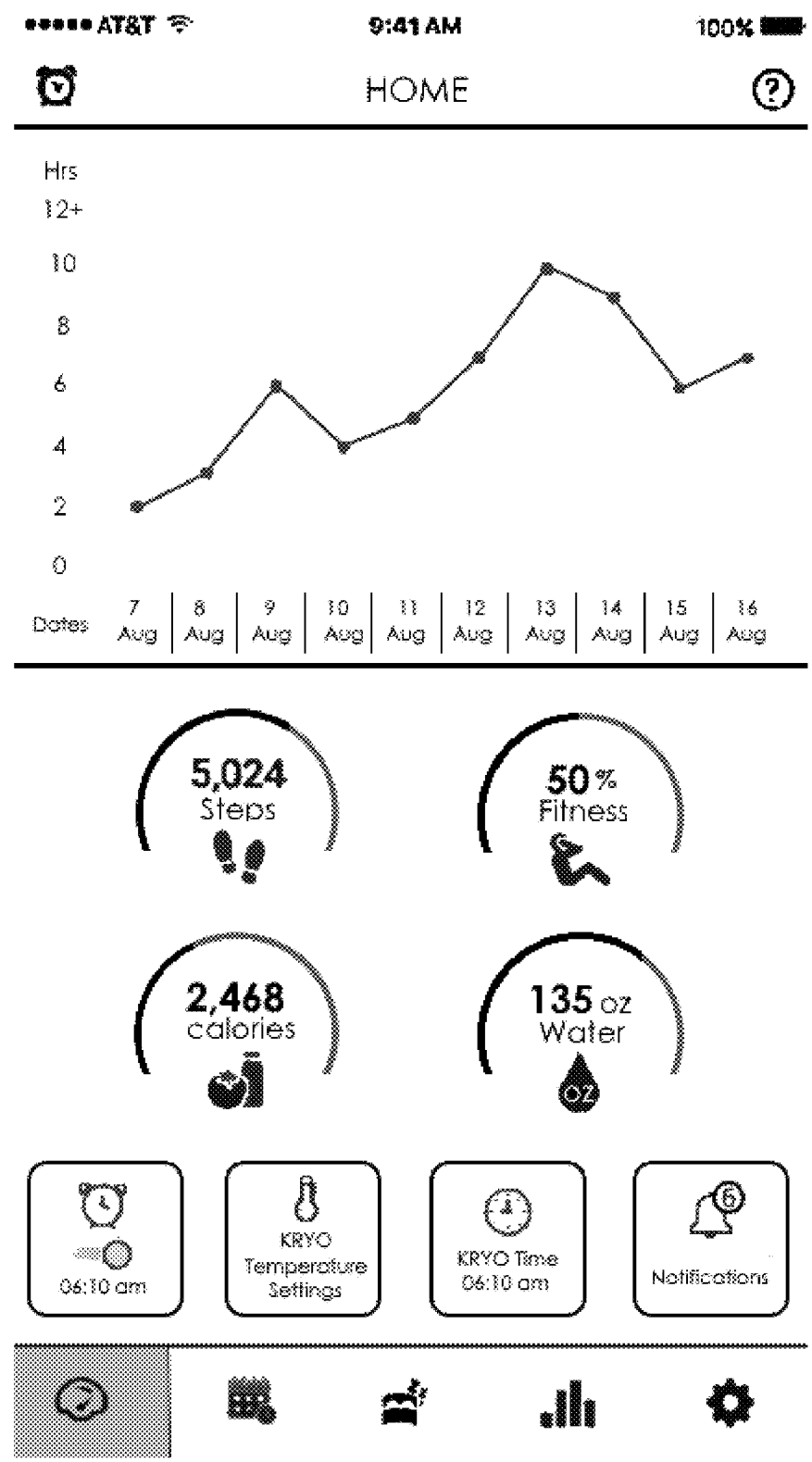
FIG. 71 illustrates a home screen of one embodiment of a graphical user interface (GUI) for a mobile application.

FIG. 71 illustrates a home screen of one embodiment of a graphical user interface (GUI) for a mobile application. A bottom navigation bar allows a user to rapidly switch between destinations within the mobile application. In FIG. 71, the bottom navigation bar includes (in order from left to right) icons for the home screen, a schedule screen, a sleep screen, a progress screen, and a goal settings screen.

The home screen includes a graph of the number of hours a user slept versus dates. In this example, the graph provides the number of hours a user slept for the previous 10 days. In one embodiment, the number of hours a user slept for a day is obtained from a wearable device (e.g., FITBIT, JAWBONE UP, MISFIT, APPLE WATCH, NOKIA STEEL, NOKIA GO). Alternatively, the user manually enters a time the user went to sleep and a time the user woke up.

The home screen also provides a current snapshot of the user's daily health information. The user's daily health information includes, but is not limited to, the number of steps the user has taken, the percentage of fitness goals achieved, the number of calories consumed by the user, and the amount of water consumed by the user. This information is preferably updated in real time or near-real time by the mobile application. In one embodiment, this information is manually entered into the mobile application. Alternatively, this information is obtained from third-party applications (e.g., FITBIT, JAWBONE, MISFIT, MYFITNESSPAL, APPLE HEALTH, NOKIA HEALTH MATE).

The home screen allows the user to set a smart alarm (e.g., 6:10 AM). The smart alarm increases the surface temperature of the mattress pad sufficiently over a period of time to allow the user to emerge out of the last sleep cycle. The speed of awakening is based on the sleep cycle information. The speed of temperature increase is faster (e.g., 0.278° C./minute (0.5° F./minute)) if a new cycle is just beginning. The speed of temperature increase is slower (e.g., 0.056° C./minute (0.1° F./minute)) if the user is just coming out of the bottom of a sleep cycle. In one embodiment, the mobile application uses active data collection of the user's vital signs, including, but not limited to, heart rate, breath rate, blood oxygen level, brain waves, and/or skin temperature, to determine the speed of awakening.

Figure 72:
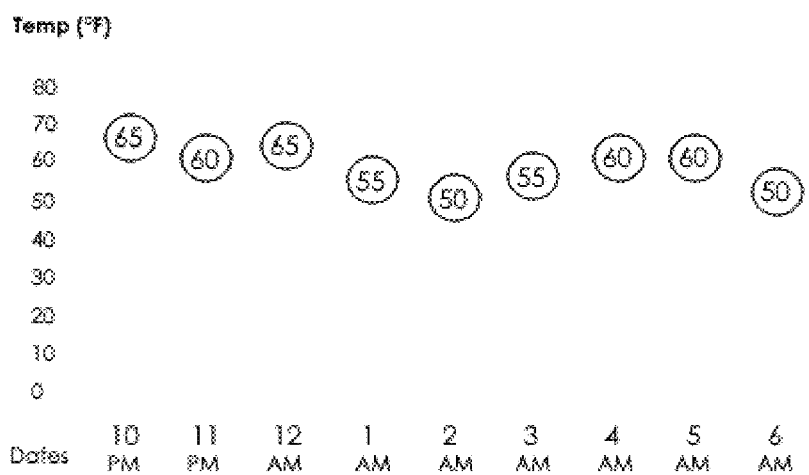
FIG. 72 illustrates a schedule screen of one embodiment of a GUI for a mobile application.

FIG. 72 illustrates a schedule screen of one embodiment of a GUI for a mobile application. The mobile application allows a user to select a temperature schedule. In FIG. 72, the temperature varies between 10-18.33° C. (50-65° F.) between 10 PM and 6 AM. The schedule screen displays a graph of temperature versus time.

Figure 73:
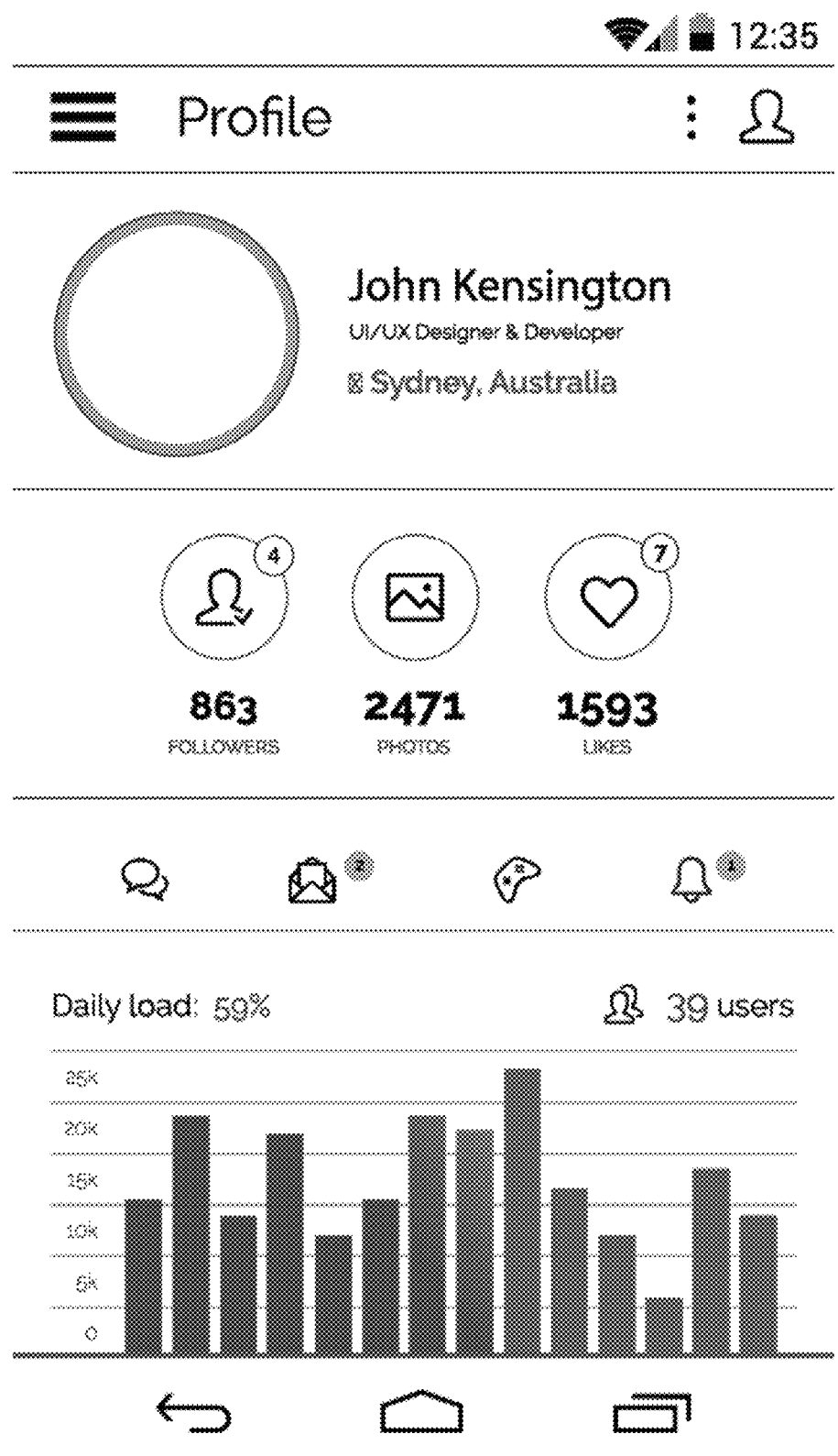
FIG. 73 illustrates another schedule screen of one embodiment of a GUI for a mobile application.

FIG. 73 illustrates another schedule screen of one embodiment of a GUI for a mobile application. The mobile application allows a user to select a sleep time and a wake time.

Figure 74:
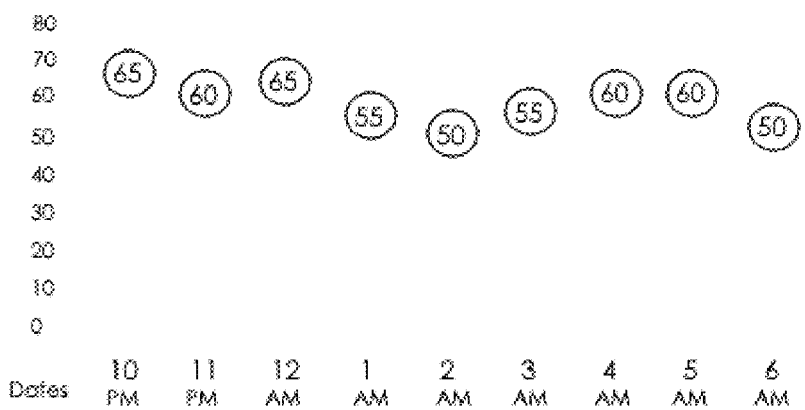
FIG. 74 illustrates a sleep screen of one embodiment of a GUI for a mobile application.

FIG. 74 illustrates a sleep screen of one embodiment of a GUI for a mobile application. The sleep screen displays a graph of time versus temperature for the previous day. The sleep screen displays a starting temperature and a wake time for the sleeping period. The user can select a "start sleep" button to manually track sleep cycles.

The sleep screen also has a button for a smart alarm. This allows the mobile application to adjust the settings of the mattress pad to wake the user at an optimal time within a sleep cycle. As previously described, gently awakening the user by increasing the temperature prevents sleep inertia. The sleep screen also has a button for tracking motion of the user. Further, the sleep screen also has a button for tracking sound of the user.

Figure 75:
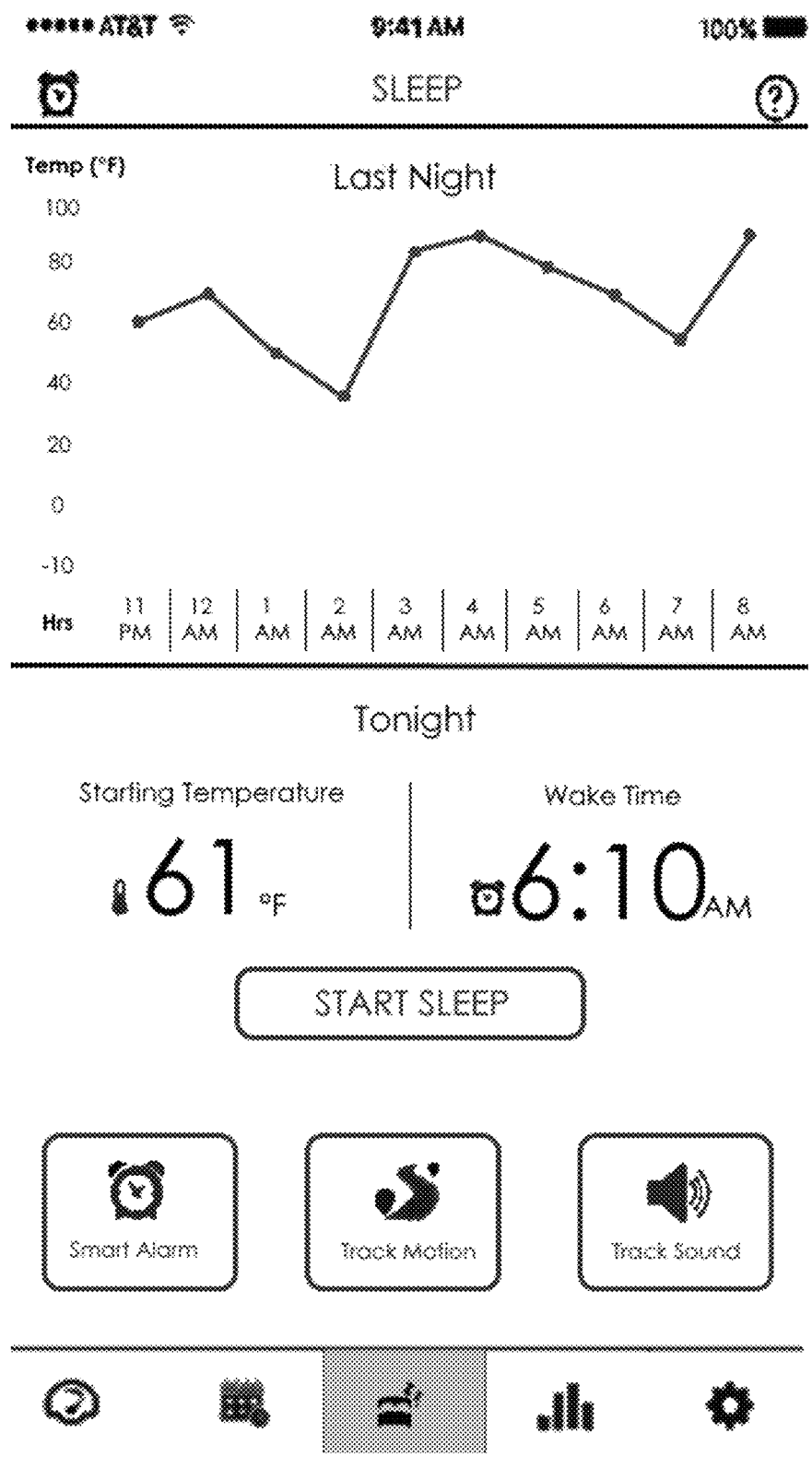
FIG. 75 illustrates a goal settings screen for one embodiment of a GUI for a mobile application.

FIG. 75 illustrates a goal settings screen for one embodiment of a GUI for a mobile application. The goal settings screen allows a user to turn a bed time reminder on or off and select a target number of hours of sleep (e.g., 8 hours). The goal settings screen also allows a user to select a preferred sleep time (e.g., 10:00 PM) and a preferred wake time (e.g., 6:00 AM). The goal settings screen also allows a user to set a goal weight, goal amount of water to consume, and goal number of calories to consume. Additional goals include, but are not limited to, a faster time to fall asleep, fewer awakenings during the sleeping period, more REM sleep, more deep sleep (e.g., N3 sleep), and/or a higher sleep efficiency.

Figure 76:
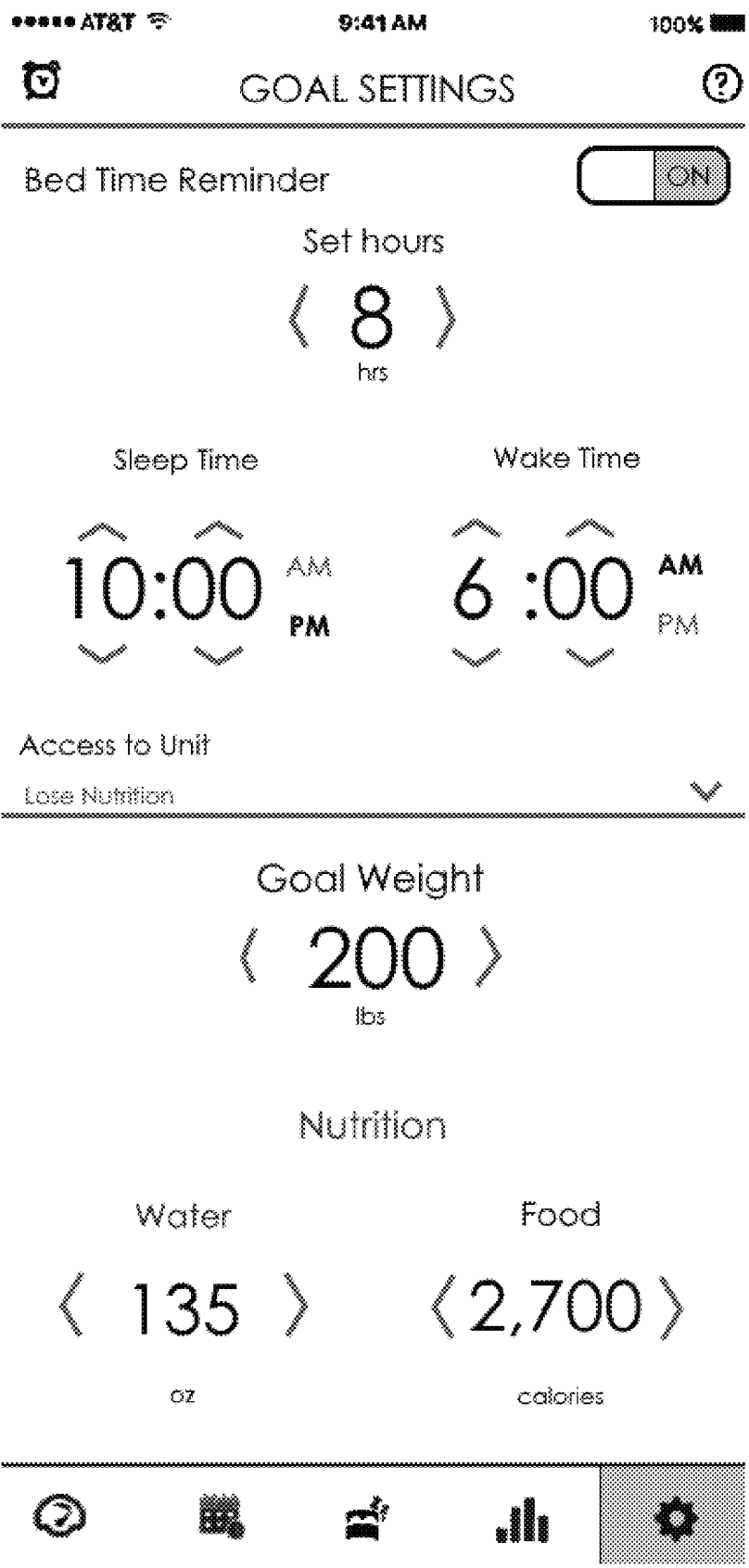
FIG. 76 illustrates a progress screen for one embodiment of a GUI for a mobile application.

FIG. 76 illustrates a progress screen for one embodiment of a GUI for a mobile application. The progress screen includes a graph of the number of hours a user slept versus dates. In this example, the graph provides the number of hours a user slept for the previous 10 days. The progress screen displays a current sleep efficiency (e.g., 80%). The progress screen lists the current date, a sleep time, a wake time, and number of hours of sleep. A "log manually" button allows the user to manually log sleep. The progress screen also includes a graph of the depth of sleep (e.g., light or deep) versus dates. In this example, the graph provides the depth of sleep for the previous 10 days. The progress screen displays a time spent in deep sleep (e.g., 5.30 hrs) and a time spent in light sleep (e.g., 3.15 hrs).

Figure 77:
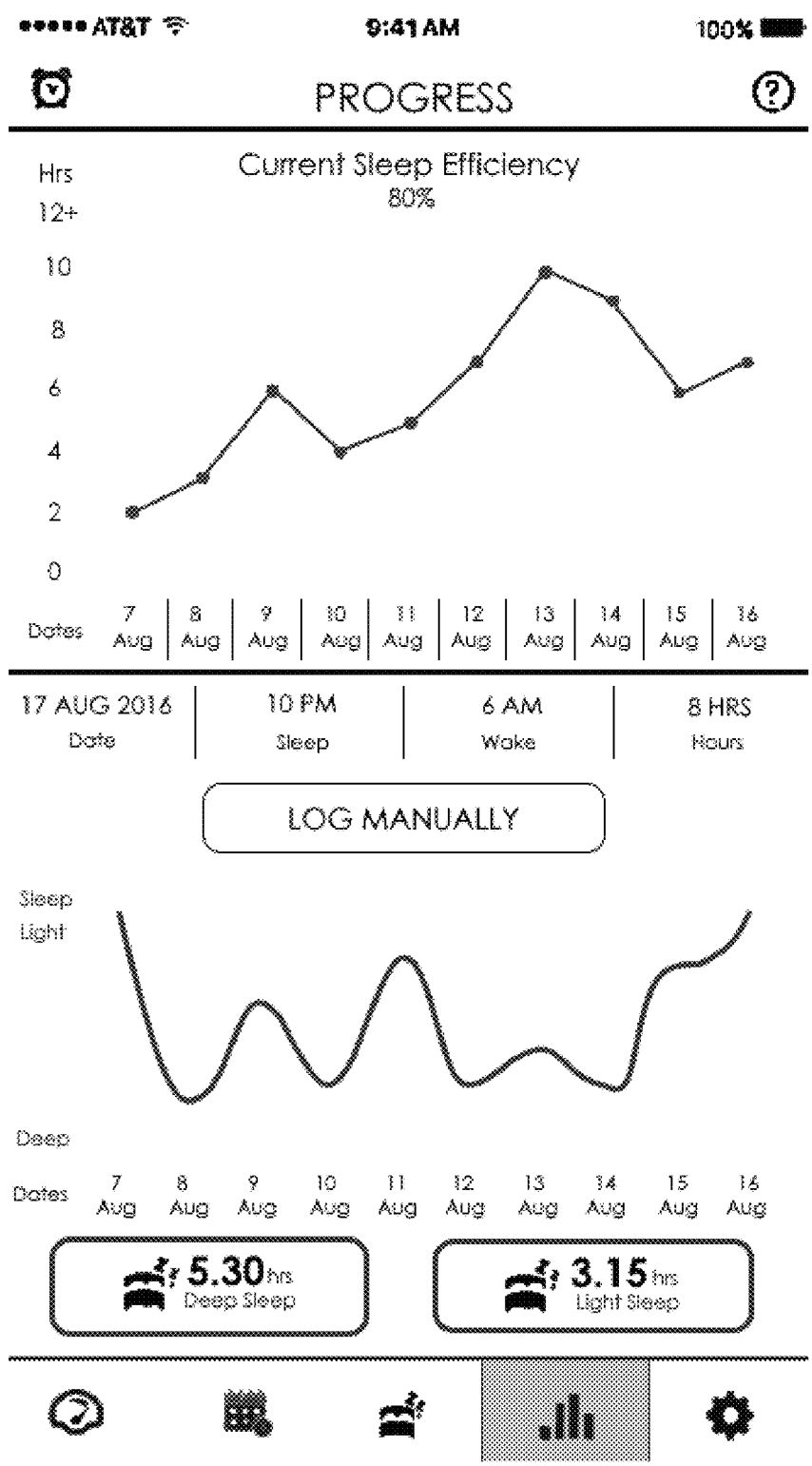
FIG. 77 illustrates a profile screen for one embodiment of a GUI for a mobile application.

FIG. 77 illustrates a profile screen for one embodiment of a GUI for a mobile application. In this embodiment, the mobile application includes a social component. The mobile application allows users to upload photos. The mobile application also allows users to follow other users. In this example, the user has 863 followers. A notification illustrates that the user has 4 new followers. Additionally, the mobile application allows users to like status updates and photos of other users. In this example, the user has posted 2471 photos and has 1593 likes. A notification illustrates that the user has 7 new likes. Further, the GUI displays statistics for the number of likes, followers, and photos over several months.

Figure 78:
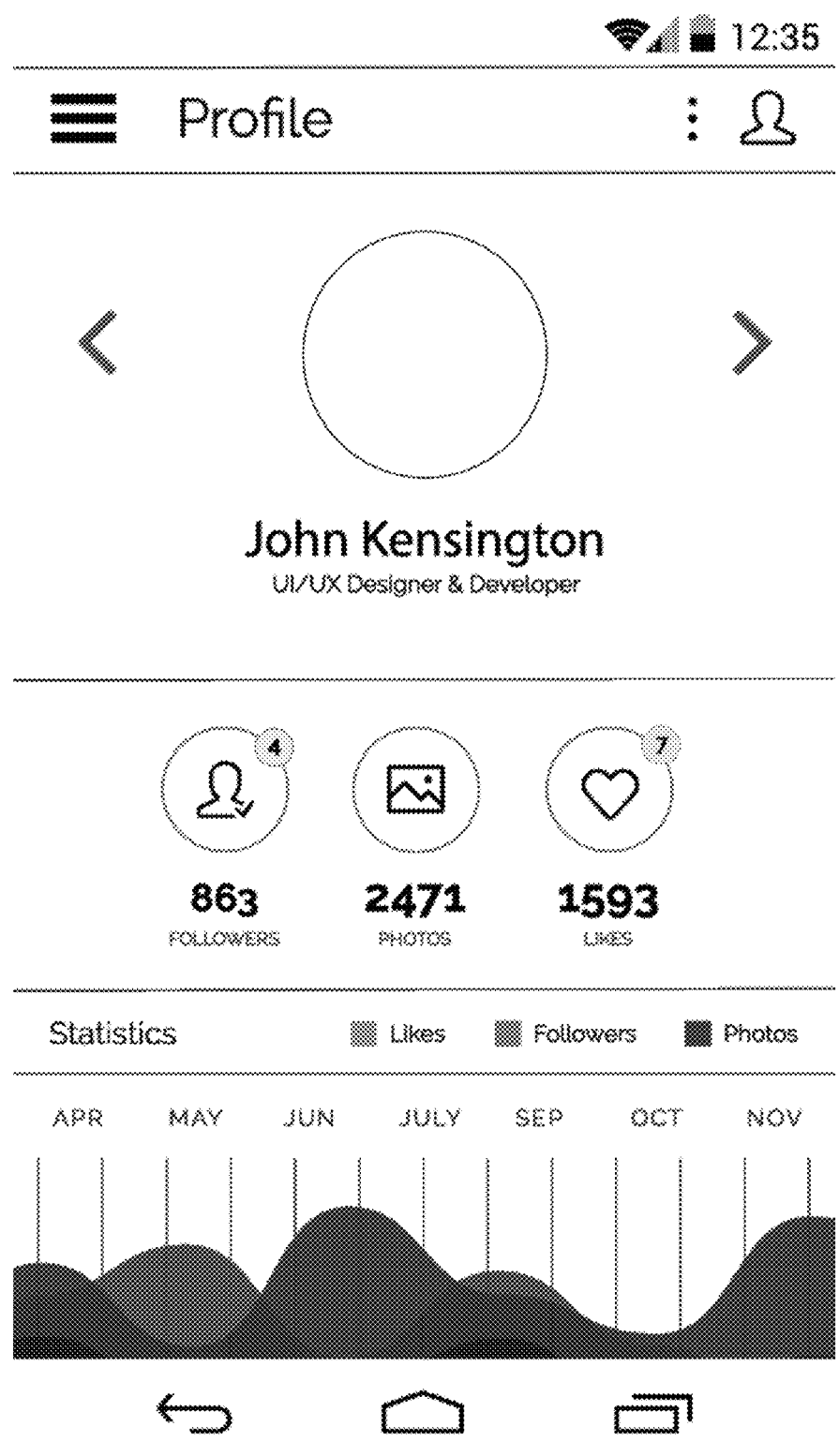
FIG. 78 illustrates another profile screen for one embodiment of a GUI for a mobile application.

FIG. 78 illustrates another profile screen for one embodiment of a GUI for a mobile application. In this example, the mobile application is operable to send messages between users.

FIG. 79 illustrates yet another profile screen for one embodiment of a GUI for a mobile application. In this example, the profile screen displays a weekday sleep time of 10 PM and a weekday wake up time of 6 AM. The profile screen also displays a weekend sleep time of 10 PM and a weekend wake up time of 6 AM. The profile screen includes a button to add sleep profile. A bottom navigation bar allows a user to rapidly switch between destinations within the mobile application. In FIG. 79, the bottom navigation bar includes (in order from left to right) icons for a temperature screen, a sleep screen, an alarm screen, a notification screen, and a settings screen.

Figure 80:
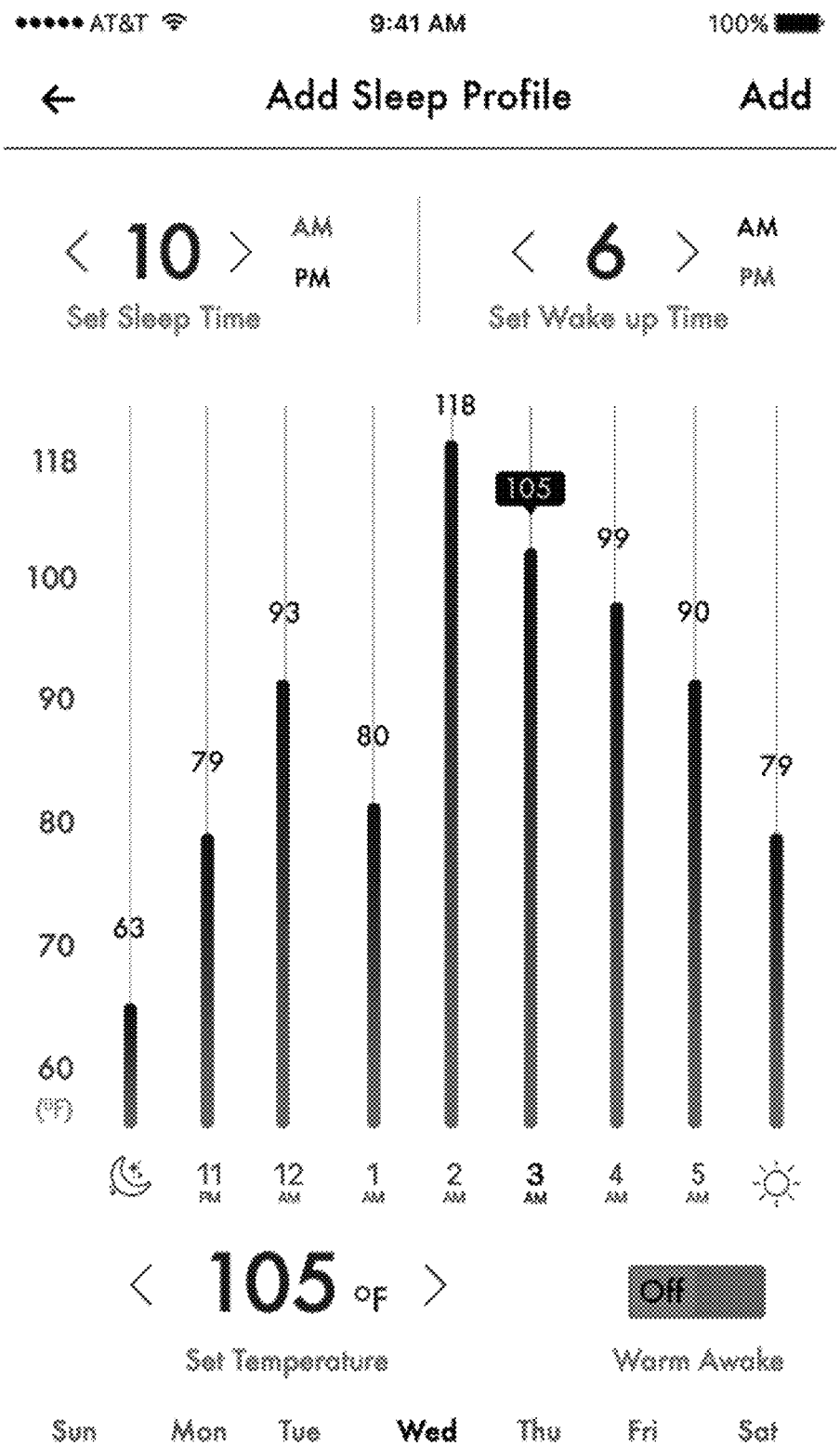
FIG. 80 illustrates an add sleep profile screen for one embodiment of a GUI for a mobile application.

FIG. 80 illustrates an add sleep profile screen for one embodiment of a GUI for a mobile application. The mobile application is operable to allow the user to set a sleep time and a wake-up time. Further, the mobile application is operable to allow a user to select temperatures for a mattress pad over a sleep period. In this example, the temperature is set at 17.22° C. (63° F.) at 10 PM, 26.11° C. (79° F.) at 11 PM, 33.89° C. (93° F.) at 12 AM, 26.67° C. (80° F.) at 1 AM, 47.78° C. (118° F.) at 2 AM, 40.56° C. (105° F.) at 3 AM, 37.22° C. (99° F.) at 4 AM, 32.22° C. (90° F.) at 5 AM, and 26.11° C. (79° F.) at 6 AM. Further, the mobile application allows the user to select warm awake, which slowly (e.g., 0.278° C./minute (0.5° F./minute)) warms the user to awaken the user.

Figure 81:
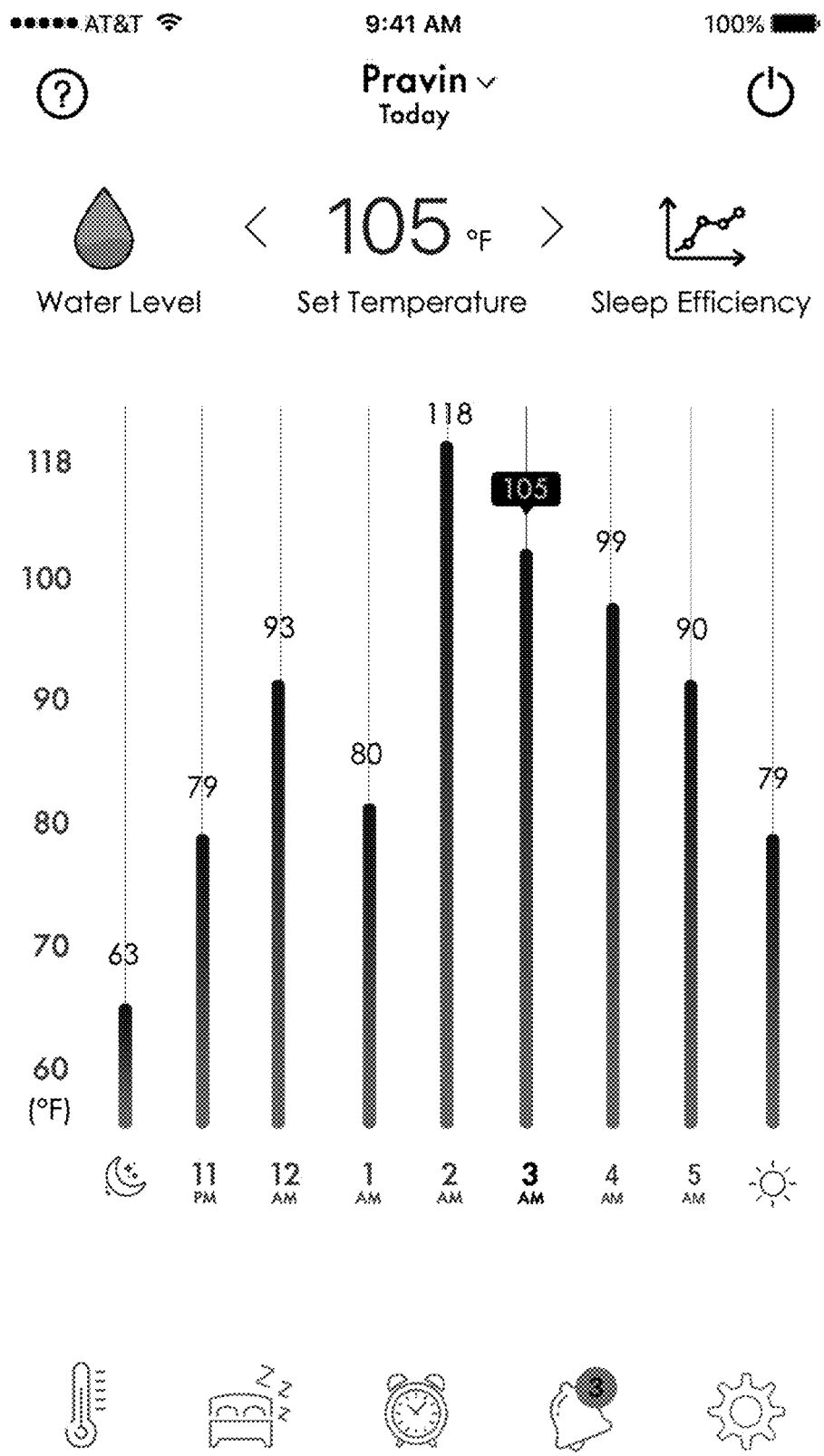
FIG. 81 illustrates a dashboard screen for one embodiment of a GUI for a mobile application.

FIG. 81 illustrates a dashboard screen for one embodiment of a GUI for a mobile application. In this embodiment, the mobile application is operable to allow the user to check the water level of the at least one reservoir in the control unit. In a preferred embodiment, the mobile application notifies the user when the water level is below a threshold. Further, the mobile application allows the user to display sleep efficiency.

In another embodiment, the mobile application notifies the user that water treatment or purification is required. In another embodiment, the mobile application automatically schedules water treatment or purification (e.g., automatically turning on the ultraviolet (UV) light for water treatment) at designated time intervals.

Most individuals adopt a monophasic sleep pattern (e.g., sleeping 6-8 hours at a time). Non-monophasic sleep occurs when an individual adopts a biphasic or polyphasic sleep pattern. A biphasic sleep pattern is when the individual sleeps twice per day. Typically, this consists of a shorter rest (e.g., "siesta") during the day and a longer sleep period during the night. A polyphasic sleep pattern (e.g., Everyman, Uberman, Dymaxion, Dual Core) consists of multiple sleeps throughout the day, generally ranging from 4 to 6 periods of sleep per day.

Figure 82:
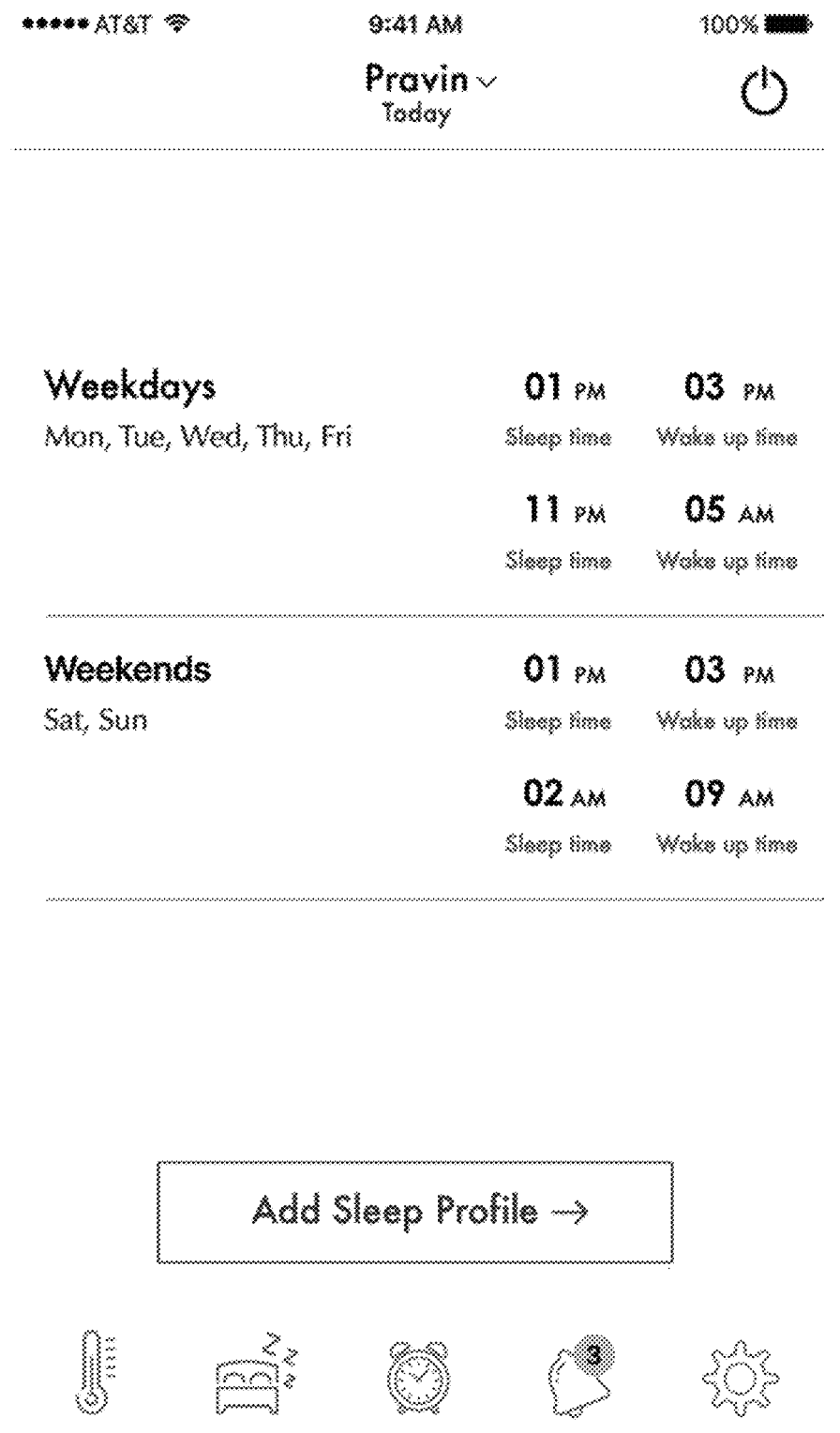

FIG. 82 illustrates a profile screen for one embodiment of a GUI for a mobile application allowing for biphasic sleep. In this example, the user sleeps from 1 PM to 3 PM and 11 PM to 5 AM on weekdays. The user also sleeps from 1 PM to 3 PM and 2 AM to 9 AM on weekends.

Although FIGS. 79 and 82 show weekday and weekend sleep schedules, the mobile application is operable to allow users to set specific sleep schedules for each day of the week. In one example, the mobile application allows the user to set different sleep schedules for Monday through Thursday (e.g., work days of a compressed work week), Friday, Saturday, and Sunday.

In a preferred embodiment, the mobile application is operable to provide reminders to the user. In one example, the mobile application reminds the user to get additional sleep (e.g., due to physical activity). In another example, the mobile application alerts the user to go to sleep. In one embodiment, the mobile application is operable to provide suggestions for treatments based on the user profile. In one example, the mobile application provides a guided meditation to relieve stress. In another example, the mobile application suggests a treatment with a TENS device to relieve pain.

In another embodiment, the mobile application is operable to analyze trends over time. In one example, the mobile application determines that the user's heart rate has increased by 15 beats per minute over a time period of a year. The mobile application suggests that the user contact a health care provider because this is possibly a symptom of heart disease. In another example, the mobile application determines that the user's blood oxygen level as measured by a pulse oximeter decreases at night. The mobile application suggests that the user contact a health care provider because this is possibly a symptom of sleep apnea.

The mobile application preferably allows the user to download their information (e.g., in a comma-separated value (CSV) file). Additionally, or alternatively, the mobile application allows the user to share their information with a health care provider and/or a caregiver.

Figure 83:
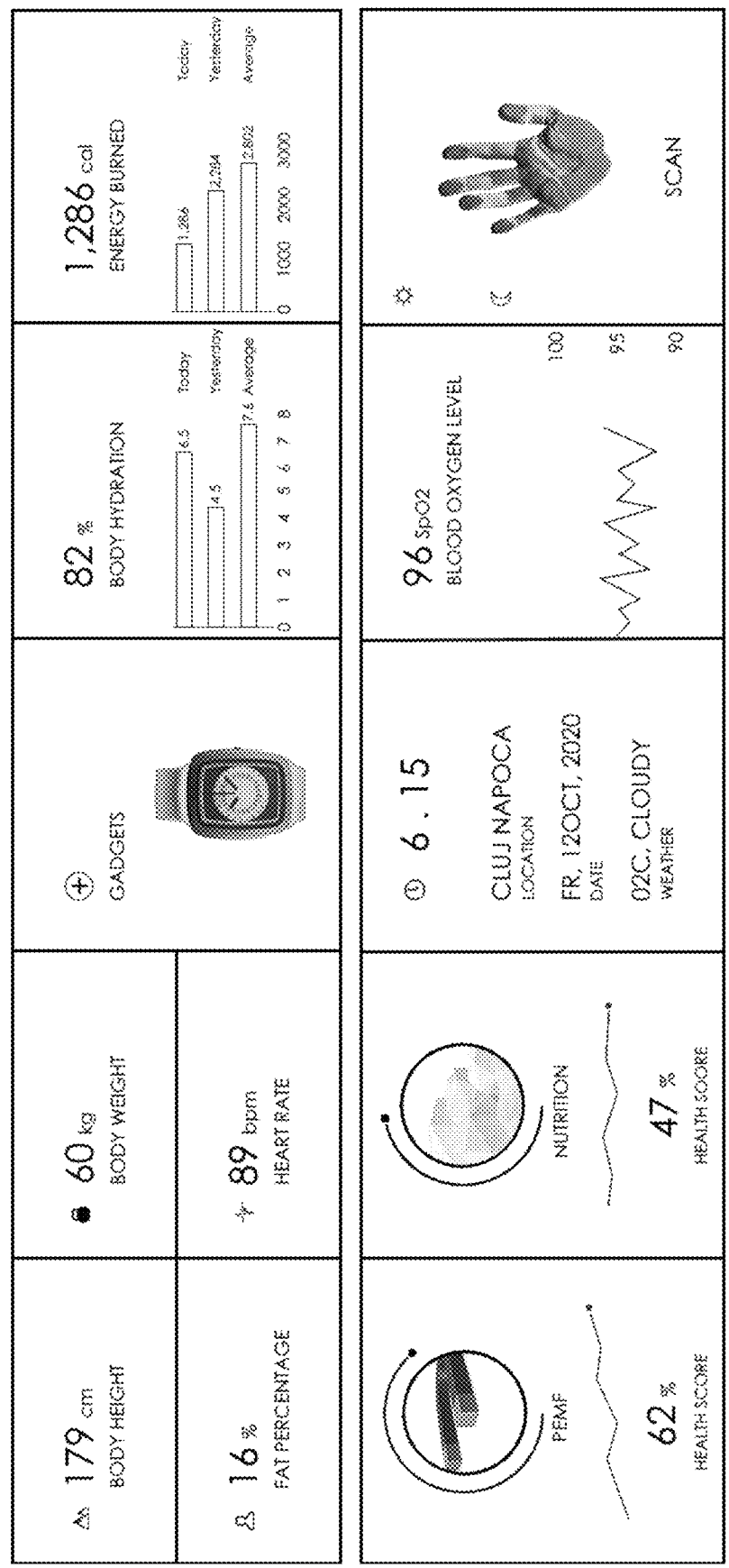
FIG. 83 illustrates a dashboard screen for another embodiment of a GUI for a mobile application.

FIG. 83 illustrates a dashboard screen for another embodiment of a GUI for a mobile application. In this embodiment, the dashboard screen displays a personal health score for a user. In a preferred embodiment, the personal health score is calculated using a sleep quality score and a sleep quantity score. In one embodiment, the personal health score is calculated by weighing the sleep quality score higher than the sleep quantity score. In one example, a ratio of 9:7 of sleep quality score to sleep quantity score is used to calculate the personal health score.

A body height and a body weight for the user are displayed on the dashboard screen. Although the body height and the body weight are displayed in metric units (cm and kg, respectively), the mobile application is operable to display alternative units (e.g., feet, pounds). In one embodiment, the body weight is obtained from a smart scale (e.g., FITBIT ARIA, NOKIA BODY+, GARMIN INDEX, UNDER ARMOUR SCALE, PIVOTAL LIVING SMART SCALE, IHEALTH CORE) and/or through a third-party application. Alternatively, the body height and/or the body weight are entered manually by the user. A fat percentage for the user is displayed on the dashboard screen. In one embodiment, the fat percentage is obtained from a smart scale using bioelectrical impedance and/or through a third-party application. In another embodiment, the fat percentage is entered manually by the user. Alternatively, the dashboard displays a body mass index for the user. The body mass index is calculated using the body weight and the body height of the user. A heart rate for the user is displayed on the dashboard screen. The heart rate is preferably obtained from the heart rate sensor.

The dashboard screen allows the user to link gadgets (e.g., FITBIT, JAWBONE UP, MISFIT, APPLE WATCH, NOKIA STEEL, NOKIA GO, smart scales) to the mobile application. A body hydration level is displayed for the user on the dashboard screen. In one embodiment, the body hydration level is expressed as a percentage. In one embodiment, the body hydration level is calculated based on a number of glasses of water a day. In one example, a user has consumed 4 glasses of water in a day with a target of 8 glasses of water in a day, resulting in a body hydration level of 50%. Alternatively, the body hydration level is calculated based on a number of ounces of water. In one example, a user has consumed 1.5 L of water in a day with a target of 3 L of water in a day, resulting in a body hydration level of 50%. In a preferred embodiment, the screen displays a body hydration level for today, yesterday, and/or an overall average.

An energy burned for the user is displayed on the dashboard screen. The energy burned is preferably displayed as the number of calories burned. In a preferred embodiment, the energy burned is obtained from a wearable device (e.g., FITBIT, JAWBONE UP, MISFIT, APPLE WATCH, NOKIA STEEL, NOKIA GO). In another embodiment, the energy burned is obtained from a smartphone or a third-party application. Alternatively, the energy burned is manually entered by the user. In a preferred embodiment, the screen displays an energy burned level for today, yesterday, and/or an overall average.

The dashboard screen also displays a PEMF health score. The PEMF health score is preferably displayed as a percentage. In a preferred embodiment, the PEMF health score is based on user input. In one example, the PEMF health score is based on answers to survey questions. The survey questions ask the user to rate pain one hour after treatment, during physical activity, 24 hours after treatment, two days after treatment, five days after treatment, and/or one week after treatment. The survey questions ask the user to rate flexibility and/or mobility one hour after treatment, during physical activity, 24 hours after treatment, two days after treatment, five days after treatment, and/or one week after treatment. The answers to the survey questions determine the level of treatment needed and the PEMF health score. In one example, an acute issue is given a PEMF health score between about 0% and about 35%, an ongoing issue is given a PEMF health score between about 35% and about 65%, and a managed issue requiring booster treatments (e.g., a monthly booster treatment) is given a PEMF health score between about 65% and about 95%.

A nutrition health score is displayed for the user on the dashboard screen. The nutrition health score is preferably displayed as a percentage. In a preferred embodiment, the nutrition health score is based on user input. In one embodiment, the nutrition health score is based on a target number of calories. In one example, a user has consumed 1000 calories in a day with a target of 2000 calories in a day, resulting in a nutrition health score of 50%. In another embodiment, the nutrition health score is based on a target percentage of fat, a target percentage of carbohydrates, and/or a target percentage of protein. Alternatively, the nutrition health score is based on a target total amount of fat, a target total amount of carbohydrates, and/or a target total amount of protein. In one example, a user has consumed 50 grams of protein with a target of 100 grams of protein in a day, resulting in a nutrition health score of 50%. In yet another embodiment, the nutrition health score includes nutritional supplements (e.g., vitamins, minerals, herbals, botanicals, amino acids, enzymes, probiotics, prebiotics) consumed by the user.

The dashboard screen also displays a time of day (e.g., 6:15), a location, a date, and/or a weather forecast for the location. In one embodiment, the weather forecast for the location includes a temperature and/or a condition (e.g., cloudy, sunny).

A blood oxygen level for the user is displayed on the dashboard screen. The blood oxygen level for the user is obtained from the pulse oximeter sensor. The dashboard screen includes a button to prompt a scan with an energy field sensor. In a preferred embodiment, the energy field sensor is a GDV device. In one embodiment, the GDV device scans at least one hand and/or at least one finger of a user to measure an energy field of the user.

FIG. 84 illustrates a treatment summary screen for one embodiment of a GUI for a mobile application. The treatment summary screen displays a number of minutes for treatments within a month for a user. In this embodiment, the treatment summary screen displays the number of minutes the user was treated using infrared, TENS, and PEMF during the month. In a preferred embodiment, the number of minutes the user was treated within the month is displayed as a bar graph, with each of the treatments (e.g., infrared, TENS, PEMF) displayed in different colors. A date of the month (e.g., 1, 3, 6, 9, 12, 15, 18, 21, 24, 27) is preferably displayed under the number of minutes the user was treated.

Figure 85:
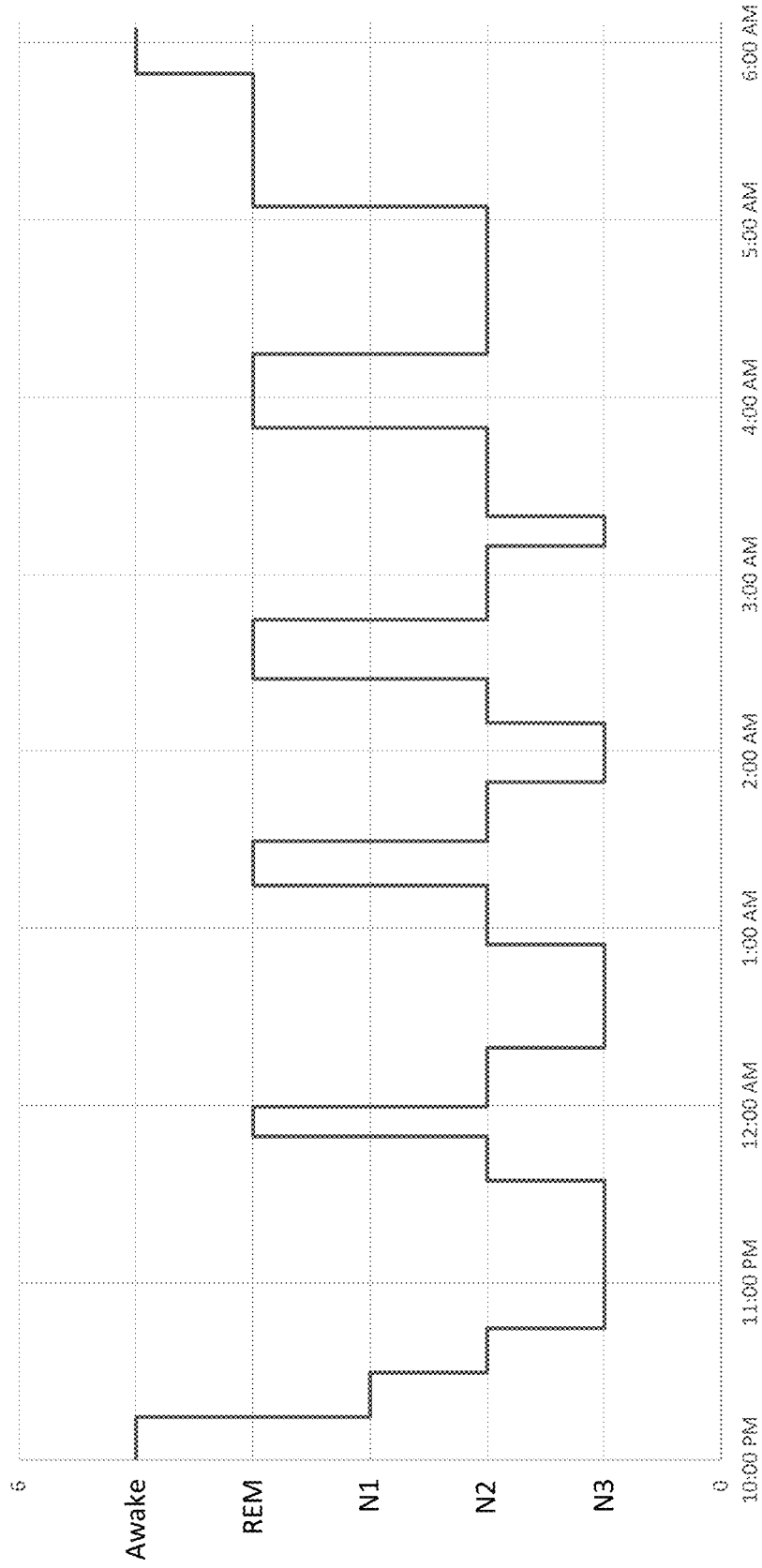
FIG. 85 illustrates a hypnogram for a sleep cycle for a normal sleeper.

FIG. 85 illustrates a hypnogram for a sleep cycle for a normal sleeper. A normal sleeper enters deep sleep 3-5 times in a sleeping period. A hypnogram provides information on sleep stages for an individual (e.g., amount of time spent in N1, N2, N3, REM, light sleep, etc., amount of time between falling asleep and entering a given sleep stage, etc.). In one embodiment, a user device includes a GUI with a live-updating hypnogram that provides the user with information about their sleep. In another embodiment, the hypnogram on the GUI is updated at regular intervals (e.g., once a day, once every four hours, once every 30 mins, once every minute, etc.).

Figure 86:
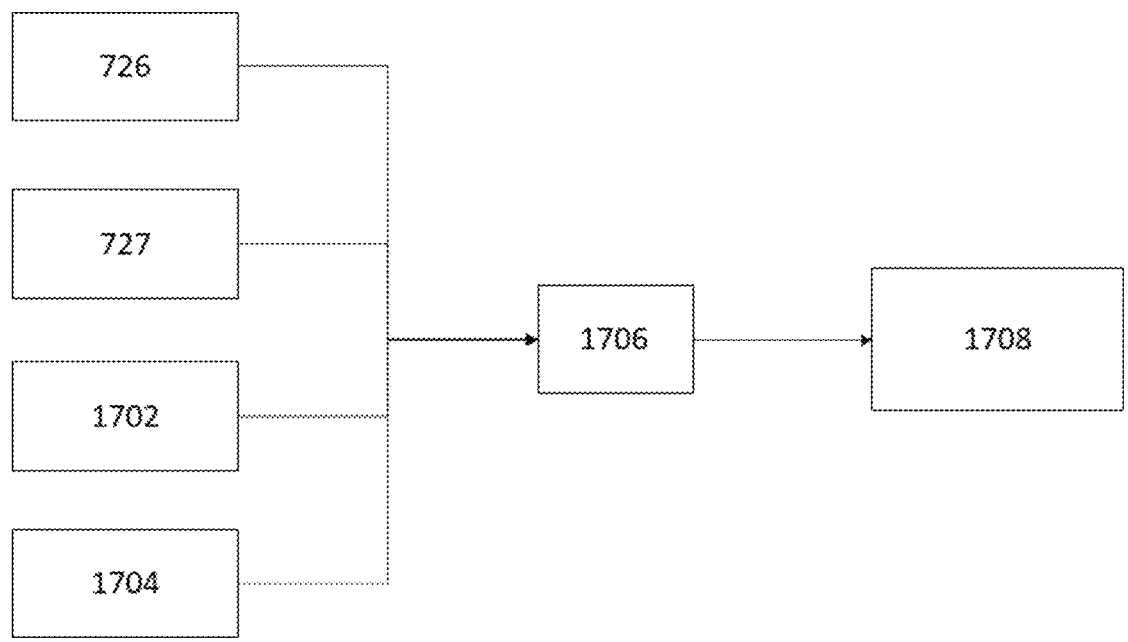
FIG. 86 illustrates a sensor data flow diagram describing one embodiment of the present invention.

FIG. 86 illustrates a sensor flow diagram describing one embodiment of the present invention. In one embodiment of the present invention, the system includes at least one environmental temperature sensor (or ambient temperature sensor) 726, at least one ambient humidity sensor 727, at least one article temperature sensor 1702, and at least one pressure sensor 1704. In one embodiment, the sensors are included within the mattress pad and/or within a mattress. In another embodiment, the sensors are included in a separate sensor strip lain on top of, beneath, or beside of the mattress pad. In one embodiment, the at least one article temperature sensor 1702 is operable to detect the temperature of the mattress pad, the mattress, a blanket, and/or the user, while the environmental temperature sensor 726 is operable to detect the temperature of the ambient environment (e.g., room temperature). Because the mattress pad is thermally regulated in one embodiment of the present invention, it is useful to determine the temperature of the mattress pad as distinct from the ambient temperature of the environment to understand the efficiency of the thermal regulation system. In one embodiment, the pressure sensor 1704 is a four-channel pressure sensor, wherein the pressure sensor 1704 includes leads that detect the pressure of four different areas.

In one embodiment, a GUI is operable to manage the ownership and connection between various sensors. For example, in one embodiment, the system includes a selection from a user device requesting an association of two pressure sensors, two ambient temperature sensors, one article temperature sensor, and one humidity sensor into a single collection. In one embodiment, if the system detects that a sensor is missing that is needed to calculate an important sleep parameter (e.g., no pressure sensor is in a collection), then a warning message is sent to the user device. Allowing a user to separate sensors into different collections allows for users to better divide calculated parameters for a single user in a multi-user household. For example, for two people occupying the same bed, it is often useful to separate the parameters calculated for one person on one side of the bed from those on the other side of the bed. However, in one embodiment, the sensors in each collection are operable to communicate data with each other. This is helpful, for instance, when one user's body temperature is particularly hot at night, which affects the calculated temperatures by the sensors for another user on the same bed. In some instances, for example, this increased user temperature contributes to different ambient or article temperature detection for another user, which results in incorrect core body temperature calculation. However, when the hotter user's article temperature sensor communicates sensor data with the other user's article temperature sensor and/or ambient temperature sensor, then the other user's sensor processing module 1706 is able to factor this sensor data into its calculations and thereby correct errors in core body temperature calculation.

The sensor data processed in a sensor processing module 1706 in order to derive data related to the user. In one embodiment, the sensor processing module 1706 is included in an enclosure adapted to connected to each of the sensors. In one embodiment, the enclosure is adapted to sit on a bedside table of a user. In one embodiment, the sensors are connected to the sensor processing module 1706 through a wired connection and/or a wireless connection (e.g., WI-FI) as part of an Internet of Things (IoT) system.

In one embodiment, the sensor data is used by the sensor processing module 1706 to derive the heart rate (e.g., through ballistocardiography), heart rate variability, respiration rate, time asleep, time awake, and/or in-bed/out-of-bed state of the user. In one embodiment, data produced by the sensors and the sensor processing module 1706 are provided to the user in the form of a sleep report 1708. In one embodiment, the sleep report 1708 includes heart rate variability (including a low frequency and a high frequency during a time period), core body temperature, average heart rate during a time period, average respiration rate during a time period, total time in bed during a time period, total time out of bed during a time period, total time asleep during a time period, total time spent in REM sleep during a time period, total time spent in light sleep during a time period, total time spent in deep sleep during a time period, total time awake during a time period, sleep latency, the presence of disturbances and/or movement during a time period, and/or a hypnogram for a time period. In one embodiment, the system is operable to receive selection specifying which quantities a user wants to receive in their individual sleep report 1708. By way of example and not of limitation, time periods include 2 hours. 4 hours, 8 hours, 24 hours, 72 hours, and/or 168 hours. In one embodiment, time periods start when a start selection is received from a user device and/or end when an end selection is received from a user device. In another embodiment, users are able to select time periods over which a sleep report 1708 is generated.

The core body temperature of a user is able to be calculated using the data from the article temperature sensor 1702 and/or the environmental temperature sensor 726, for example, through the method described in "Estimation of core body temperature from skin temperature, heat flux, and heart rate using a Kalman filter" by Welles et al., 99 *Computers in Biology and Medicine* 1 (August 2018), which is incorporated herein by reference in its entirety. By way of example and not of limitation, in one embodiment, article temperature sensor data is used to determine skin temperature, which is in turn used to determine core body temperature. Furthermore, in one embodiment, the core body temperature is used to estimate whether the user is asleep or awake, in line with the findings of "Galanin neurons in the ventrolateral preoptic area promote sleep and heat loss in mice," by Kroeger et al., *Nature Communications* 9 (2018), which is incorporated herein by reference in its entirety.

In one embodiment, the sleep report 1708 includes a sleep score for a time period. In one embodiment, the sleep score is based on a number of factors, including respiration rate, heart rate, heart rate variability, data from the article temperature sensor, ambient temperature, ambient humidity, and/or continuous time in bed. In one embodiment, the sleep score includes a letter grade and/or a numerical rating assessing the quality of the user's sleep. In another embodiment, the sleep score categorizes the user's sleep into one of a few different categories, such as "great sleep," "good sleep," or "restless sleep." In one embodiment, the sleep score includes four different categories. In one embodiment, an artificial intelligence module is operable to generate at least one suggestion to the user for improving sleep based on the user's sleep report and/or other sleep data.

In one embodiment, the mattress pad is a thermally regulated article connected to at least one fluid inlet line and at least one fluid outlet line. Fluid passes into the mattress pad through the fluid inlet line from a control unit connected to the at least one fluid inlet line and the at least one fluid outlet line. The control unit is operable to heat and/or cool the fluid using one or more thermoelectric modules. In one embodiment, the system includes at least one fluid inlet temperature sensor and/or at least one fluid outlet temperature sensor. The at least one fluid inlet temperature sensor is connected to the at least one fluid inlet line, such that it detects the temperature of fluid passing into the mattress pad. The at least one fluid outlet temperature sensor is connected to the at least one fluid outlet line, such that it detects the temperature of fluid passing out of the mattress pad. In one embodiment, the mattress pad is operable to modulate the heating or cooling done by one or more thermoelectric modules in the control unit based on data received by the at least one fluid inlet temperature sensor and/or the at least one fluid outlet temperature sensor. By calibrating the system based on the temperature of the inlet lines and/or the outlet lines, the system is able to adjust the temperature to the specific user and provide optimal heating and/or cooling agnostic of, for example, the amount of heat put off by the user.

Furthermore, in one embodiment, data produced by the at least one fluid inlet temperature sensor and/or the at least one fluid outlet temperature sensor is used to calculate the amount of heat given off by a user during a specific time period. Furthermore, in another embodiment, the amount of heat given off by a user is determined by the amount of power drawn by the one or more thermoelectric modules while maintaining a constant temperature. In one embodiment, the amount of heat put off by a user is compared across time periods in order to provide feedback to the user regarding sleep performance by day (or by other periods of time) and to provide information about optimal personal parameters for facilitating sleep. In one embodiment, these calculations are used, for example, to determine a core body temperature of the user.

In one embodiment, the system includes a platform connected to a database operable to store a plurality of user profiles. In one embodiment, the platform is an Internet of Things (IoT) platform as described in U.S. patent application Ser. No. 17/407,854, which is incorporated herein by reference in its entirety. In one embodiment, the database further includes a plurality of device groupings. Device groupings are defined associations between different user devices (e.g., a control unit for heating and/or cooling an article, a light generating unit, a sound generating unit, a pulsed electromagnetic field therapy (PEMF) unit, a virtual reality and/or augmented reality device, one or more tracker, etc.). Device groupings are particularly useful in situations in which multiple users regularly occupy the same space. If one user profile is associated with devices in one part of the space and another user profile is associated with devices in a second part of the space, then those user profiles are able to have independent settings catered to the individual preferences of the users. Furthermore, in the event that one of the users leaves the space, remaining users are able to associate with different device groupings that better match their preferences based on the absence of the other user.

In one embodiment, device groupings have preset rules regarding how many devices of each device are able to included in each group (e.g., only one of each type of tracker is able to be included in each device grouping). The platform is able to associate a user profile with a device grouping upon receiving a selection of the device grouping from a user device associated with the user profile. In one embodiment, when the user profile is associated with the device grouping, user preferences associated with the user profile are used to determine the settings of the devices within the device grouping. By way of example and not of limitation, in one embodiment, a user profile includes preferences for an article temperature of 65° F. and a low light setting. When the user profile is associated with a device grouping including a control unit for heating and/or cooling an article and a light generating unit, those preferences are implemented.

In one embodiment, if a device grouping includes a device for which preferences have not been selected in the user profile, then the device will operate on a default settings mode. In another embodiment, the device for which preferences have not been selected will not run. In yet another embodiment, manual input commands are received from a user device in order to operate the device for which preferences have not been selected. In still another embodiment, an artificial intelligence module automatically determines preferences for the device for which preferences have not been selected based on other data associated with the user profile (e.g., preferences for other devices, previous sleep tracker data, etc.).

In one embodiment, the association between a user profile and a device grouping is made after the platform receives a selection of the device grouping from a user device associated with the user profile. In another embodiment, the association is made automatically based on the geolocation of the user associated with the user profile. By way of example and not of limitation, in one embodiment, a user has two residences, each with its own device grouping. When the user exits one residence and enters the other residence, the platform automatically associates the user profile of the user with the device grouping at the new residence based on the user's geolocation. In one embodiment, the geolocation of the user is determined by a geolocation sensor (e.g., a GPS chip in a cellular telephone of the user). In another embodiment, the geolocation of the user is determined by one or more trackers in the device grouping with which the user profile is newly associated (e.g., a pressure sensor detects pressure from the user).

In one embodiment, a single device is able to be grouped into multiple device groupings. However, because many devices cannot cater to multiple different user settings simultaneously, in one embodiment, the device is only able to be actively operated within a single device grouping at any one time. In one embodiment, if a first profile is associated with a first device grouping containing a particular device, and a second profile then associates with a second device grouping containing the same particular device, then the particular device is operated according to the preferences of the second profile and the other devices in the first device grouping continue to operate according to the preferences of the first profile. In another embodiment, the selection by the second profile automatically deactivates any association between the first profile and the first device grouping. In yet another embodiment, the second profile is unable to associate with the particular device until the first profile disassociates with the particular device.

Figure 87:
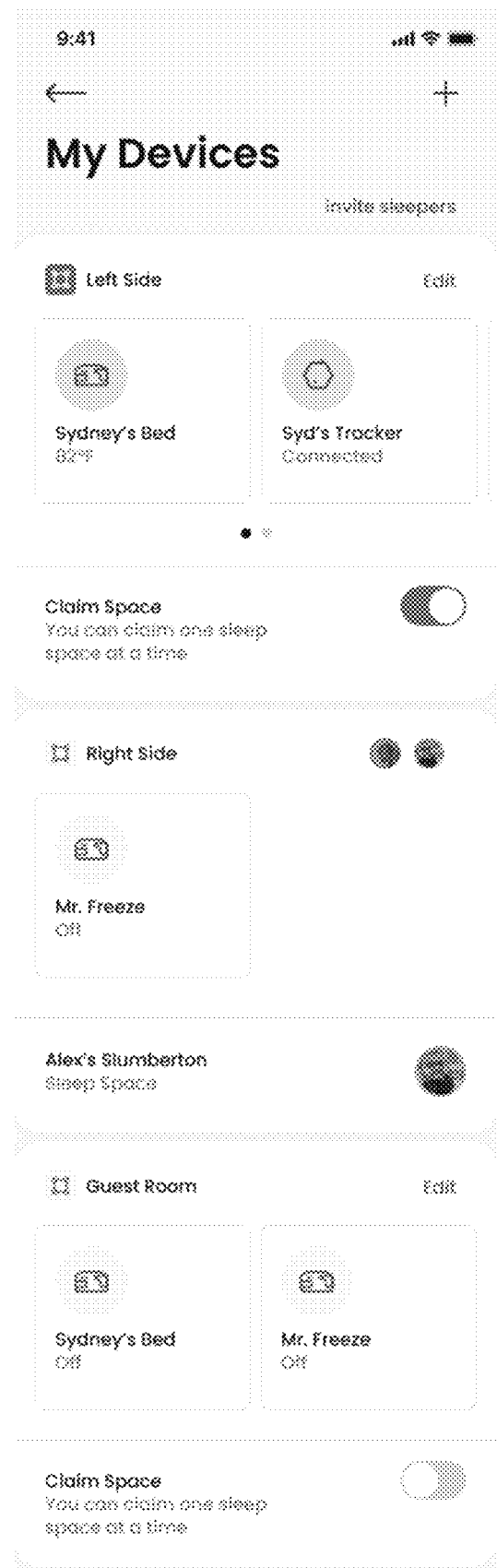
FIG. 87 illustrates a list of different device groupings according to one embodiment of the present invention.

FIG. 87 illustrates a list of different device groupings according to one embodiment of the present invention. In one embodiment, a graphical user interface (GUI) provided on a user device is operable to display a list of device groupings, such as "Left Side," "Right Side," and "Guest Room." One or more devices is associated with each of the device groupings, with icons shown under the name of the device to provide information regarding the types of devices in the device grouping for a user. In one embodiment, the GUI is operable to receive a selection (e.g., click selection) to "claim space" under each device grouping. In one embodiment, if another user profile has already associated with a particular device grouping, an option is not provided to claim that device grouping. In one embodiment, the list of device groupings includes an option to "Invite sleepers," which allows a user to select other individual user profiles to be able to claim one or more of their own device groupings. As shown in FIG. 87, in one embodiment, each user profile is associated with a profile picture in the GUI for the device groupings. In one embodiment, each device grouping listed includes a button linked to an Edit interface for the device grouping.

Figure 88:
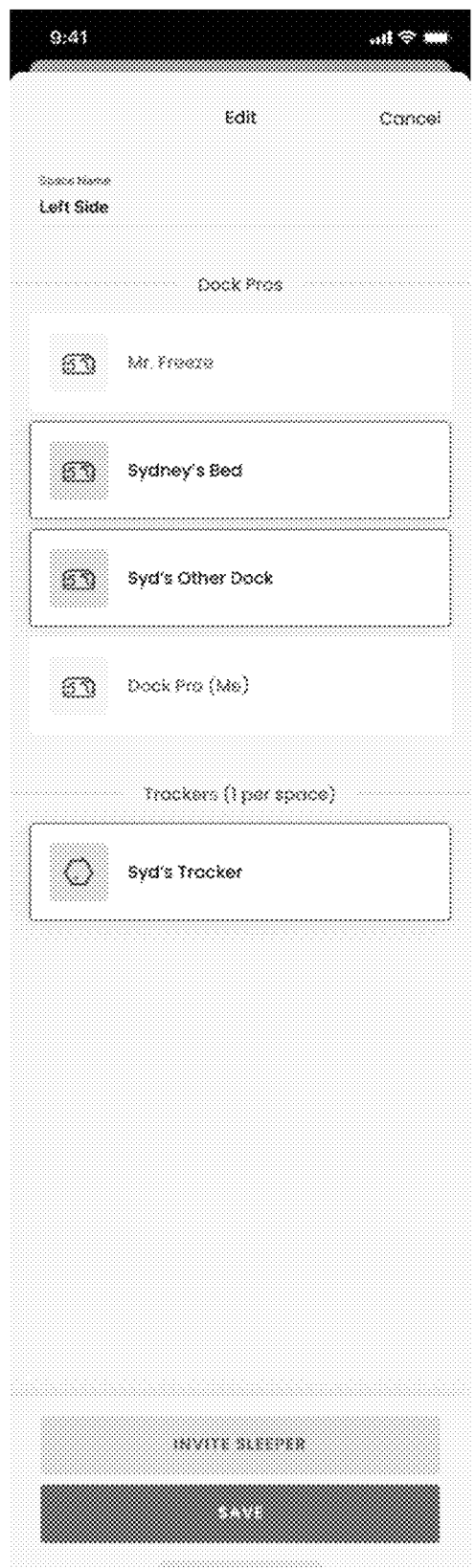
FIG. 88 illustrates an Edit interface for a device grouping according to one embodiment of the present invention.

FIG. 88 illustrates an Edit interface for a device grouping according to one embodiment of the present invention. In one embodiment, an Edit interface for a device grouping is operable to receive an input to change the name of the device grouping. In one embodiment, the Edit interface includes a list of devices able to be associated with device grouping, with the devices sorted by the type of device. In one embodiment, if a device is already claimed, then the device will appear grey or be otherwise indicated to be claimed on the Edit interface. In one embodiment, the Edit interface is operable to receive a selection to save the change in settings. In one embodiment, the Edit interface is operable to receive a selection to invite another user to claim the space, which causes the platform to automatically send a message inviting the user to claim the space.

Figure 89:
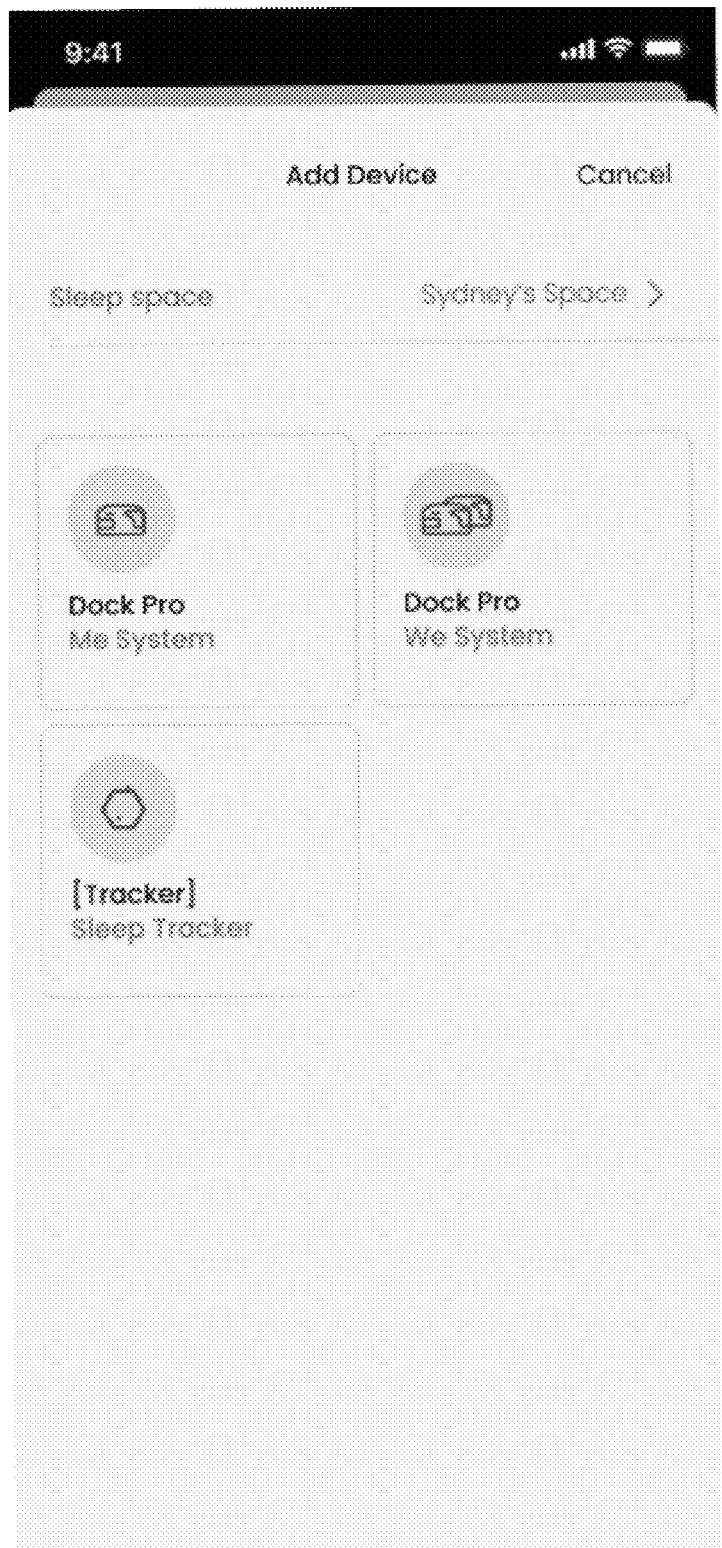
FIG. 89 illustrates an Add Device interface according to one embodiment of the present invention.

FIG. 89 illustrates an Add Device interface according to one embodiment of the present invention. In one embodiment, devices are only able to be included in a device grouping if they have already been added through the Add Device interface. In one embodiment, the Add Device interface is operable to receive a selection of a type of device to add (e.g., a control unit for heating and/or cooling a surface, a light generating unit, a tracker, etc.). In one embodiment, after the selection of the type of device is received, the platform is operable to receive a media access control address (MAC address), an Internet Protocol (IP) address, and/or another unique identifier for the device in order to add it to the platform. In another embodiment, after the selection of the type of device is received, the platform enters sync mode wherein it automatically detects and adds nearby devices connected through BLUETOOTH, WI-FI, and/or other networks.

The present invention is operable to be integrated into a smart home Internet of Things (IoT) environment. In one embodiment, the platform is operable to receive data from one or more IoT appliances over a network (e.g., WI-FI, BLUETOOTH, cellular, etc.). In one embodiment, the platform is operable to send commands to one or more IoT appliances over a network (e.g., WI-FI, BLUETOOTH, cellular, etc.). In one embodiment, the platform is operable to receive a registration of one or more IoT appliances with a user profile, enabling data to be received from the one or more IoT appliances in association with the user profile and/or enabling commands to be send from a mobile application by the user profile to control the one or more IoT appliances. In one embodiment, the one or more IoT appliances are associated with one or more collections in the user profile. In one embodiment, the platform is operable to automatically send commands to the one or more IoT appliances based on the sensor data, including, but not limited to, the heart rate, the heart variability, the respiration rate, the time sleep, the time awake, the body temperature, and/or the in-bed/out-of-bed state of the user. In a preferred embodiment, the platform is operable to automatically send commands to the one or more IoT appliances based on a sleep stage of the user and/or based on a smart alarm associated with the user profile. In one embodiment, the user profile is associated with one or more settings for each of the one or more IoT appliances, wherein the one or more settings include, by way of example and not of limitation, a timing for when the one or more IoT appliances are activated, a preferred network over which to communicate with the one or more IoT appliances, and other settings relevant to the individual appliance. IoT appliances able to be used with the present invention include, but are not limited to, smart scales, smart refrigerators, smart toilets, smart exercise equipment (e.g., PELOTON bike, TEMPO STUDIO equipment, etc.), smart light bulbs, smart night lights, smart speakers, smart thermostats (e.g., GOOGLE NEST, ECOBEE, etc.), smart humidifiers, smart dehumidifiers, smart coffee pots (e.g., BREWGENIE BG120), smart tea makers, smart water heaters, smart alarm clocks, smart displays (e.g., ALEXA ECHO SHOW), smart televisions, smart sprinklers (e.g., RACHIO), smart lawn mowers (e.g., HUSQVARNA AUTOMOWER, WORX LANDROID, etc.), smart vacuums (e.g., ROOMBA), smart doorbells (e.g., RING doorbell), smart locks (e.g., AUGUST HOME SMART LOCK, WYZE LOCK, GOOGLE NEST YALE LOCK, etc.), smart ovens (e.g., AMAZON SMART OVEN, TOVALA SMART OVEN, etc.), smart microwaves, smart showers (e.g., KOHLER MOXIE, THERMASOL SMART SHOWER, GROHE RAINSHOWER, etc.), smart mirrors (e.g., IHOME VANITY MIRROR, BONNLO BATHROOM MIRROR, BYECOLD VANITY MIRROR, etc.), smart garage door openers (e.g., CHAMBERLAIN MYQ, TAILWIND IQ3, GARADGET, etc.), smart thermoregulated mattress pad, smart thermoregulated blanket, smart thermoregulated pillow, smart pulsed electromagnetic field (PEMF) generator, and any other device operable for communication with the platform of the present invention. In one embodiment, the one or more IoT appliances includes an in-line fluid cooling system, operable to heat or cool an apparatus such as a mattress pad or a blanket, as described in U.S. Provisional Patent Application No. 63/287,237, which is incorporated herein by reference in its entirety.

A smart refrigerator according to the present invention is a refrigerator capable of tracking what items are currently inside of the smart refrigerator and times at which those items are removed and/or put back. Furthermore, for items such as milk containers, the smart refrigerator is capable of detecting a change in weight of the item after it is inserted back into the smart refrigerator in order to determine the volume of fluid removed from the container. In one embodiment, the smart refrigerator is capable of receiving information regarding health information for each item (e.g., calorie amount, nutrient data, etc.). The smart refrigerator is additionally capable of transmitting information over a network.

In one embodiment, the platform includes an artificial intelligence-based schedule analyzer module, operable to determine what settings should be implemented for devices or which devices should be turned on or off shortly before waking and/or shortly before going to bed. In one embodiment, the schedule analyzer module receives data from each of the one or more IoT appliances regarding a time when the device was turned on, how long the device was turned on, and/or settings implemented or changed for the device. In one embodiment, the user profile includes a setting to activate or deactivate the schedule analyzer module. In one embodiment, when the schedule analyzer module is activated, the schedule analyzer module determines which activities are routine before or after sleep after analyzing data for a predetermined amount of time (e.g., 3 days, one week, two weeks, three weeks, one month, three months, six months, etc.). In one embodiment, activities determined to be routine by the schedule analyzer module are automatically performed (e.g., devices are turned on to determined routine settings) by the platform before the user goes to sleep, after the user awakes, and/or shortly before a user awakes. In one embodiment, activities are not scheduled to be automatically performed if the scheduled activity conflicts with an existing setting for the user profile. By way of example and not limitation, even if the schedule analyzer determines the usage of a coffee machine each morning to be routine, the coffee machine will not automatically be set to turn on when the user wakes up if the user profile includes a setting specifically choosing to not turn on the coffee machine in the morning.

In one embodiment, the schedule analyzer module is connected to a global intelligence module, wherein the global intelligence module is operable to integrate data from one or more smart appliances for a plurality of users. The schedule analyzer module is therefore able to generate suggested activities and/or suggested settings based on a larger pool of data in order to inform decisions.

One use of smart home integration for the present invention is to automate a user's wake-up routine, to increase comfort and efficiency in getting prepared in the morning. As such, the platform is operable to turn on one or more appliances when a user has woken up. In one embodiment, a user having woken up is detected based on sensor data, including a detected sleep stage for the user (e.g., biometric sensor data indicates that the user is no longer asleep) and/or an in-bed/out-of-bed determination (e.g., based on data from a movement and/or body weight sensor). In one embodiment, the platform is operable to turn on one or more IoT appliances when a user is about to wake up. In one embodiment, the platform determines when a user is about to wake up based on sleep stage data (e.g., user enters light sleep)

and/or at a preset time before a set wake-up alarm (e.g., one minute before, five minutes before, ten minutes before, thirty minutes before, etc.). In one embodiment, the platform does not automatically turn on one or more IoT appliances when the user wakes up or is about to wake up if the user is waking during an unusual time period. In one embodiment, "unusual time periods" are automatically set in association with a user profile based on the user's typical schedule (e.g., if the user usually wakes up at 8 AM on Tuesday, the user waking at 4 AM on Tuesday is a designated unusual time period). In one embodiment, "unusual time periods" are manually set in association with a user profile. In one embodiment, "unusual time periods" are preset times for all user profiles (e.g., between 1 AM and 5 AM).

In one embodiment, the platform is operable to automatically start and/or change a setting of one or more IoT appliances when the platform detects that a user has woken up or is about to wake up. By way of example and not of limitation, in one embodiment, the platform is operable to start a coffee maker and/or tea maker when the platform detects that a user has woken up or is about to wake up (e.g., when the user enters a light sleep, 5 minutes before a scheduled alarm timer, etc.). In one embodiment, settings in the user profile for the coffee maker and/or tea maker include a type of coffee and/or tea, a temperature of the coffee and/or tea, a volume of coffee and/or tea, and/or a strength of the coffee and/or tea. In one embodiment, if the coffee maker is set to be activated based on an alarm timer and the platform detects that the user remains sleeping after the alarm timer goes off, then the platform automatically turns off the coffee maker, so as to prevent wasted energy and/or decrease risk of fire.

In one embodiment, the platform is operable to automatically turn on a smart television when the platform detects that a user has woken up or is about to wake up (e.g., when the user enters a light sleep, 5 minutes before a scheduled alarm timer, etc.). In one embodiment, settings in the user profile for the smart television include, but are not limited to, one or more designated channels and/or applications (e.g., NETFLIX, AMAZON PRIME, YOUTUBE, etc.) including one or more designated shows or programs which are operable to be selected based on a viewing history of a user account and/or a date and time, a volume, a brightness, and/or a time before or after waking when the smart television is set to turn on.

In one embodiment, the platform is operable to automatically turn on a smart shower when the platform detects that a user has woken up or is about to wake up (e.g., when the user enters a light sleep, 5 minutes before a scheduled alarm timer, etc.). In one embodiment, settings in the user profile for the smart shower include, but are not limited to, a temperature, an intensity, and/or a maximum amount of time for the shower to operate. Additionally, or alternatively, a water heater is operable to be automatically turned on when the platform detects that a user has woken up or is about to wake up (e.g., when the user enters a light sleep, 5 minutes before a scheduled alarm timer, etc.).

In one embodiment, the platform is operable to automatically turn on and/or change a setting for one or more smart light bulbs when the platform detects that a user has woken up or is about to wake up (e.g., when the user enters a light sleep, 5 minutes before a scheduled alarm timer, etc.). In one embodiment, settings in the user profile for the one or more smart light bulbs include, but are not limited to, a color and/or a brightness. By way of example and not of limitation, in one embodiment, the one or more smart light bulbs are programmed to emit a dim red light when the user is asleep and turn on a brighter yellow light when the user is awake. In one embodiment, the platform does not automatically turn nor change a setting for the one or more smart light bulbs if the user wakes up during a low light time (e.g., the middle of the night) so as not to overwhelm the user with light. In one embodiment, light level is determined based on at least one light sensor in communication with the platform. In another embodiment, light level is estimated based on the time of day, time of the year, and/or the geographical location of the platform.

In one embodiment, the platform is operable to automatically turn on or change a setting for a smart thermostat when the platform detects that a user has woken up or is about to wake up (e.g., when the user enters a light sleep, 5 minutes before a scheduled alarm timer, etc.). In one embodiment, settings in the user profile for the smart thermostat include, but are not limited to, a set temperature (or a range of temperatures) and/or a set relative humidity (or range of relative humidities). Changing a setting of the smart thermostat to warm when the user wakes up both allows the room to feel more comfortable for the user and assists in waking the user up.

In one embodiment, the platform is operable to automatically turn on a night light associated with a smart toilet when the platform detects that a user has woken up or is about to wake up (e.g., when the user enters a light sleep, 5 minutes before a scheduled alarm timer, etc.). In one embodiment, the night light is only turned on if the user wakes up during a low light time (e.g., the middle of the night). Alternatively, a plurality of smart night lights not associated with any other smart devices are operable to be turned on when the platform detects that a user has woken up or is about to wake up (e.g., when the user enters a light sleep, 5 minutes before a scheduled alarm timer, etc.).

In one embodiment, the platform is operable to automatically generate one or more suggested activities (e.g., an exercise, a meditation routine, a breakfast food, one or more news articles to read, etc.) on at least one smart display and/or at least one smart mirror. In one embodiment, the platform is operable to automatically display a daily and/or weekly personal schedule on the at least one smart display and/or the at least one smart mirror. In one embodiment, the platform is operable to automatically display a daily and/or weekly weather schedule on the at least one smart display and/or the at least one smart mirror. In one embodiment, the one or more suggested activities are generated by an artificial intelligence recommendation engine based on historical sensor data for the user. In another embodiment, the user profile includes at least one user-generated suggested activity, including a designated morning on which to display the at least one user-generated suggested activity.

Another use of smart home integration for the present invention is to automate a user's bedtime routine, to increase comfort and efficiency in getting into bed and increase safety before the user falls asleep. For example, in one embodiment, when the platform detects that the user is asleep or in the process of falling asleep, the platform automatically locks all exterior smart locks (i.e., smart locks for exterior doors) in the home that were not previously locked. This helps to prevent instances in which the user forgets to lock the door before sleeping and is therefore left vulnerable to break-ins. In one embodiment, when the platform detects that the user is asleep or in the process of falling asleep, the platform automatically turns off any smart ovens and/or smart microwaves that are currently running. This helps prevent accidental fires that frequently occur when ovens or microwaves are left running unattended. In one embodiment, when the platform detects that the user is asleep or in the process of falling asleep, the platform automatically turns on a smart thermostat and/or turns on a smart heating, ventilation, and air conditioning (HVAC) unit and/or changes a setting for the smart thermostat or smart HVAC unit. Changing the setting of the smart thermostat to cool when the user falls asleep both allows the room to feel more comfortable for the user and assists in helping the user sleep. In one embodiment, when the platform detects that the user is asleep or in the process of falling asleep, the platform automatically turns on a smart humidifier and/or turns off a smart dehumidifier.

Furthermore, integration of smart home appliances with the present invention allows the platform to prevent potentially disturbing devices from operating while a user is asleep. By way of example and not of limitation, in one embodiment, if the platform detects that the user is asleep, the platform prevents operation of at least one smart doorbell. However, in one embodiment, the user profile includes a list of one or more individuals who are permitted to utilize the at least one smart doorbell even if the user is asleep. In one embodiment, the presence of the one or more permitted individuals is determined based on detection of at least one user device associated with the one or more permitted individuals within a geofence around the at least one smart doorbell. In another embodiment, the user profile includes at least one override code. If the override code is entered through the at least one smart doorbell (or through a mobile application), then the at least one smart doorbell is permitted to operate even while the user is asleep. In one embodiment, if the platform detects that the user is asleep, the platform prevents operation of at least one smart lawnmower, at least one smart sprinkler, at least one smart vacuum, and/or any other type of smart device that makes significant noise even if those smart devices were scheduled to operate. In one embodiment, the platform does not prevent operation of the at least one smart lawnmower, the at least one smart sprinkler or the at least one smart vacuum, but restricts the geographical area in which those devices (e.g., bars the devices from entering an adjacent room) are able to operate based on the location where the user is asleep.

Smart home integration also allows for the generation of more nuanced and more sophisticated health data, which is able to be used by at least one artificial intelligence-based health monitoring module to generate health recommendations and/or calibrate at least one thermally regulated article. By way of example and not of limitation, the health monitoring module is able to receive body weight data, hydration data, muscle mass data, fat-free body weight data, basal metabolic rate data, metabolic age data, and/or body fat data from at least one smart scale, data regarding what a user has eaten and when the user ate it from at least one smart refrigerator, data regarding how much the user has exercised and what forms of exercise were used, and/or information regarding how much the user is using the restroom and at what points in time via at least one smart toilet. In one embodiment, the platform is operable to receive additional data regarding what a user eats through integration with a food delivery application (e.g., DOORDASH, GRUBHUB, UBER EATS, etc.), or through manual entry through an application on a user device. In one embodiment, the platform is operable to receive additional data regarding a user's exercise through communication with at least one wearable device (e.g., OURA RING, APPLE WATCH, FITBIT, etc.) and/or through manual entry through an application on a user device.

In one embodiment, the platform is operable to automatically alter a sleep program based on data received by the health monitoring module. By way of example and not of limitation, if a user eats a meal shortly before going to sleep (as detected by the smart fridge), then the sleep program automatically decreases an average temperature for at least one thermoregulated article used by a user in order to ensure the user is able to remain in deep sleep, and is not awakened due to the late-night food consumption.

In one embodiment, the platform is operable to present an offer to the user profile to participate in a sleep study. In one embodiment, if the user profile chooses to participate in the sleep study, then a quantity of money and/or credits are automatically transmitted to the user profile and/or at least one financial account associated with the user profile. In one embodiment, the quantity of money and/or credits are transferred to the user profile and/or the at least one financial account associated with the user profile at regular intervals (e.g., every day, every week, every two weeks, every month, every year, etc.). If the platform receives a selection to opt in to the sleep study, then the platform is permitted to transmit sleep data and/or data received by the health monitoring module to at least one third-party data collector. Beneficially, the platform therefore allows conductors of sleep studies to determine the effects of different variables (e.g., body weight, eating patterns, exercise patterns) on sleep while controlling for other confounding variables. For example, in one embodiment, the platform automatically separates participants into cohorts based on body weight and amount of exercise in order to isolate the effects of eating sugary foods on sleep. Additionally, because individuals are able to opt in and participate from home, the number of participants (and therefore the quantity of data) is greatly enhanced, such that more accurate data is able to be produced.

In one embodiment, at least one wake up setting and/or at least one goodnight setting for the at least smart appliance depends upon a sleep score for the user during the previous night. In another embodiment, the at least one wake up setting and/or the at least one goodnight setting for the at least one smart appliance depends upon a sleep score for the user over a predetermined time period (e.g., 3 days, one week, one month, one year, etc.). By way of example and not of limitation, in one embodiment, if the platform determines that a user did not receive a good night's sleep, then a smart coffee pot is commanded to produce coffee having additional caffeine (e.g., a double espresso), but if the platform determines that a user did receive a good night's sleep, then the smart coffee pot is commanded to produce coffee having less caffeine (e.g., a single espresso). In another non-limiting example, the platform is operable to choose a channel, a streaming service, and/or a specific item of media for a wake up setting for at least one smart television based on the user's sleep score. In one embodiment, variations in wake up settings and/or goodnight settings are set in the user profile. In another embodiment, variations in wake up settings and/or goodnight settings are automatically determined by an artificial intelligence module.

In one embodiment, the platform includes a virtual shopping cart associated with each user profile. The virtual shopping cart is able to receive selections of one or more items to buy. In one embodiment, the virtual shopping cart is configured to interface with a third-party API for a retail site (e.g., Amazon). In one embodiment, the platform is operable to add suggested items to the virtual shopping cart based on habits determined by the schedule analyzer module and/or based on a sleep score for the user. By way of example and not limitation, in one embodiment, the platform automatically suggests new coffee pods when the platform determines that the user is likely out of coffee. In another example, the platform automatically suggests purchasing a stress reliever when an abnormally low sleep score is generated for the user.

In one embodiment, each smart appliance is able to be associated with one or more device groupings, wherein each device grouping is associated with a different user. In one embodiment, smart appliances only provide data regarding a user and are only set to automatically turn on, turn off, and/or change settings according to sleep data associated with a user if the smart appliance is in a device grouping associated with that user. In one embodiment, some smart appliances are only able to be associated with one device grouping, especially those where conflicting settings are likely and/or particular problematic. For example, in one embodiment, a smart television is only able to be placed in a single device grouping, as conflicting wake up channel settings would be likely and problematic. In one embodiment, some smart appliances are able to be placed in more than one device grouping, but certain settings for each smart appliance are locked to a single user. For example, a smart television is able to be placed in multiple device groupings, but the wake up channel settings are only able to be set by a single user. In one embodiment, there are no restrictions regarding how many different device groupings a smart appliance is able to occupy. For example, a smart coffee maker is able to be in multiple device groupings, as different user preferences for a single smart coffee maker do not tend to create a conflict, but rather merely increase the amount produced by the smart coffee maker. In one embodiment, when a smart appliance is in multiple device groupings and given multiple commands at about the same time (e.g., multiple users wake up at approximately the same time), then the smart appliance is set to automatically prioritize which wake up protocol to enact first based on sleep data from users associated with each of the multiple device groupings. For example, if a smart coffee maker detects that one user had poor sleep and requires a double espresso, while another user had good sleep and only requires a single espresso, then the smart coffee maker is able to automatically prioritize making the double espresso.

Figure 90:
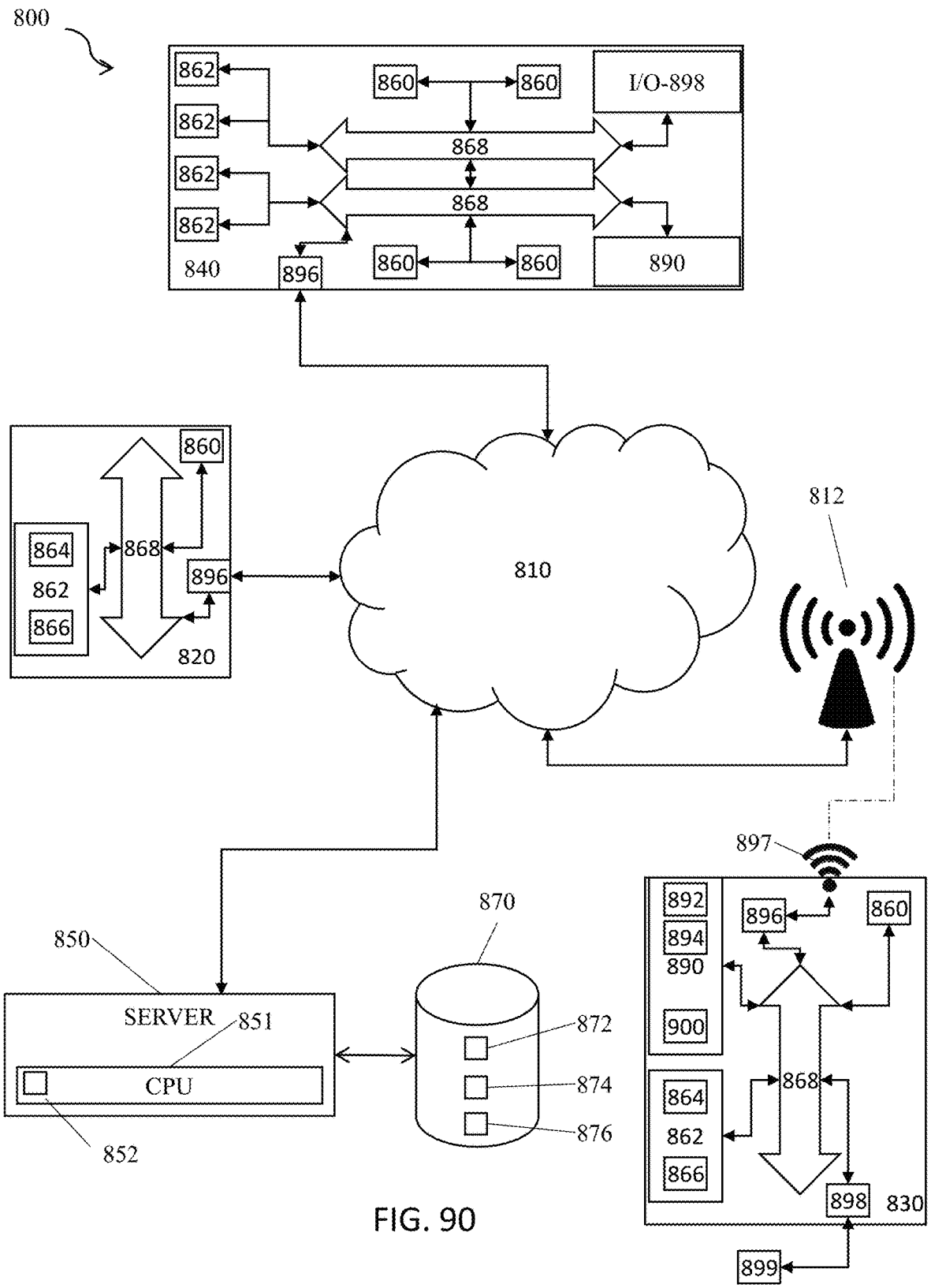
FIG. 90 shows a schematic diagram illustrating general components of a cloud-based computer system.

FIG. 90 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 houses an operating system 872, memory 874, and programs 876.

In one embodiment of the invention, the system 800 includes a cloud-based network 810 for distributed communication via a wireless communication antenna 812 and processing by at least one mobile communication computing device 830. In another embodiment of the invention, the system 800 is a virtualized computing system capable of executing any or all aspects of software and/or application components presented herein on the computing devices 820, 830, 840. In certain aspects, the computer system 800 is able to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is able to additionally include components such as a storage device 890 for storing the operating system 892 and one or more application programs 894, a network interface unit 896, and/or an input/output controller 898. Each of the components is able to be coupled to each other through at least one bus 868. The input/output controller 898 is able to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 includes a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that are able to perform calculations, process instructions for execution, and/or other manipulations of information.

In another implementation, shown as 840 in FIG. 90, multiple processors 860 and/or multiple buses 868 are able to be used, as appropriate, along with multiple memories 862 of multiple types (e.g., a combination of a DSP and a microprocessor, a plurality of microprocessors, one or more microprocessors in conjunction with a DSP core).

Also, multiple computing devices are able to be connected, with each device providing portions of the necessary operations (e.g., a server bank, a group of blade servers, or a multi-processor system). Alternatively, some steps or methods are able to be performed by circuitry that is specific to a given function.

According to various embodiments, the computer system 800 operates in a networked environment using logical connections to local and/or remote computing devices 820, 830, 840, 850 through a network 810. A computing device 830 is able to connect to a network 810 through a network interface unit 896 connected to a bus 868. Computing devices are able to communicate communication media through wired networks, direct-wired connections or wirelessly, such as acoustic, RF, or infrared, through an antenna 897 in communication with the network antenna 812 and the network interface unit 896, which include digital signal processing circuitry when necessary. The network interface unit 896 is able to provide for communications under various modes or protocols.

In one or more exemplary aspects, the instructions are able to be implemented in hardware, software, firmware, or any combinations thereof. A computer readable medium is able to provide volatile or non-volatile storage for one or more sets of instructions, such as operating systems, data structures, program modules, applications, or other data embodying any one or more of the methodologies or functions described herein. In one embodiment, the computer readable medium includes the memory 862, the processor 860, and/or the storage media 890 and is a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further able to be transmitted or received over the network 810 via the network interface unit 896 as communication media, which includes a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that is able to be used to store the computer readable instructions and which is able to be accessed by the computer system 800.

It is also contemplated that the computer system 800 is able to not include all of the components shown in FIG. 90, is able to include other components that are not explicitly shown in FIG. 90, and is able to utilize an architecture completely different than that shown in FIG. 90. The various illustrative logical blocks, modules, elements, circuits, and algorithms described in connection with the embodiments disclosed herein are able to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans are able to implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. The above-mentioned examples are just some of the many configurations that the mentioned components are able to take on. All modifications and improvements have been deleted herein for the sake of conciseness and readability but are properly within the scope of the present invention.

The invention claimed is:

1. A sleep promotion system, comprising:
at least one body sensor in network communication with at least one remote device;
at least one smart appliance in network communication with the at least one remote device;
wherein the at least one body sensor is operable to generate and transmit sensor data to the at least one remote device in real time;
wherein the sensor data includes biometric information regarding at least one individual;
wherein the at least one remote device is operable to determine a sleep state and/or a sleep stage for the at least one individual based on the sensor data in real time;
wherein the at least one remote device is operable to generate a sleep score for the at least one individual based on the biometric information; and
wherein the at least one remote device is operable to generate at least one user profile, where the at least one user profile is associated with one or more of the at least one smart appliance, wherein the at least one user profile includes settings associated with the one or more of the at least one smart appliance to occur upon detection that the at least one individual has fallen asleep or woken up, and wherein at least one of the settings is dependent upon the sleep score of the at least one individual.

2. The system of claim 1, wherein the sleep score is based on at least an amount of time the at least one individual has slept and/or an amount of time the at least one individual has been in deep sleep.

3. The system of claim 1, wherein the at least one smart appliance includes at least one smart coffee machine, wherein the at least one smart coffee machine is operable to produce at least one cup of coffee upon detecting that the at least one individual has woken up, and wherein an amount of caffeine included in the at least one cup of coffee depends on the sleep score for the at least one individual.

4. The system of claim 1, wherein the at least one body sensor includes at least one heart rate sensor, at least one respiration sensor, at least one body temperature sensor, at least one analyte sensor, at least one brain wave sensor, at least one electromyography (EMG) sensor, at least one movement sensor, at least one body weight sensor, at least one electrooculography (EOG) sensor, at least one pulse oximeter sensor, at least one blood pressure sensor, at least one body fat sensor, and/or at least one electrodermal activity sensor.

5. The system of claim 1, wherein the at least one body sensor and/or the at least one smart appliance communicate with the at least one remote device over a WI-FI and/or BLUETOOTH network.

6. The system of claim 1, wherein the biometric information includes respiration rate, heart rate, heart rate variability, ambient temperature, ambient humidity, and/or continuous time in bed.

7. The system of claim 1, wherein the at least one smart appliance includes at least one smart television, wherein the at least one smart television is turned on when the at least one individual wakes up, and wherein a channel selection, a streaming service selection, and/or a program selection for the at least one smart television depend on the sleep score for the at least one individual.

8. The system of claim 1, wherein the at least one smart appliance includes at least one smart thermostat, and wherein a wake up temperature setting for the at least one smart thermostat depends on the sleep score for the at least one individual.

9. A sleep promotion system, comprising:
at least one body sensor in network communication with at least one remote device;
at least one smart appliance in network communication with the at least one remote device;
wherein the at least one body sensor is operable to generate and transmit sensor data to the at least one remote device in real time;
wherein the sensor data includes biometric information regarding at least one individual;
wherein the at least one remote device is operable to determine a sleep state for the at least one individual based on the sensor data;
wherein the at least one remote device is operable to generate at least one user profile, where the at least one user profile is associated with one or more of the at least one smart appliance;
wherein the at least one remote device is operable to transmit at least one participation offer to at least one user device associated with the at least one user profile; and
wherein the at least one remote device is operable to automatically transmit money and/or credits to the at least one user profile in exchange for receiving a selection to accept the at least one participation offer.

10. The system of claim 9, wherein the at least one participation offer includes at least one offer to participate in a sleep study.

11. The system of claim 9, wherein acceptance of the at least one participation offer allows the at least one remote device to transmit the sensor data and/or data from the at least one smart appliance to a third-party data collector.

12. The system of claim 9, wherein the at least one body sensor includes at least one heart rate sensor, at least one respiration sensor, at least one body temperature sensor, at least one analyte sensor, at least one brain wave sensor, at least one electromyography (EMG) sensor, at least one movement sensor, at least one body weight sensor, at least one electrooculography (EOG) sensor, at least one pulse oximeter sensor, at least one blood pressure sensor, at least one body fat sensor, and/or at least one electrodermal activity sensor.

13. The system of claim 9, wherein the at least one remote device is operable to collect and store the sensor data to generate historical biometric data associated with each of the at least one user profile, and wherein the at least one remote device is operable to change one or more settings of the at least one smart appliance based on the historical biometric data.

14. The system of claim 9, wherein the at least one smart appliance includes at least one smart exercise machine, at least one smart refrigerator, at least one smart scale, at least one smart coffee pot, at least one smart tea maker, and/or at least one smart toilet.

15. The system of claim 9, wherein the money and/or the credits are transferred at regular intervals to the at least one user profile in exchange for receiving the selection to accept the at least one participation offer.

16. A sleep promotion system, comprising:
at least one body sensor in network communication with at least one remote device;
at least one smart appliance in network communication with the at least one remote device;
wherein the at least one body sensor is operable to generate and transmit sensor data to the at least one remote device in real time;
wherein the sensor data includes biometric information regarding at least one individual;
wherein the at least one remote device is operable to determine a sleep state and/or a sleep stage for the at least one individual based on the sensor data in real time;
wherein the at least one remote device is operable to generate a sleep score for the at least one individual based on the biometric information;
wherein the at least one remote device is operable to change a setting of the at least one smart appliance upon detecting that the at least one individual has fallen asleep or woken up;
wherein the change in the setting of the at least one smart appliance is determined based on the sleep score of the at least one individual; and
wherein the at least one smart appliance includes at least one smart coffee machine,
wherein the at least one smart coffee machine is operable to produce at least one cup of coffee upon detecting that the at least one individual has woken up, and wherein an amount of caffeine included in the at least one cup of coffee depends on the sleep score for the at least one individual.

17. The system of claim 16, wherein the at least one remote device is operable to generate at least one user profile, where the at least one user profile is associated with one or more of the at least one smart appliance, wherein the at least one user profile includes settings associated with the one or more of the at least one smart appliance, and wherein at least one of the settings is dependent upon the sleep score of the at least one individual.

18. The system of claim 16, wherein the at least one smart appliance includes at least one smart television, wherein the at least one smart television is turned on when the at least one individual wakes up, and wherein a channel selection, a streaming service selection, and/or a program selection for the at least one smart television depend on the sleep score for the at least one individual.

19. The system of claim 16, wherein the at least one remote device is operable to collect and store the sensor data to generate historical biometric data associated with each of the at least one user profile, and wherein the at least one remote device is operable to change one or more settings of the at least one smart appliance based on the historical biometric data.

20. The system of claim 16, wherein the at least one body sensor includes at least one heart rate sensor, at least one respiration sensor, at least one body temperature sensor, at least one analyte sensor, at least one brain wave sensor, at least one electromyography (EMG) sensor, at least one movement sensor, at least one body weight sensor, at least one electrooculography (EOG) sensor, at least one pulse oximeter sensor, at least one blood pressure sensor, at least one body fat sensor, and/or at least one electrodermal activity sensor.

* * * * *